(12) United States Patent
Pan et al.

(10) Patent No.: US 11,512,349 B2
(45) Date of Patent: Nov. 29, 2022

(54) METHODS FOR DETECTING DISEASE USING ANALYSIS OF RNA

(71) Applicant: GRAIL, LLC, Menlo Park, CA (US)

(72) Inventors: Wenying Pan, Menlo Park, CA (US); Matthew Larson, Menlo Park, CA (US); H. John Kim, Menlo Park, CA (US); Arash Jamshidi, Redwood City, CA (US)

(73) Assignee: GRAIL, LLC, Menlo Park, CA (US)

( * ) Notice: Subject to any disclaimer, the term of this patent is extended or adjusted under 35 U.S.C. 154(b) by 285 days.

(21) Appl. No.: 16/719,882

(22) Filed: Dec. 18, 2019

(65) Prior Publication Data

US 2020/0199671 A1 Jun. 25, 2020

Related U.S. Application Data

(60) Provisional application No. 62/781,512, filed on Dec. 18, 2018, provisional application No. 62/843,109, filed on May 3, 2019.

(51) Int. Cl.

| | |
|---|---|
| *C12Q 1/6874* | (2018.01) |
| *C12N 15/10* | (2006.01) |
| *G16B 30/00* | (2019.01) |
| *G16B 40/00* | (2019.01) |
| *C12Q 1/6886* | (2018.01) |
| *G06N 20/00* | (2019.01) |
| *G16H 70/60* | (2018.01) |
| *G16B 35/20* | (2019.01) |

(52) U.S. Cl.
CPC ....... *C12Q 1/6874* (2013.01); *C12N 15/1093* (2013.01); *C12N 15/1096* (2013.01); *C12Q 1/6886* (2013.01); *G06N 20/00* (2019.01); *G16B 30/00* (2019.02); *G16B 35/20* (2019.02); *G16B 40/00* (2019.02); *G16H 70/60* (2018.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,210,015 A | 5/1993 | Gelfand et al. | |
| 5,399,491 A | 3/1995 | Kacian et al. | |
| 5,854,033 A | 12/1998 | Lizardi | |
| 5,925,517 A | 7/1999 | Tyagi et al. | |
| 6,174,670 B1 | 1/2001 | Wittwer et al. | |
| 6,569,627 B2 | 5/2003 | Wittwer et al. | |
| 6,818,395 B1 | 11/2004 | Quake et al. | |
| 7,169,560 B2 | 1/2007 | Lapidus et al. | |
| 7,282,337 B1 | 10/2007 | Harris | |
| 7,666,593 B2 | 2/2010 | Lapidus | |
| 9,422,592 B2 * | 8/2016 | Morris et al. | C12Q 1/6886 |
| 9,982,295 B2 | 5/2018 | Talasaz | |
| 2002/0164629 A1 | 11/2002 | Quake et al. | |
| 2009/0026082 A1 | 1/2009 | Rothberg et al. | |
| 2009/0127589 A1 | 5/2009 | Rothberg et al. | |
| 2009/0156412 A1 | 6/2009 | Boyce, IV et al. | |
| 2009/0191565 A1 | 7/2009 | Lapidus et al. | |
| 2010/0035252 A1 | 2/2010 | Rothberg et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0282617 A1 | 11/2010 | Rotheberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2014/0243213 A1 | 8/2014 | Sorefan et al. | |
| 2014/0274740 A1 | 9/2014 | Srinivasan et al. | |
| 2015/0133391 A1 | 5/2015 | De Vlaminick et al. | |
| 2016/0032396 A1 | 2/2016 | Diehn et al. | |
| 2018/0203974 A1 | 7/2018 | Venn | |
| 2018/0258489 A1 | 9/2018 | Danenberg | |
| 2018/0355423 A1 * | 12/2018 | Yang et al. | G16B 35/20 |
| 2018/0357379 A1 | 12/2018 | Koh et al. | |

FOREIGN PATENT DOCUMENTS

| | | | | |
|---|---|---|---|---|
| JP | 4-262799 A | | 9/1992 | |
| WO | WO-2015/058044 A1 | | 4/2015 | |
| WO | WO-2018/005811 A1 | | 1/2018 | |
| WO | WO-2018005811 A | * | 1/2018 | .......... C12Q 1/6806 |
| WO | WO-2018/210275 A1 | | 11/2018 | |

OTHER PUBLICATIONS

Katseli et al., "Multiplex PCR-Based Detection of Circulating Tumor Cells in Lung Cancer Patients Using CK19, PTHrP, and LUNX Specific Primers," Clinical Lung Cancer 2013, 14(5):513-520. (Year: 2013).*

Abbosh, C. et al. "Phylogenetic ctDNA analysis depicts early-stage lung cancer evolution," Nature 545, 446-451 (Apr. 26, 2017).

Arroyo, J.D et al. "Argonaute2 complexes carry a population of circulating microRNAs independent of vesicles in human plasm,". Proc. Natl. Acad. Sci. U S. A. 108, 5003-5008 (Mar. 22, 2011, e-published Mar. 7, 2011).

Becker-Andre, M. et al. "Absolute mRNA quantification using the polymerase chain reaction (PCR). A novel approach by a PCR aided transcript titration assay (PATTY)," Nucleic Acids Research, 17: 9437-9446 (Nov. 25, 1989).

Bernard, P.S. et al. "Color multiplexing hybridization probes using the apolipoprotein E locus as a model system for genotyping," Anal. Biochem. 273: 221-228 (Sep. 1999).

(Continued)

*Primary Examiner* — Kaijiang Zhang
(74) *Attorney, Agent, or Firm* — Greenberg Traurig, LLP

(57) ABSTRACT

Methods for measuring subpopulations of ribonucleic acid (RNA) molecules are provided. In some embodiments, methods of generating a sequencing library from a plurality of RNA molecules in a test sample obtained from a subject are provided, as well as methods for analyzing the sequencing library to detect, e.g., the presence or absence of a disease.

17 Claims, 29 Drawing Sheets

(56) References Cited

OTHER PUBLICATIONS

Bettegowda, C. et al. "Detection of circulating tumor DNA in early- and late-stage human malignancies," Sci. Transl. Med. 6, 224ra24 (Feb. 19, 2014).
Braslaysky, I. et al. "Sequence information can be obtained from single DNA molecules," PNAS (USA), 100: 3960-3964 (Apr. 1, 2003, e-published Mar. 21, 2003).
Chan, A.K. et al. "Cell-free nucleic acids in plasma, serum and urine: a new tool in molecular diagnosis," Ann Clin Biochem. 40(Pt 2):122-130 (Mar. 2003).
Chan, K.C. et al. "Cancer genome scanning in plasma: detection of tumor-associated copy number aberrations, single-nucleotide variants, and tumoral heterogeneity by massively parallel sequencing," Clin.Chem. 59(1):211-224 (Jan. 2013, e-published Oct. 11, 2012).
Chan, K.C et al. "Noninvasive detection of cancer-associated genome-wide hypomethylation and copy number aberrations by plasma DNA bisulfite sequencing," PNAS USA 110(47):18761-18768 (Nov. 19, 2013, e-published Nov. 4, 2013).
Chen, X.Q. et al. "Telomerase RNA as a detection marker in the serum of breast cancer patients," Clin Cancer Res 6(10):3823-3826 (Oct. 2000).
Cho, H. et al. "When do changes in cancer survival mean progress? The insight from population incidence and mortality," J. Natl. Cancer Inst. Monogr. 2014(49):187-197 (Nov. 2014).
Cordero, A. et al. "FABP7 is a key metabolic regulator in HER2+ breast cancer brain metastasis," Oncogene 38(37):6445-6460 (Sep. 2019, e-published Jul. 19, 2019).
De Mattos-Arruda, L. et al. "Cell-free circulating tumour DNA as a liquid biopsy in breast cancer," Mol Oncol 10(3):464-474 (Mar. 2016, e-published Dec. 17, 2015).
De Souza, M.F. et al. "Circulating mRNAs and miRNAs as candidate markers for the diagnosis and prognosis of prostate cancer," PLoS ONE 12(9):e0184094 (Sep. 14, 2017).
Diehl, F. et al. "Circulating mutant DNA to assess tumor dynamics," Nat. Med. 14 (9):985-990 (Sep. 2008, e-published Jul. 31, 2007).
Diviacco, S. et al, "A novel procedure for quantitative polymerase chain reaction by coamplification of competitive templates," Gene 122(2): 313-320 (Dec. 15, 1992).
Duncavage, E.J. et al. "Hybrid Capture and Next-Generation Sequencing Identify Viral Integration Sites from Formalin-Fixed, Paraffin-Embedded Tissue," J Mol Diagn. 13(3): 325-333 (May 2011).
El-Hefnawy, T. et al. "Characterization of amplifiable, circulating RNA in plasma and its potential as a tool for cancer diagnostics," Clin. Chem. 50(3) 564-573 (Mar. 2004, e-published Jan. 12, 2004).
Freeman, W.M. et al. "Quantitative RT-PCR: pitfalls and potential," Biotechniques, 26(1):112-126 (Jan. 1999).
Godoy, P.M. et al. "Large Differences in Small RNA Composition Between Human Biofluids," Cell Rep. 25(5):1346-1358 (Oct. 30, 2018).
Grageda, M. et al. "DNA methylation profile and expression of surfactant protein A2 gene in lung cancer," Exp Lung Res 41(2): 93-102 (Mar. 2015, e-published Dec. 16, 2014).
Hague, I.S. et al. "Challenges in Using ctDNA to Achieve Early Detection of Cancer," bioRxiv, 237-578 (2017).
Hancock, L.A. et al. "Muc5b overexpression causes mucociliary dysfunction and enhances lung fibrosis in mic," Nat. Commun 9(1):5363 (Dec. 18, 2018).
Handa, T et al., "Caspase14 expression is associated with triple negative phenotypes and cancer stem cell marker expression in breast cancer patients," J Surg. Oncol. 116(6)706-715 (Nov. 2017, e-published Jun. 1, 2017).
Harris T. D. et al. "Single-molecule DNA sequencing of a viral genome," Science 320(5872):106-109 (Apr. 4, 2008).
Ho, G.Y.F. et al. "Differential expression of circulating microRNAs according to severity of colorectal neoplasia," Transl. Res. 166(3)225-232 (Sep. 2015, e-published Feb. 23, 2015).
Hrstka, R. et al. "The pro-metastatic protein anterior gradient-2 predicts poor prognosis in tamoxifen-treated breast cancers," Oncogene 29(34):4838-4847 (Aug. 26, 2010, e-published Jun. 7, 2010).

International Search Report dated Mar. 11, 2020, for PCT Application No. PCT/US2019/067287, filed Dec. 18, 2019, 7 pages.
Kamm, R.C. et al. "Ribonuclease activity in human plasma," Clin. Biochem. 5(4):198-200 (Dec. 1972).
Katseli, A. et al. (Sep. 2013, e-published Jun. 27, 2013). "Multiplex PCR-based detection of circulating tumor cells in lung cancer patients using CK19, PTHrP, and LUNX specific primers," Clinical Lung Cancer 14(5):513-520.
Kirkizlar, E. et al. "Detection of Clonal and Subclonal Copy-Number Variants in Cell-Free DNA from Patients with Breast Cancer Using a Massively Multiplexed PCR Methodology," Transl. Oncol. 8(5):407-416 (Oct. 2015).
Klein, E.A. et al. Development of a comprehensive cell-free DNA (cfDNA) assay for early detection of multiple tumor types: The Circulating Cell-free Genome Atlas (CCGA) study, Journal of Clinical Oncology 36(15):2018.
Kopreski, M.S. et al. "Detection of tumor messenger RNA in the serum of patients with malignant melanoma," Clin. Cancer Res. 5(8):1961-1965 (Aug. 1999).
Lee, I. et al. "The importance of standardization on analyzing circulating RNA," Mol. Diagn. Ther. 21 (3):259-268 (Jun. 2017).
Leone, G. et al. "Molecular beacon probes combined with amplification by NASBA enable homogeneous, real-time detection of RNA," Nucleic Acids Research, 26(9):2150-2155 (May 1998).
Lewis, G.H. et al. "Relationship between molecular subtype of invasive breast carcinoma and expression of gross cystic disease fluid protein 15 and mammaglobin," Am. J. Clin. Pathol. 135(4):587-591 (Apr. 2011).
Liu, R.Z et al. "A fatty acid-binding protein 7/RXRβ pathway enhances survival and proliferation in triple-negative breast cancer," J. Pathol. 228(3):310-321 (Nov. 2012, e-published Apr. 18, 2012).
Lo, K.W. et al. "Analysis of Cell-free Epstein-Barr Virus-associated RNA in the Plasma of Patients with Nasopharyngeal Carcinoma," Clin Chem 45(8 Pt 1):1292-1294 (Aug. 1999).
Lo, Y.M. et al. "Rapid clearance of fetal DNA from maternal plasma," Am. J. Hum. Genet. 64(1):218-224 (Jan. 1999).
Mackay, I.M. et al. "Real-time PCR in virology," Nucleic Acids Research 30(6):1292-1305 (Mar. 15, 2002).
Margulies, M et al. (Sep. 15, 2005, e-published Jul. 31, 2005). "Genome sequencing in microfabricated high-density picolitre reactors," Nature, 437(7057):376-380.
Maxam, A.M. et al. "A new method for sequencing DNA," PNAS USA 74(2):560-564 (Feb. 1977).
Moudrianakis E. N. et al. "Base sequence determination in nucleic acids with the electron microscope. III. Chemistry and microscopy of guanine-labeled DNA," PNAS USA 53:564-571 (Mar. 1965).
Newman, A.M. et al. "An ultrasensitive method for quantitating circulating tumor DNA with broad patient coverage," Nat. Med. 2(5):548-554 (May 2014, e-published Apr. 6, 2014).
Pizzi, M. et al. "Anterior gradient 2 overexpression in lung adenocarcinoma," Appl. Immunohistochem. Mol. Morphol. 20(1):31-36 (Jan. 2012).
Sanger, F. et al. "DNA sequencing with chain-terminating inhibitors," PNAS USA 74(12):5463-5467 (Dec. 1977).
Shen, S.Y. et al. "Sensitive tumour detection and classification using plasma cell-free DNA methylomes," Nature 563(7732):579-583 (Nov. 2018, e-published Nov. 14, 2018).
Siegel, R.L. et al. (Jan. 2017, e-published Jan. 5, 2017). "Cancer statistics," CA Cancer J Clin. 67(1):7-30.
Talhouarne, G.J.S et al. "7SL RNA in vertebrate red blood cells," RNA 24(7):908- 914 (Jul. 2018, e-published Apr. 23, 2018).
Tsui, N.B. et al. "Stability of endogenous and added RNA in blood specimens, serum, and plasma," Clin Chem. 48(10):1647-1653 (Oct. 2002).
Tzimagiorgis, G. et al. "Recovering circulating extracellular or cell-free RNA from bodily fluids," Cancer Epidemiology 35(6):580-589 (Dec. 2011, e-published Apr. 22, 2011).
Uhlen, M. et al. "Tissue-based map of the human proteome," Science 347(6220): 1260419 (Jan. 23, 2015).
Watson, M.A. et al. "Mammaglobin, a mammary-specific member of the uteroglobin gene family, is overexpressed in human breast cancer," Cancer Res. 56(4):860-865 (Feb. 15, 1996).

(56) References Cited

OTHER PUBLICATIONS

Written Opinion dated Mar. 11, 2020, for PCT Application No. PCT/US2019/067287, filed Dec. 18, 2019, 18 pages.

Xiao, J. et al., Eight potential biomarkers for distinguishing between lung adenocarcinoma and squamous cell carcinoma. Oncotarget 8(42):71759-71771 (May 3, 2017).

Zhang, H. et al. "The proteins FABP7 and OATP2 are associated with the basal phenotype and patient outcome in human breast cancer," Breast Cancer Res.Treat. 121(1):41-51 (May 2010, e-published Jul. 10, 2009).

Zhang, Z. et al. "High expression of SLC34A2 is a favorable prognostic marker in lung adenocarcinoma patients," Tumour Biol. 39(7):1010428317720212 (Jul. 2017).

Zimmerman, K. et al. "Technical aspects of quantitative competitive PCR," Biotechniques 21(2):268-279 (Aug. 1996).

\* cited by examiner

METHODS FOR DETECTING DISEASE USING ANALYSIS OF RNA

CROSS-REFERENCE

This application claims the benefit of U.S. Provisional Application No. 62/781,512, filed Dec. 18, 2018, and U.S. Provisional Application No. 62/843,109, filed May 3, 2019, which applications are incorporated herein by reference in their entireties for all purposes.

BACKGROUND OF THE INVENTION

With a total of over 1.6 million new cases each year in the United States as of 2017, cancer represents a prominent worldwide public health problem. See, Siegel et al., 2017, "Cancer statistics," CA Cancer J Clin. 67(1):7-30. Screening programs and early diagnosis have an important impact in improving disease-free survival and reducing mortality in cancer patients. As noninvasive approaches for early diagnosis foster patient compliance, they can be included in screening programs.

Cell-free nucleic acids (cfNAs) can be found in serum, plasma, urine, and other body fluids (Chan et al., "Clinical Sciences Reviews Committee of the Association of Clinical Biochemists Cell-free nucleic acids in plasma, serum and urine: a new tool in molecular diagnosis," Ann Clin Biochem. 2003; 40(Pt 2):122-130) representing a "liquid biopsy," which is a circulating picture of a specific disease. See, De Mattos-Arruda and Caldas, 2016, "Cell-free circulating tumour DNA as a liquid biopsy in breast cancer," Mol Oncol. 2016; 10(3):464-474. Similarly, cell-free RNA has been proposed as a possible analyte for cancer detection. See, Tzimagiorgis, et al., "Recovering circulating extracellular or cell-free RNA from bodily fluids," Cancer Epidemiology 2011; 35(6):580-589. These approaches represent potential non-invasive methods of screening for a variety of diseases, such as cancers.

Nevertheless, cancer remains a frequent cause of death worldwide. Over the last several decades, treatment options have improved, yet survival rates remain low. The success of treatment by surgical resection and drug-based approaches is strongly dependent on identification of early-stage tumors. However, current technologies, such as imaging and bio-marker-based approaches, frequently cannot identify tumors until the more advanced stages of the disease have set in.

Non-alcoholic steatohepatitis (NASH) is a disease of the liver characterized by inflammation and damage to the liver cells. Typically, NASH and related diseases, such as NAFLD (Nonalcoholic Fatty Liver Disease), involve inflammation of the liver related to fat accumulation, and mimic alcoholic hepatitis but are observed in patients who seldom or never consume alcohol. NASH and NAFLD are frequently reported in both men and women, although it most often appears in women and is especially prevalent in the obese. Although the disease has been observed to be accompanied by several other pathological conditions, including diabetes mellitus, hyperlipidemia, hyperglycemia, all part of the "metabolic syndrome," the cause and progression of the disease, as well as the causal or temporal relation to these conditions, is not well understood. However, in patients suffering from NAFLD and NASH in particular, certain characteristics of liver tissue and abnormalities of function are typical. Specifically, fatty deposits, tissue degeneration, inflammation, cell degeneration, cirrhosis, elevation of free fatty acids and other such abnormalities have come to be associated with nonalcoholic steatohepatitis and are frequently seen in patients suffering from forms of NAFLD.

Currently, liver biopsy is used in the clinical practice as the primary method for detection of liver ailments associated with NAFLD, NASH, fibrosis and cirrhosis. However, the use of an invasive liver biopsy as the primary means for assessing liver disease conditions discourages diagnosis, and thus, subsequent treatment, as biopsy tends to be invasive, painful, expensive, subject to sampling error and may not be possible for all patients.

Accordingly, there remains a need for new non-invasive detection modalities that can identify disease at the earliest stages, when therapeutic interventions have a greater chance of success. The current invention meets these, and other needs.

SUMMARY OF THE INVENTION

In various aspects, the present disclosure provides methods and compositions for detecting a disease state of a subject. In embodiments, the methods comprise detecting one or more markers in cell-free ribonucleic acid (cfRNA). In embodiments, detecting cfRNA comprises sequencing cfRNA from a biological sample from a subject to produce cfRNA reads. In embodiments, the method further comprises sequencing RNA from cells of a subject to produce cellular reads, and filtering the cfRNA reads to exclude cfRNA reads corresponding to one or more cellular reads. In embodiments, the cells are blood cells. In embodiments, the methods comprise filtering the cfRNA reads to exclude one or more ribosomal, mitochondrial, and/or blood-related transcripts. In embodiments, only cfRNAs reads (or read pairs) that overlap an exon-exon junction are measured. In embodiments, cfRNA corresponding to one or more markers are measured (e.g., 1, 2, 3, 4, 5, 6, 7, 8, 9, 10, 11, 12, 13, 14, 15, 20, 25, or more markers). The one or more markers can be any of the markers disclosed herein, in any combination. In embodiments, the one or more markers are associated with the disease state. In embodiments, methods comprise treating the disease state of a subject.

Aspects of the invention include methods for detecting a disease state in a subject, the method comprising: isolating a biological test sample from the subject, wherein the biological test sample comprises a plurality of cell-free ribonucleic acid (cfRNA) molecules; extracting the plurality of cfRNA molecules from the biological test sample; performing a sequencing procedure on the extracted cfRNA molecules to generate a plurality of sequence reads; performing a filtering procedure to generate an excluded population of sequence reads that originate from one or more healthy cells, and a non-excluded population of sequence reads; performing a quantification procedure on the non-excluded sequence reads; and detecting the disease state in the subject when the quantification procedure produces a value that exceeds a threshold. In embodiments, detecting one or more non-excluded sequence reads above a threshold comprises (i) detection, (ii) detection above background, or (iii) detection at a level that is greater than a level of corresponding sequence reads in subjects that do not have the condition.

Aspects of the invention further include computer-implemented methods for identifying one or more RNA sequences indicative of a disease state, the method comprising: obtaining, by a computer system, a first set of sequence reads from a plurality of RNA molecules from a first test sample from a subject known to have the disease, wherein the first test sample comprises a plurality of cell-free RNA (cfRNA) molecules; obtaining, by a computer system, a second set of sequence reads from a plurality of RNA molecules from a control sample; detecting, by a computer system, one or more RNA sequences that are present in the first set of sequence reads, and that are not present in the second set of sequence reads, to identify one or more RNA sequences that are indicative of the disease state.

In other aspects, the invention is directed to computer-implemented methods for detecting one or more tumor-derived RNA molecules in a subject, the method comprising: obtaining, by a computer system, a first set of sequence reads from a plurality of RNA molecules from a first test sample from a subject known to have, or suspected of having, a tumor, wherein the first test sample comprises a plurality of cell-free RNA (cfRNA) molecules; obtaining, by a computer system, a second set of sequence reads from a plurality of RNA molecules from a plurality of blood cells from the subject; and detecting, by a computer system, one or more RNA sequences that are present in the first set of sequence reads, and that are not present in the second set of sequence reads, to detect the one or more tumor-derived RNA molecules in the subject.

In other aspects, the invention is directed to methods for detecting a presence of a cancer, determining a cancer stage, monitoring a cancer progression, and/or determining a cancer type or cancer subtype in a subject known to have or suspected of having a cancer, the method comprising: (a) obtaining a biological test sample from the subject, wherein the biological test sample comprises a plurality of cell-free ribonucleic acid (cfRNA) molecules; (b) quantitatively detecting the presence of one or more nucleic acid sequences derived from one or more target RNA molecules in the biological test sample to determine a tumor RNA score, wherein the one or more target RNA molecules are selected from the target RNA molecules listed on any one of Tables 1-3; and (c) detecting the presence of the cancer, determining the cancer stage, monitoring the cancer progression, and/or determining the cancer type or subtype in the subject when the tumor RNA score exceeds a threshold value.

In other aspects, the invention is directed to computer-implemented methods for detecting the presence of a cancer in a subject, the method comprising: receiving a data set in a computer comprising a processor and a computer-readable medium, wherein the data set comprises a plurality of sequence reads obtained from a plurality of ribonucleic acid (RNA) molecules in a biological test sample from the subject, and wherein the computer-readable medium comprises instructions that, when executed by the processor, cause the computer to: determine an expression level of a plurality of target RNA molecules in the biological test sample; compare the expression level of each of the plurality of target RNA molecules to an RNA tissue score matrix to determine a cancer indicator score for each of the plurality of target RNA molecule; aggregating the cancer indicator score for each of the plurality of target RNA molecule to generate a cancer indicator score for the biological test sample; and detecting the presence of the cancer in the subject when the cancer indicator score for the biological test sample exceeds a threshold value.

In other aspects, the invention is directed to methods for detecting a presence of a liver disease, determining a stage of a liver disease, and/or monitoring progression of a liver disease, the method comprising: (a) obtaining a biological test sample from the subject, wherein the biological test sample comprises a plurality of cell-free ribonucleic acid (cfRNA) molecules; (b) quantitatively detecting the presence of a nucleic acid sequence derived from one or more target RNA molecules in the test sample to determine an RNA score from the one or more target RNA molecules, wherein the one or more target RNA molecules is derived from the AKR1B10 gene; and (c) detecting the presence of a liver disease, determining a stage of a liver disease, and/or monitoring progression of a liver disease in the subject when the tumor RNA score exceeds a threshold value.

In other aspects, the invention is directed to computer-implemented methods for detecting the presence of a liver disease in a subject, the method comprising: receiving a data set in a computer comprising a processor and a computer-readable medium, wherein the data set comprises a plurality of sequence reads obtained from a plurality of ribonucleic acid (RNA) molecules in a biological test sample from the subject, and wherein the computer-readable medium comprises instructions that, when executed by the processor, cause the computer to: determining an expression level for each of a plurality of target RNA molecules in the biological test sample; comparing the expression level of each of the target RNA molecules to an RNA tissue score matrix to determine a liver disease indicator score for each target RNA molecule; aggregating the liver disease indicator score for each target RNA molecule to generate a liver indicator score for the biological test sample; and detecting the presence of the liver disease in the subject when the liver disease indicator score for the biological test sample exceeds a threshold value.

In still other aspects, the invention is directed to methods for constructing an RNA tissue score matrix, the method comprising: compiling a plurality of RNA sequence reads obtained from a plurality of subjects to generate an RNA expression matrix; and normalizing the RNA expression matrix with a tissue-specific RNA expression matrix to construct the RNA tissue score matrix. In some embodiments, the RNA sequence reads are obtained from a plurality of subjects having a known cancer type to construct a cancer RNA tissue score matrix. In other embodiments, the RNA sequence reads are obtained from a plurality of subjects having a known liver disease to construct a liver disease RNA tissue score matrix.

In some aspects, the present invention provides methods of measuring a subpopulation of cell-free RNA (cfRNA) molecules of a subject. In embodiments, the method comprises (a) sequencing the cfRNA molecules to produce cfRNA sequence reads; (b) sequencing cellular RNA extracted from cells of the subject to produce cellular sequence reads; (c) performing a filtering procedure to produce a non-excluded population of cfRNA sequence reads, wherein the filtering comprises excluding cfRNA sequence reads that match one or more of the cellular sequence reads; and (d) quantifying one or more of the non-excluded sequence reads.

In some aspects, the present invention provides methods of detecting cancer in a subject. In embodiments, the method comprises: (a) measuring a plurality of target cell-free RNA (cfRNA) molecules in a sample of the subject, wherein the plurality of target cfRNA molecules are selected from transcripts of Tables 1-7; and (b) detecting the cancer, wherein detecting the cancer comprises detecting one or more of the target cfRNA molecules above a threshold level. In embodiments, detecting one or more non-excluded sequence reads above a threshold comprises (i) detection, (ii) detection above background, or (iii) detection at a level that is greater than a level of corresponding sequence reads in subjects that do not have the condition.

In some aspects, the present invention provides methods of identifying cancer biomarkers (also referred to herein as "markers") in samples collected from one or more subjects. In embodiments, the method comprises: (a) sequencing cfRNA of a biological fluid collected from subjects without cancer to produce non-cancer sequencing reads; (b) for a plurality of matched samples collected from one or more subjects with a cancer: (i) sequencing DNA and RNA collected from a cancer tissue of a matched sample to produce sequencing reads for the cancer tissue; (ii) sequencing cfDNA and cfRNA collected from a matched biological fluid of the matched sample to produce sequencing reads for the matched biological fluid; (iii) measuring a tumor fraction by relating counts of cfDNA sequencing reads for the matched biological fluid to corresponding counts of DNA sequencing reads for the cancer tissue; and (iv) measuring tumor content for one or more candidate biomarkers by multiplying a count of the RNA sequencing reads for the one or more candidate biomarkers by the tumor fraction, wherein the one or more candidate biomarkers are expressed at a higher level in the matched biological fluid than in the biological fluid collected from the subjects without cancer; (c) modeling expression of the one or more candidate biomarkers in cfRNA using the tumor content as a covariate; and (d) identifying one or more cfRNA cancer biomarkers from among the one or more candidate biomarkers based on the modeling.

In some aspects, the present invention provides computer systems for implementing one or more steps in methods of any of the various aspects disclosed herein.

In some aspects, the present invention provides non-transitory computer-readable media, having stored thereon computer-readable instructions for implementing one or more steps in methods of any of the various aspects disclosed herein.

DETAILED DESCRIPTION OF THE INVENTION

Figure 1:
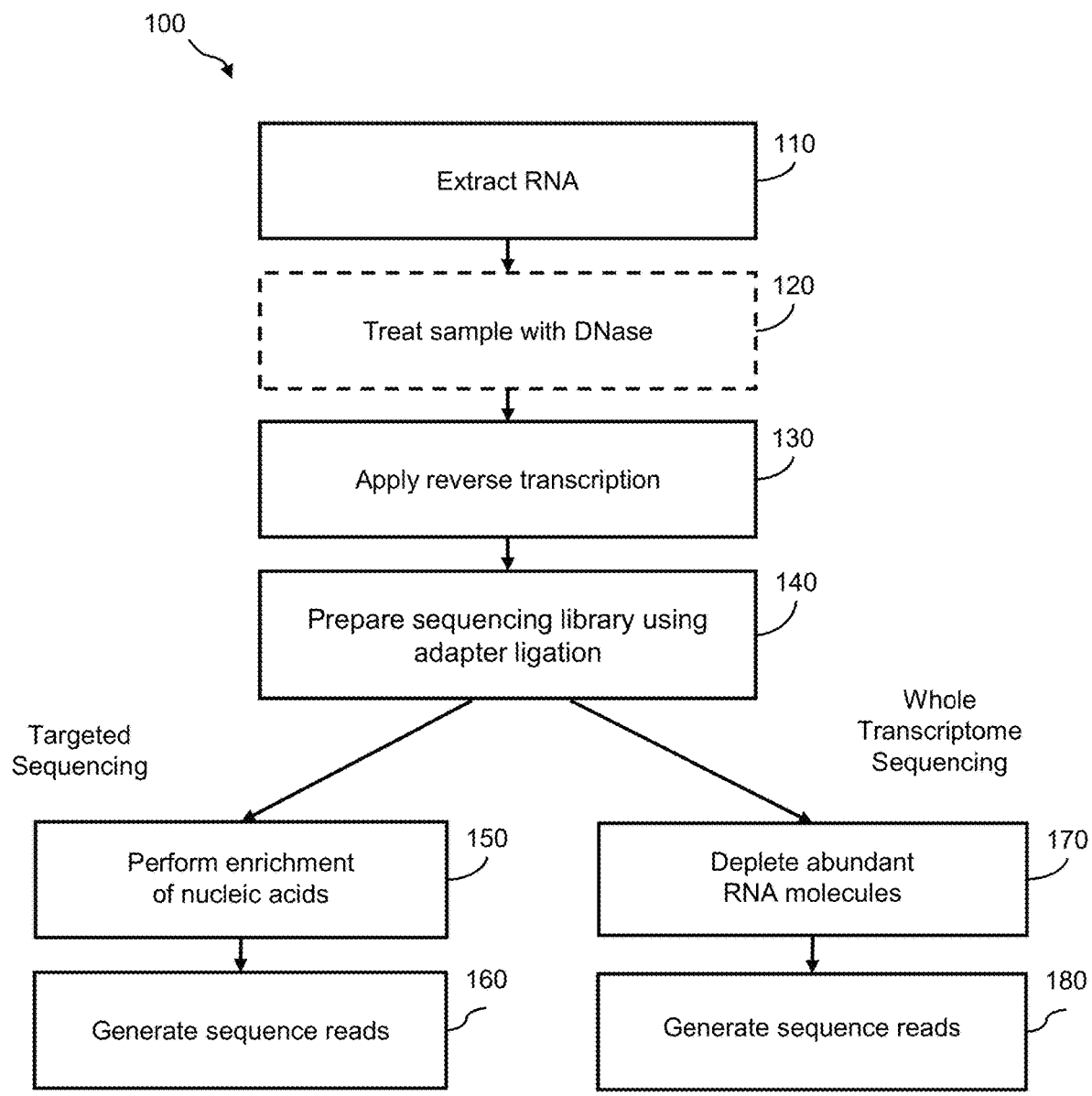
FIG. 1 is flowchart of a method for preparing a nucleic acid sample for sequencing according to one embodiment.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), provides one skilled in the art with a general guide to many of the terms used in the present application, as do the following, each of which is incorporated by reference herein in its entirety: Kornberg and Baker, DNA Replication, Second Edition (W.H. Freeman, N.Y., 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6th edition (Saunders, 2007).

All publications mentioned herein are expressly incorporated herein by reference to disclose and describe the methods and/or materials in connection with which the publications are cited.

The terms "polynucleotide", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction.

The terms "marker" and "biomarker" are used interchangeably herein to refer to a polynucleotide (e.g., a gene or an identifiable sequence fragment thereof) the level or concentration of which is associated with a particular biological state (e.g., a disease state, such as presence of cancer in general, or a particular cancer type and/or stage). In embodiments, a marker is a cfRNA of a particular gene, changes in the level of which may be detected by sequencing. cfRNA biomarkers may be referred to herein with reference to the gene from which the cfRNA derives, but does not necessitate detection of the entire gene transcript. In embodiments, only fragments of a particular gene transcript are detected. In embodiments, detecting the presence and/or level of a particular gene comprises detecting one or more cfRNA fragments comprising different sequence fragments (overlapping or non-overlapping) derived from transcripts of the same gene, which may be scored collectively as part of the same "biomarker." Additional information relating to recited gene designations, including sequence information (e.g., DNA, RNA, and amino acid sequences), full names of genes commonly identified by way of acronym, and the like are available in publicly accessible databases known to those skilled in the art, such as databases available from the National Center for Biotechnology Information (www.ncbi.nlm.nih.gov/), including GenBank (www.ncbi.nlm.nih.gov/genbank/) and the NCBI Protein database (www.ncbi.nlm.nih.gov/protein/), and UniProt (www.uniprot.org).

The term "amplicon" as used herein means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase, or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references, each of which are incorporated herein by reference herein in their entirety: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g., "real-time PCR", or "real-time NASBA" as described in Leone et al, Nucleic Acids Research, 26: 2150-2155 (1998), and like references.

The term "amplifying" means performing an amplification reaction. A "reaction mixture" means a solution containing all the necessary reactants for performing a reaction, which may include, but is not be limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments, either through natural processes, as is the case with, e.g., cfDNA fragments that can naturally occur within a biological sample, or through in vitro manipulation. Various methods of fragmenting nucleic acid are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range.

The terms "polymerase chain reaction" or "PCR", as used interchangeably herein, mean a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors that are well-known to those of ordinary skill in the art, e.g., exemplified by the following references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including, but not limited to, RT-PCR, real-time PCR, nested PCR, quantitative PCR, multiplexed PCR, and the like. The particular format of PCR being employed is discernible by one skilled in the art from the context of an application. Reaction volumes can range from a few hundred nanoliters, e.g., 200 nL, to a few hundred µL, e.g., 200 µL. "Reverse transcription PCR," or "RT-PCR," means a PCR that is preceded by a reverse transcription reaction that converts a target RNA to a complementary single stranded DNA, which is then amplified, an example of which is described in Tecott et al, U.S. Pat. No. 5,168,038, the disclosure of which is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); the disclosures of which are hereby incorporated by reference herein in their entireties. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Asymmetric PCR" means a PCR wherein one of the two primers employed is in great excess concentration so that the reaction is primarily a linear amplification in which one of the two strands of a target nucleic acid is preferentially copied. The excess concentration of asymmetric PCR primers may be expressed as a concentration ratio. Typical ratios are in the range of from 10 to 100. "Multiplexed PCR" means a PCR wherein multiple target sequences (or a single target sequence and one or more reference sequences) are simultaneously carried out in the same reaction mixture, e.g., Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, β$_2$-microglobulin, ribosomal RNA, and the like. Techniques for quantitative PCR are well-known to those of ordinary skill in the art, as exemplified in the following references, which are incorporated by reference herein in their entireties: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); and Becker-Andre et al, Nucleic Acids Research, 17: 9437-9446 (1989).

The term "primer" as used herein means an oligonucleotide, either natural or synthetic, that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, 2nd Edition (Cold Spring Harbor Press, New York, 2003).

The terms "subject" and "patient" are used interchangeably herein and refer to a human or non-human animal who is known to have, or potentially has, a medical condition or disorder, such as, e.g., a cancer.

The term "sequence read" as used herein refers to a string of nucleotides from part of, or all of, a nucleic acid molecule from a sample obtained from a subject. A sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. Sequence reads can be obtained through various methods known in the art. For example, a sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

The term "read segment" or "read" as used herein refers to any nucleotide sequences, including sequence reads obtained from a subject and/or nucleotide sequences, derived from an initial sequence read from a sample. For example, a read segment can refer to an aligned sequence read, a collapsed sequence read, or a stitched read. Furthermore, a read segment can refer to an individual nucleotide base, such as a single nucleotide variant.

The term "enrich" as used herein means to increase a proportion of one or more target nucleic acids in a sample. An "enriched" sample or sequencing library is therefore a sample or sequencing library in which a proportion of one of more target nucleic acids has been increased with respect to non-target nucleic acids in the sample.

In general, the terms "cell-free," "circulating," and "extracellular" as applied to polynucleotides (e.g. "cell-free RNA" and "cell-free DNA") are used interchangeably to refer to polynucleotides present in a sample from a subject or portion thereof that can be isolated or otherwise manipulated without applying a lysis step to the sample as originally collected (e.g., as in lysis for the extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples. The term "cell-free RNA" or "cfRNA" refers to ribonucleic acid fragments that circulate in a subject's body (e.g., bloodstream) and may originate from one or more healthy cells and/or from one or more cancer cells. Likewise, "cell-free DNA" or "cfDNA" refers to deoxyribonucleic acid molecules that circulate in a subject's body (e.g., bloodstream) and may originate from one or more healthy cells and/or from one or more cancer cells.

The term "circulating tumor RNA" or "ctRNA" refers to ribonucleic acid fragments that originate from tumor cells or other types of cancer cells, which may be released into a subject's body (e.g., bloodstream) as a result of biological processes, such as apoptosis or necrosis of dying cells, or may be actively released by viable tumor cells.

The term "dark channel RNA" or "dark channel cfRNA molecule" or "dark channel gene" as used herein refers to an RNA molecule or gene whose expression in healthy cells is very low or nonexistent. Accordingly, identification, detection, and/or quantification of dark channel RNA (cfRNA) molecules improves signal-to-noise, and improvements in sensitivity and specificity, in assessment of a disease state, such as cancer.

"Treating" or "treatment" as used herein (and as well-understood in the art) includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein includes prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent", as pertains to a disease or condition of a subject, refers to a decrease in the occurrence of one or more corresponding symptoms in the subject. As indicated above, the prevention may be complete (no detectable symptoms) or partial, such that fewer symptoms are observed, and/or with lower incidence, than would likely occur absent treatment.

Aspects of the invention include methods for detecting a disease state, (e.g., a presence or absence of cancer), and/or a tissue of origin of the disease in a subject, based on analysis of one or more RNA molecules in a sample from the subject. In some embodiments, a method for detecting a disease state in a subject comprises isolating a biological test sample from the subject, wherein the biological test sample comprises a plurality of cell-free ribonucleic acid (cfRNA) molecules, extracting the cfRNA molecules from the biological test sample, performing a sequencing procedure on the extracted cfRNA molecules to generate a plurality of sequence reads, performing a filtering procedure to generate an excluded population of sequence reads that originate from one or more healthy cells, and a non-excluded population of sequence reads, and performing a quantification procedure on the non-excluded sequence reads. In embodiments, the methods comprise detecting the disease state in the subject when the quantification procedure produces a value that exceeds a threshold. In embodiments, detecting one or more non-excluded sequence reads above a threshold comprises (i) detection, (ii) detection above background, or (iii) detection at a level that is greater than a level of corresponding sequence reads in subjects that do not have the condition. In certain embodiments, the threshold value is an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8.

In some embodiments, the methods involve the use of sequencing procedure for detecting and quantifying the cfRNA molecules that are extracted from a biological test sample. For example, in certain embodiments a sequencing procedure involves performing a reverse transcription procedure on the cfRNA molecules to produce a plurality of cDNA/RNA hybrid molecules, degrading the RNA of the hybrid molecules to produce a plurality of single-stranded cDNA molecule templates, synthesizing a plurality of double-stranded DNA molecules from the single-stranded cDNA molecule templates, ligating a plurality of double-stranded DNA adapters to the plurality of double-stranded DNA molecules producing a sequencing library, and performing a sequencing procedure on at least a portion of the sequencing library to obtain a plurality of sequence reads. In certain embodiments, synthesizing the double-stranded DNA molecules involves performing a strand-displacement reverse transcriptase procedure.

In some embodiments, the methods utilize whole transcriptome sequencing procedures. In other embodiments, a sequencing procedure involves a targeted sequencing procedure, wherein one or more of the cfRNA molecules are enriched from the biological test sample before preparing a sequencing library. In accordance with this embodiment, one or more cfRNA molecules indicative of the disease state are targeted for enrichment. For example, in some embodiments, the one or more targeted cfRNA molecules are derived from one or more genes selected from the group consisting of: AGR2, BPIFA1, CASP14, CSN1S1, DISP2, EIF2D, FABP7, GABRG1, GNAT3, GRHL2, HOXC10, IDI2-AS1, KRT16P2, LALBA, LINC00163, NKX2-1, OPN1SW, PADI3, PTPRZ1, ROS1, S100A7, SCGB2A2, SERPINB5, SFTA3, SFTPA2, SLC34A2, TFF1, VTCN1, WFDC2, MUCSB, SMIM22, CXCL17, RNU1-1, and KLK5. In some embodiments, one or more target RNA molecules are derived from one or more genes selected from the group consisting of ROS1, NKX2-1, GGTLC1, SLC34A2, SFTPA2, BPIFA1, SFTA3, GABRG1, AGR2, GNAT3, MUCSB, SMIM22, CXCL17, and WFDC2. In some embodiments, one or more target RNA molecules are derived from one or more genes selected from the group consisting of SCGB2A2, CSN1S1, VTCN, FABP7, LALBA, RNU1-1, OPN1SW, CASP14, KLK5, and WFDC2. In some embodiments, one or more target RNA molecules are derived from one or more genes selected from the group consisting of CASP14, CRABP2, FABP7, SCGB2A2, SERPINB5, TRGV10, VGLL1, TFF1, and AC007563.5. In still other embodiments, the targeted RNA molecule is derived from the AKR1B10, C3, and/or PIEXO2 gene(s).

Aspects of the invention involve analysis of one or more dark channel RNA molecules, whose expression in the plasma of healthy subjects is very low or nonexistent. Due to their low expression level in the plasma of healthy subjects, dark channel RNA molecules provide a high signal to noise ratio that can be used in conjunction with the present methods.

Some aspects of the invention involve filtering procedures that are used to generate an excluded population of sequence reads that originate from one or more healthy cells, and a non-excluded population of sequence reads that are used in subsequent analyses. In certain embodiments, the filtering procedure involves comparing each sequence read from the cfRNA molecules extracted from the biological test sample to a control data set of RNA sequences, identifying one or more sequence reads that match one or more sequence reads in the control data set of RNA sequences, and placing each sequence read that matches the one or more sequence reads in the control data set of RNA sequences in the excluded population of sequence reads.

In some embodiments, a control data set of RNA sequences includes a plurality of sequence reads obtained from one or more healthy subjects. In some embodiments, a control data set of RNA sequences includes a plurality of sequence reads obtained from a plurality of blood cells from the subject. For example, in some embodiments, a plurality of sequence reads are obtained from a subject's white blood cells (WBCs).

Biological Samples

The present invention involves obtaining a test sample, e.g., a biological test sample, such as a tissue and/or body fluid sample, from a subject for purposes of analyzing a plurality of nucleic acids (e.g., a plurality of cfRNA molecules) therein. Samples in accordance with embodiments of the invention can be collected in any clinically-acceptable manner. Any sample suspected of containing a plurality of nucleic acids can be used in conjunction with the methods of the present invention. In some embodiments, a sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the terms "body fluid" and "biological fluid" refer to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a sample can comprise a fine needle aspirate or biopsied tissue. In some embodiments, a sample can comprise media containing cells or biological material. In some embodiments, a sample can comprise a blood clot, for example, a blood clot that has been obtained from whole blood after the serum has been removed. In some embodiments, a sample can comprise stool. In one preferred embodiment, a sample is drawn whole blood. In one aspect, only a portion of a whole blood sample is used, such as plasma, red blood cells, white blood cells, and platelets. In some embodiments, a sample is separated into two or more component parts in conjunction with the present methods. For example, in some embodiments, a whole blood sample is separated into plasma, red blood cell, white blood cell, and platelet components.

In some embodiments, a sample includes a plurality of nucleic acids not only from the subject from which the sample was taken, but also from one or more other organisms, such as viral DNA/RNA that is present within the subject at the time of sampling.

Nucleic acid can be extracted from a sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety. In one preferred embodiment, cell free ribonucleic acid (e.g., cfRNA) is extracted from a sample.

In embodiments, the sample is a "matched" or "paired" sample. In general, the terms "matched sample" and "paired sample" refer to a pair of samples of different types collected from the same subject, preferably at about the same time (e.g., as part of a single procedure or office visit, or on the same day). In embodiments, the different types are a tissue sample (e.g., cancer tissue, as in a resection or biopsy sample) and a biological fluid sample (e.g., blood or a blood fraction). The terms may also be used to refer to polynucleotides derived from the matched sample (e.g., polynucleotides extracted from a cancer tissue, paired with cell-free polynucleotides from a matched biological fluid sample), or sequencing reads thereof. In embodiments, a plurality of paired samples are analyzed, such as in identifying cancer biomarkers. The plurality of paired samples may be from the same individual collected at different times (e.g., as in a paired sample from an early stage of cancer, and a paired sample from a later stage of cancer), from different individuals at the same or different times, or a combination of these. In embodiments, the matched samples are from different subjects. In embodiments, the matched samples in a plurality are from subjects with the same cancer type, and optionally the same cancer stage.

Example Assay Protocol

FIG. 1 is flowchart of a method 100 for preparing a nucleic acid sample for sequencing according to one embodiment. The method 100 includes, but is not limited to, the following steps. For example, any step of the method 100 may comprise a quantitation sub-step for quality control or other laboratory assay procedures known to one skilled in the art.

In step 110, a ribonucleic acid (RNA) sample is extracted from a subject. The RNA sample may comprise the whole human transcriptome, or any subset of the human transcriptome. The sample may be extracted from a subject known to have or suspected of having a disease (e.g., cancer). The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may further comprise cfDNA. If a subject has a disease (e.g., cancer), cfRNA in an extracted sample may be present at a detectable level for diagnosis.

In step 120, the nucleic acid sample including RNA molecules is optionally treated with a DNase enzyme. The DNase may remove DNA molecules from the nucleic acid sample to reduce DNA contamination of the RNA molecules. After RNA molecules are converted into DNA, it may be difficult to distinguish the RNA-converted DNA and genomic DNA originally found in the nucleic acid sample. Applying the DNase allows for targeted amplification of molecules originating from cfRNA. The DNase process may include steps for adding a DNase buffer, mixing the sample applied with DNase using a centrifuge, and incubation. In some embodiments, step 120 includes one or more processes based on the DNase treatment protocol described in the Qiagen QIAamp Circulating Nucleic Acid Handbook.

In step 130, a reverse transcriptase enzyme is used to convert the RNA molecules in the nucleic acid sample into complementary DNA (cDNA). The reverse transcriptase process may include a first-strand synthesis step (generation of a cDNA strand via reverse transcription), degradation of the RNA strand to produce a single-stranded cDNA molecule, and synthesis of a double-stranded DNA molecules from the single-stranded cDNA molecule using a polymerase. During first-strand synthesis, a primer anneals to the 3' end of a RNA molecule. During second-strand synthesis, a different primer anneals to the 3' end of the cDNA molecule.

In step 140, a sequencing library is prepared. For example, as is well known in the art, adapters can be ligated to one or both ends of a dsDNA molecule to prepare a library for sequencing. In one embodiment, the adapters utilized may include one or more sequencing oligonucleotides for use in subsequent cluster generation and/or sequencing (e.g., known P5 and P7 sequences for used in sequencing by synthesis (SBS) (Illumina, San Diego, Calif.)). In another embodiment, the adapter includes a sample specific index sequence, such that, after library preparation, the library can be combined with one or more other libraries prepared from individual samples, thereby allowing for multiplex sequencing. The sample specific index sequence can comprise a short oligonucleotide sequence having a length of from about 2 nt to about 20 nt, from about 2 nt to about 10 nt, from about 2 to about 8 nt, or from about 2 to about 6 nt. In another embodiment, the sample specific index sequence can comprise a short oligonucleotide sequence greater than about 2, 3, 4, 5, 6, 7, or 8 nucleotides (nt) in length.

Optionally, during library preparation, unique molecular identifiers (UMI) can be added to the nucleic acid molecules in the sample through adapter ligation. The UMIs are short nucleic acid sequences (e.g., 4-10 base pairs) that are added to one or both ends of nucleic acid fragments during adapter ligation. In some embodiments, UMIs are degenerate base pairs that serve as a unique tag that can be used to identify sequence reads originating from a specific nucleic acid fragment. During PCR amplification following adapter ligation, the UMIs are replicated along with the attached nucleic acid fragment, which provides a way to identify sequence reads that came from the same original nucleic acid molecule in downstream analysis.

For embodiments including targeted sequencing of RNA, in step 150, targeted nucleic acid sequences are enriched from the library. During enrichment, hybridization probes (also referred to herein as "probes") are used to target, and pull down, nucleic acid fragments informative for the presence or absence of a disease (e.g., cancer), disease status (e.g., cancer status), or a disease classification (e.g., cancer type or tissue of origin). For a given workflow, the probes may be designed to anneal (or hybridize) to a target (complementary) nucleic acid strand (e.g., a DNA strand converted from RNA). The probes may range in length from 10s, 100s, or 1000s of base pairs. In one embodiment, the probes are designed based on a gene panel to analyze particular target regions of the genome (e.g., of the human or another organism) that are suspected to correspond to certain cancers or other types of diseases. Moreover, the probes may cover overlapping portions of a target region. In other embodiments, targeted RNA molecules can be enriched using hybridization probes prior to conversion of the RNA molecules to cDNA strands using reverse transcriptase (not shown). In general, any known method in the art can be used to isolate, and enrich for, probe-hybridized target nucleic acids. For example, as is well known in the art, a biotin moiety can be added to the 5'-end of the probes (i.e., biotinylated) to facilitate isolation of target nucleic acids hybridized to probes using a streptavidin-coated surface (e.g., streptavidin-coated beads).

Additionally, for targeted sequencing, in step 160, sequence reads are generated from the enriched nucleic acid sample. Sequencing data may be acquired from the enriched DNA sequences (i.e., DNA sequences derived, or converted, from RNA sequences) by known means in the art. For example, the method 100 may include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In other embodiments, for example, in a whole transcriptome sequencing approach (e.g., instead of targeted sequencing), in step 170, abundant RNA species are depleted from the nucleic acid sample. For example, in some embodiments, ribosomal RNA (rRNA) and/or transfer RNA (tRNA) species can be depleted. Available commercial kits, such as RiboMinus™ (ThermoFisher Scientific) or AnyDeplete (NuGen), can be used for depletion of abundant RNA species. In an embodiment, after depletion of nucleic acids (e.g., converted DNA) derived from abundant RNA molecules, sequence reads are generated in step 180.

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. The reference genome may comprise the whole transcriptome, or any portion thereof (e.g., a plurality of targeted transcripts). In another embodiment, the reference genome can be the whole genome from an organism being tested and sequence reads derived from (or reverse transcribed from) extracted RNA molecules are aligned to the reference genome to determine location, fragment length, and/or start and end positions. For example, in one embodiment, sequence reads are aligned to human reference genome hg19. The sequence of the human reference genome, hg19, is available from Genome Reference Consortium with a reference number, GRCh37/hg19, and also available from Genome Browser provided by Santa Cruz Genomics Institute. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

Identification of Dark Channel RNA Molecules

Aspects of the invention include computer-implemented methods for identifying one or more RNA sequences indicative of a disease state in a subject (or "dark channel RNA molecules"). In some embodiments, the methods involve obtaining, by a computer system, a first set of sequence reads from a plurality of RNA molecules from a first test sample obtained from a subject known to have the disease, wherein the first test sample comprises a plurality of cell-free RNA (cfRNA) molecules, and a second set of sequence reads from a plurality of RNA molecules from a control sample, detecting, one or more RNA sequences that are present in the first set of sequence reads, and that are not present in the second set of sequence reads, to identify one or more RNA sequences that are indicative of the disease state. In some embodiments, the first test sample obtained from the patient comprises a bodily fluid (e.g., blood, plasma, serum, urine, saliva, pleural fluid, pericardial fluid, cerebrospinal fluid (CSF), peritoneal fluid, or any combination thereof). In one preferred embodiment, a test sample obtained from the patient is a plasma sample. In some embodiments, the control sample comprises a plurality of RNA molecules obtained from healthy cells from the subject (e.g., white blood cells).

Figure 2:
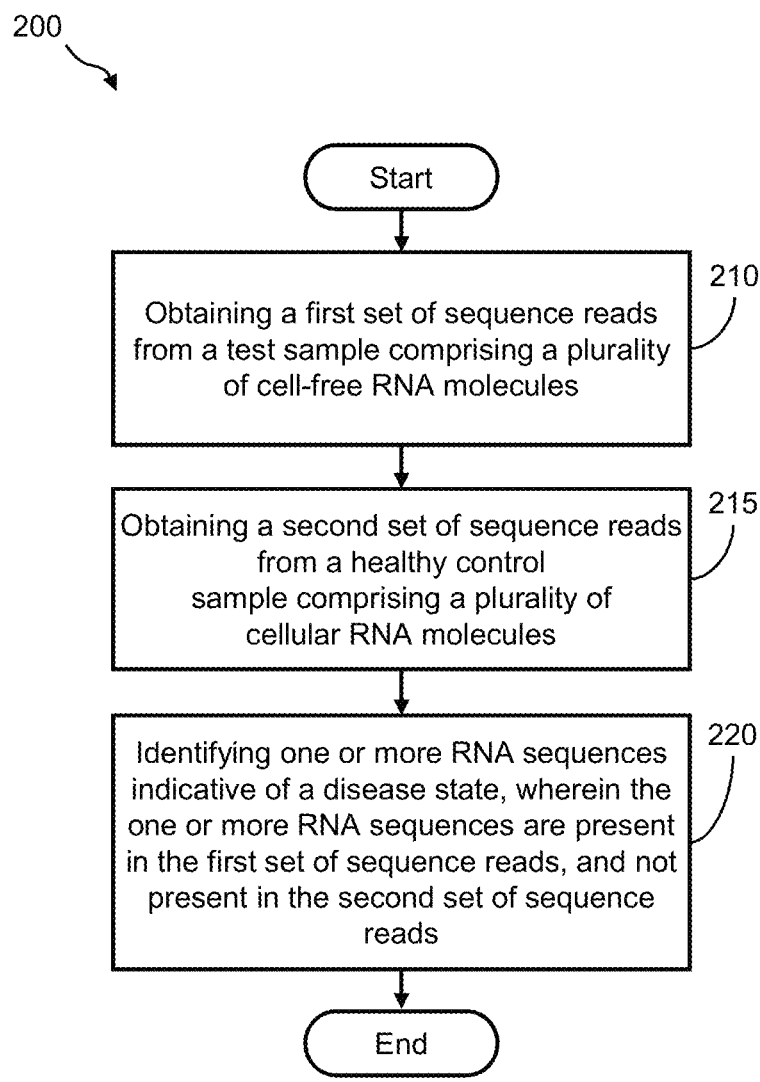
FIG. 2 is a flow diagram illustrating a method for identifying one or more RNA sequences indicative of a disease state, in accordance with one embodiment of the present invention.

FIG. 2 is a flow diagram illustrating a method for identifying one or more RNA sequences indicative of a disease state, in accordance with one embodiment of the present invention. As shown in FIG. 2, at step 210, a first set of sequence reads is obtained from a biological test sample comprising a plurality of cell-free RNA (cfRNA) molecules. The cell-free containing biological test sample can be any a bodily fluid, such as, blood, plasma, serum, urine, pleural fluid, cerebrospinal fluid, saliva, or ascitic fluid. In accordance with this embodiment, the cfRNA biological test sample is obtained from a test subject known to have, or suspected of having a disease, the cfRNA molecules extracted from the sample and sequence reads determined (as described elsewhere herein). For example, in one embodiment, a complementary DNA strand is synthesized using a reverse transcription step generating a cDNA/RNA hybrid molecule, the RNA molecule degraded, a double stranded DNA molecule synthesized from the cDNA strand using a polymerase, a sequencing library prepared, and sequence reads determined using a sequencing platform. The sequencing step can be any carried out using any known sequencing platform in the art, such as, any massively parallel sequencing platform, including a sequencing-by-synthesis platform (e.g., Illumina's HiSeq X) or a sequencing-by-ligation platform (e.g. the Life Technologies SOLiD platform), the Ion Torrent/Ion Proton, semiconductor sequencing, Roche 454. single molecular sequencing platforms (e.g. Helicos. Pacific Biosciences and nanopore), as previously described. Alternatively, other means for detecting and quantifying the sequence reads can be used, for example, array-based hybridization, probe-based in-solution hybridization, ligation-based assays, primer extension reaction assays, can be used to determine sequence reads from DNA molecules (e.g., converted from RNA molecules), as one of skill in the art would readily understand.

At step 220, a second set of sequence reads is obtained from a healthy control sample. In one embodiment, the healthy control sample is from the same subject and comprises a plurality of cellular RNA molecules. For example, the control sample can be blood cells, such as white blood cells, and the plurality of sequence reads derived from RNA molecules extracted from the blood cells. In accordance with this embodiment, the RNA molecules are extracted from the healthy control sample (e.g., blood cells), converted to DNA, a sequencing library prepared, and the second set of sequence reads determined (as described elsewhere herein). In other embodiments, the healthy control sample can be a database of sequence data determined for RNA sequences obtained from a healthy subject, or from healthy cells.

At step 230, sequence reads from the first set of sequence reads and the second set of sequence reads are compared to identifying one or more RNA molecules indicative of a disease state. Moreover, one or more sequence reads (derived from RNA molecules) present in the first set of sequence reads, and not present in the second set of sequence reads, are identified as derived from RNA molecules indicative of a disease state. For example, the first set of sequence reads can comprise sequence reads derived from cfRNA molecules from a plasma sample obtained from a subject known to have, or suspected of having, a disease (e.g., cancer). And the second set of sequence reads can comprise sequence reads derived from RNA molecules from healthy cells (e.g., white blood cells). By comparing, and removing, the second set of sequence reads derived from healthy cells from the first set of sequence reads derived from a cell-free RNA sample, one can identify the sequence reads derived from a disease state (e.g., cancer).

In some embodiments, a control data set of RNA sequences includes a plurality of sequence reads obtained from one or more healthy subjects. In certain embodiments, the second set of sequence reads comprises RNA sequence information obtained from a public database. Public databases that can be used in accordance with embodiments of the invention include the tissue RNA-seq database GTEx (available at gtexportal.org/home). In some embodiments, a control data set of RNA sequences includes a plurality of sequence reads obtained from a plurality of blood cells from the subject. For example, in some embodiments, a plurality of sequence reads are obtained from a subject's white blood cells (WBCs).

Detection of Tumor-Derived RNA Molecules

Aspects of the invention include computer-implemented methods for detecting one or more tumor-derived RNA molecules in a subject. In some embodiments, the methods involve: obtaining, by a computer system, a first set of sequence reads from a plurality of RNA molecules from a first test sample from a subject known to have a tumor, wherein the first test sample comprises a plurality of cell-free RNA (cfRNA) molecules; obtaining, by a computer system, a second set of sequence reads from a plurality of RNA molecules from a plurality of blood cells from the subject; and detecting, by a computer system, one or more RNA sequences that are present in the first set of sequence reads, and that are not present in the second set of sequence reads, to detect the one or more tumor-derived RNA molecules in the subject.

In some embodiments, the first test sample obtained from the patient comprises blood, plasma, serum, urine, saliva, pleural fluid, pericardial fluid, cerebrospinal fluid (CSF), peritoneal fluid, or any combination thereof. In one preferred embodiment, a test sample obtained from the patient is a plasma sample. In some embodiments, the plurality of blood cells obtained from the subject are white blood cells (WBCs).

Figure 3:
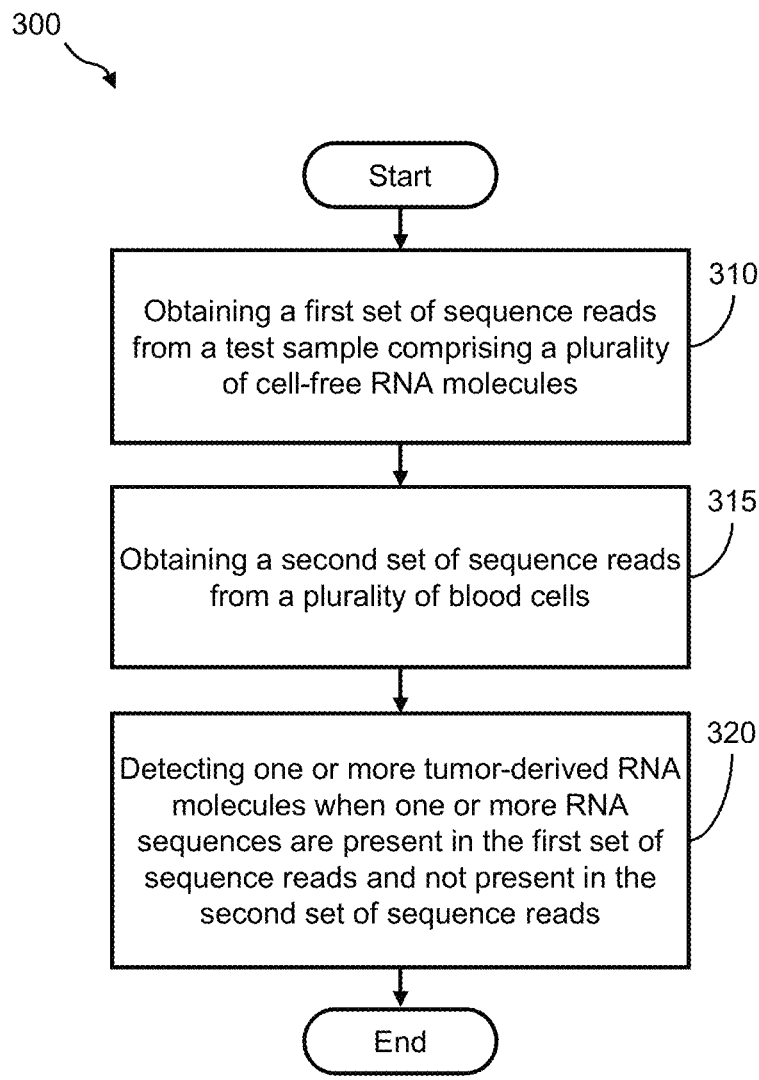
FIG. 3 is a flow diagram illustrating a method for identifying one or more tumor-derived RNA sequences, in accordance with one embodiment of the present invention.

FIG. 3 is a flow diagram illustrating a method for identifying one or more tumor-derived RNA sequences, in accordance with one embodiment of the present invention. At step 310, a first set of sequence reads is obtained from a biological test sample comprising a plurality of cell-free RNA (cfRNA) molecules. In accordance with this embodiment, the cfRNA biological test sample is obtained from a test subject known to have, or suspected of having a disease, the cfRNA molecules extracted from the sample and sequence reads determined (as described elsewhere herein). For example, in one embodiment, a complementary DNA strand is synthesized using a reverse transcription step generating a cDNA/RNA hybrid molecule, the RNA molecule degraded, a double stranded DNA molecule synthesized from the cDNA strand using a polymerase, a sequencing library prepared, and sequence reads determined using a sequencing platform. The sequencing step can be any carried out using any known sequencing platform in the art, as previously described. Alternatively, other means for determining the sequence reads can be used, for example, array-based hybridization, probe-based in-solution hybridization, ligation-based assays, primer extension reaction assays, can be used to detect and/or quantify sequence reads obtained from DNA molecules (e.g., converted from RNA molecules), as one of skill in the art would readily understand.

At step 315, a second set of sequence reads is obtained from blood cells (e.g., white blood cells or buffy coat). In one embodiment, the blood cells are obtained from the same subject and RNA molecules extracted therefrom. In accordance with this embodiment, the RNA molecules are extracted from the blood cells, converted to DNA, a sequencing library prepared, and the second set of sequence reads determined (as described elsewhere herein). In general, any known method in the art can be used to extract and purify cell-free nucleic acids from the test sample. For example, cell-free nucleic acids can be extracted and purified using one or more known commercially available protocols or kits, such as the QIAamp circulating nucleic acid kit (Qiagen).

At step 320, one or more tumor-derived RNA molecules is detected when one or more RNA sequences are present in the first set of sequence reads and not present in the second set of sequence reads. Moreover, one or more sequence reads (derived from RNA molecules) present in the first set of sequence reads, and not present in the second set of sequence reads, are identified as derived from RNA molecules indicative of a disease state. For example, the first set of sequence reads can comprise sequence reads derived from cfRNA molecules from a plasma sample obtained from a subject known to have, or suspected of having, a disease (e.g., cancer). And the second set of sequence reads can comprise sequence reads derived from RNA molecules from blood cells (e.g., white blood cells). By comparing, and removing, the second set of sequence reads derived from blood cells from the first set of sequence reads derived from a cell-free RNA sample, one can identify the sequence reads derived from a tumor.

Detecting a Disease State Using a Dark Channel RNA Molecules

Figure 4:
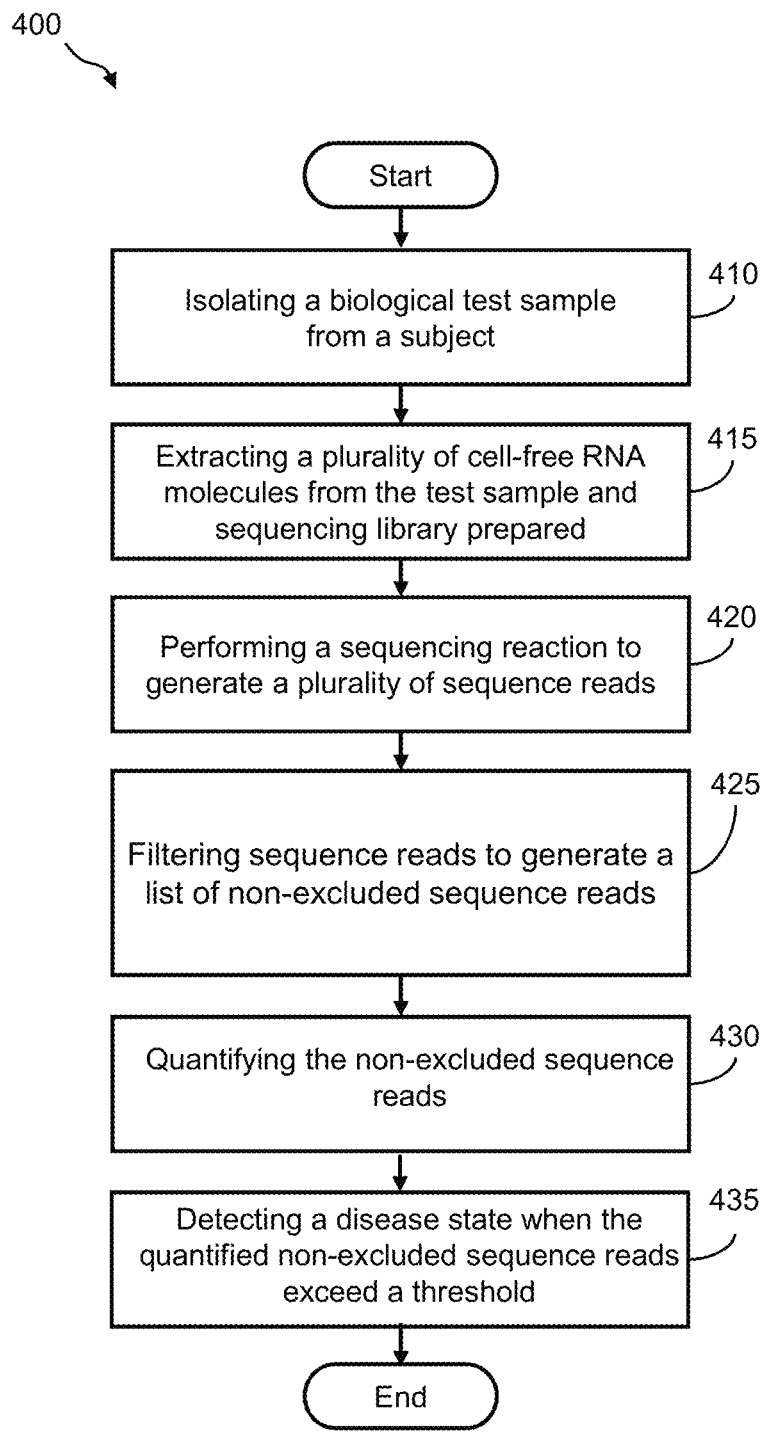
FIG. 4 is a flow diagram illustrating a method for detecting the presence of cancer, determining a state of cancer, monitoring cancer progression, and/or determining cancer type in a subject, in accordance with one embodiment of the present invention.

FIG. 4 is a flow diagram illustrating a method for detecting the presence of cancer, determining a state of cancer, monitoring cancer progression, and/or determining cancer type in a subject, in accordance with one embodiment of the present invention. At step 410, a biological test sample is extracted from a subject. As previously described, in one embodiment, the test sample can be a bodily fluid (e.g., blood, plasma, serum, urine, saliva, pleural fluid, pericardial fluid, cerebrospinal fluid (CSF), peritoneal fluid, or any combination thereof) comprising a plurality of cell-free RNA molecules.

At step 415, a plurality of cell-free RNA molecules are extracted from the test sample and a sequencing library prepared. In general, any known method in the art can be used to extract and purify cell-free nucleic acids from the test sample. For example, cell-free nucleic acids (cfRNA molecules) can be extracted and purified using one or more known commercially available protocols or kits, such as the QIAamp circulating nucleic acid kit (Qiagen). After extraction, the cfRNA molecules are used to prepare a sequencing library. In one embodiment, a reverse transcription step is used to produce a plurality of cDNA/RNA hybrid molecules, the RNA strand degraded to produce a single-stranded cDNA molecule, a second strand synthesized to produce a plurality of double-stranded DNA molecules from the single-stranded cDNA molecule templates, and DNA adapters ligated to the plurality of double-stranded DNA molecules to generate a sequencing library. As previously described, the DNA adapters may include one or more sequencing oligonucleotides for use in subsequent cluster generation and/or sequencing (e.g., known P5 and P7 sequences for used in sequencing by synthesis (SBS) (Illumina, San Diego, Calif.)). In another embodiment, the adapter includes a sample specific index sequence, such that, after library preparation, the library can be combined with one or more other libraries prepared from individual samples, thereby allowing for multiplex sequencing. In another embodiment, unique molecular identifiers (UMI) are added through adapter ligation.

At step 420, a sequencing reaction is performed to generate a plurality of sequence reads. In general, any method known in the art can be used to obtain sequence data or sequence reads from the sequencing library. For example, in one embodiment, sequencing data or sequence reads from the sequencing library can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step can be performed prior to sequencing.

At step 425, sequence reads obtained from the cfRNA sample are filtered to generate a list of non-excluded sequence reads and the non-excluded sequence reads quantified at step 430. For example, as described elsewhere herein, the sequence reads obtained from the cfRNA sample can be filtered to exclude sequence known to be present in healthy cells. In one embodiment, RNA molecules extracted from healthy cells (e.g., white blood cells) are sequenced deriving sequence reads that are excluded from the cfRNA derived sequence reads to obtain non-excluded sequence reads. In another embodiment, RNA sequencing data from a database (e.g., a public database) can be used to filter out or exclude sequences known to be present in healthy cells reads comprises to obtain non-excluded sequence reads.

At step 435, a disease state is detected when the quantified non-excluded sequence reads exceed a threshold. In certain embodiments, the threshold value is an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8.

Aspects of the invention relate to methods for detecting a presence of a cancer, determining a cancer stage, monitoring a cancer progression, and/or determining a cancer type in a subject known to have, or suspected of having a cancer. In some embodiments, the methods involve: (a) obtaining a plurality of sequence reads from a plurality of cfRNA molecules in a biological test sample from the subject; (b) quantitatively detecting the presence of one or more sequences derived from one or more RNA markers in the biological test sample to determine a tumor RNA score, wherein the one or more RNA markers are selected from the group consisting of one or more targeted RNA molecules; and (c) detecting the presence of the cancer, determining the cancer stage, monitoring the cancer progression, and/or determining the cancer type in the subject when the tumor RNA score exceeds a threshold value. In certain embodiments, the threshold value is an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8.

Quantitative detection methods in accordance with embodiments of the invention can include nucleic acid sequencing procedures, such as next-generation sequencing. In certain embodiments, sequencing can involve whole transcriptome sequencing. In certain embodiments, sequencing can involve enriching a sample for one or more targeted RNA sequences of interest prior to conducting the sequencing procedure. Alternatively, other means for detecting and quantifying sequence reads can be used, for example, array-based hybridization, probe-based in-solution hybridization, ligation-based assays, primer extension reaction assays, can be used to determine sequence reads from DNA molecules (e.g., converted from RNA molecules), as one of skill in the art would readily understand.

Figure 5:
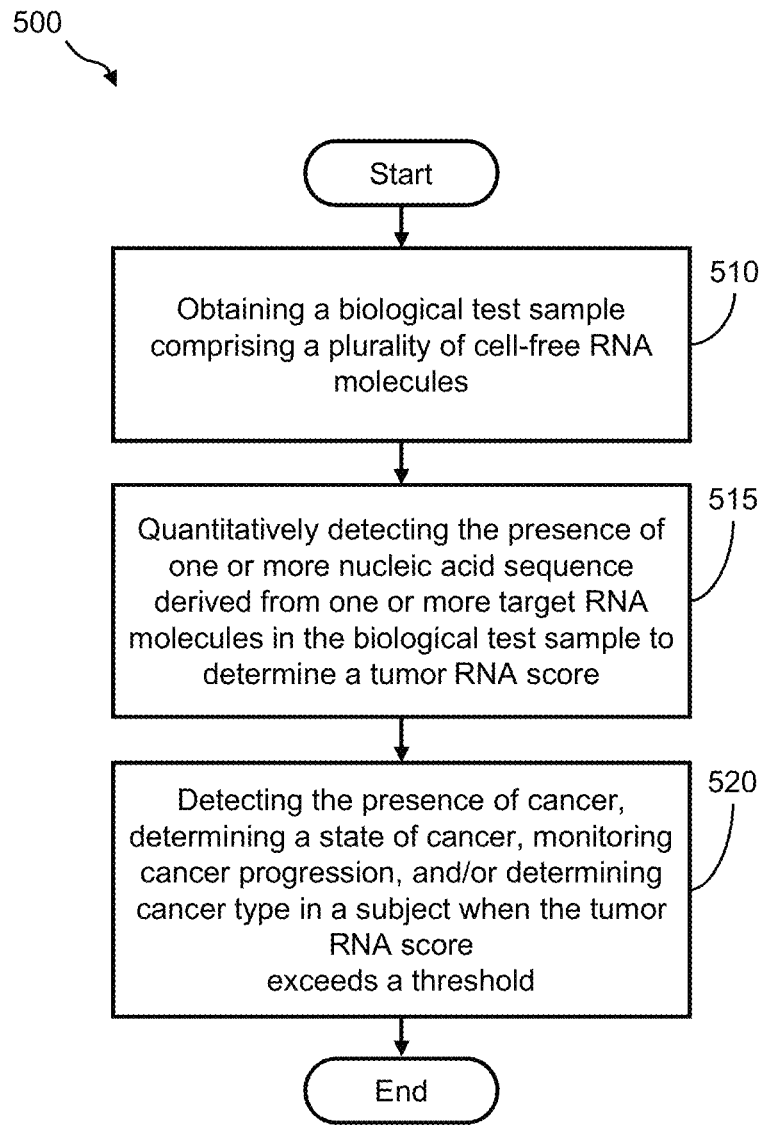
FIG. 5 is a flow diagram illustrating a method for detecting a disease state from one or more sequence reads derived from one or more targeted RNA molecules, in accordance with one embodiment of the present invention.

FIG. 5 is a flow diagram illustrating a method for detecting a disease state from one or more sequence reads derived from one or more targeted RNA molecules, in accordance with another embodiment of the present invention. At step 510, a biological test sample comprising a plurality of cell-free RNA molecules is obtained. In one embodiment, the biological test sample is a bodily fluid (e.g., a blood, plasma, serum, urine, saliva, pleural fluid, pericardial fluid, cerebrospinal fluid (CSF), peritoneal fluid sample, or any combination thereof).

At step 515, the presence of one or more nucleic acid sequence derived from one or more target RNA molecules in the biological test sample are detected, and quantified, to determine a tumor RNA score. As described elsewhere herein, nucleic acids derived from RNA molecules can be detected and quantified using any known means in the art. For example, in accordance with one embodiment, nucleic acids derived from RNA molecules are detected and quantified using a sequencing procedure, such as a next-generation sequencing platform (e.g., HiSeq or NovaSeq, Illumina, San Diego, Calif.). In other embodiments, nucleic acids derived from RNA molecules are detected and quantified using a microarray, reverse transcription PCR, real-time PCR, quantitative real-time PCR, digital PCR, digital droplet PCR, digital emulsion PCR, multiplex PCR, hybrid capture, oligonucleotide ligation assays, or any combination thereof. As described elsewhere, in one embodiment, cell-free nucleic acids (cfRNA molecules) can be extracted and purified using one or more known commercially available protocols or kits, such as the QIAamp circulating nucleic acid kit (Qiagen). After extraction, the cfRNA molecules are used to prepare a sequencing library. In one embodiment, a reverse transcription step is used to produce a plurality of cDNA/RNA hybrid molecules, the RNA strand degraded to produce a single-stranded cDNA molecule, a second strand synthesized to produce a plurality of double-stranded DNA molecules from the single-stranded cDNA molecule templates. Optionally, in one embodiment, one or more targeted RNA molecules (or DNA molecules derived therefrom) are enriched prior to detection and quantification, as described elsewhere herein.

In one embodiment, the tumor RNA score is the quantity or count of targeted RNA molecules (or sequence reads obtained from DNA molecules derived from the targeted RNA molecules) detected. In another embodiment, the tumor RNA score comprises a mean, a mode, or an average of the total number of targeted RNA molecules (or sequence reads obtained from DNA molecules derived from the targeted RNA molecules) detected divided by the total number of genes from which RNA molecules are targeted. In still other embodiments, the tumor RNA score is determined by inputting the sequence reads into a prediction model, and the tumor RNA score output as a likelihood or probability, as described elsewhere herein.

At step 520, the presence of cancer is detected, a state of cancer determined, cancer progression monitored, and/or a cancer type determined in a subject when the tumor RNA score exceeds a threshold. The threshold value can be an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8. Alternatively, when the tumor RNA score is output from a prediction model, the output can simply be a likelihood or probability indicating the likelihood or probability that the subject has cancer, or a cancer type.

Cancer Indicator Score

Aspects of the invention are directed to computer-implemented methods for detecting the presence of a cancer in a patient. In some embodiments, the methods involve: receiving a data set in a computer comprising a processor and a computer-readable medium, wherein the data set comprises a plurality of sequence reads obtained by sequencing a plurality of nucleic acid molecules (e.g., DNA molecules) derived from a plurality of targeted ribonucleic acid (RNA) molecules in a biological test sample from the patient, and wherein the computer-readable medium comprises instructions that, when executed by the processor, cause the computer to: determine an expression level for the plurality of targeted RNA molecules from the biological test sample; comparing the expression level of each of the targeted RNA molecules to an RNA tissue score matrix to determine a cancer indicator score for each targeted RNA molecule; aggregate the cancer indicator score for each targeted RNA molecule to generate a cancer indicator score for the biological test sample; and detecting the presence of the cancer in the patient when the cancer indicator score for the biological test sample exceeds a threshold value.

In some embodiments, the target RNA molecules have an expression level in patients with a known cancer status that exceeds their expression level in healthy patients. In certain embodiments, an expression level of a target RNA molecule in a patient with a known cancer status ranges from about 2 to about 10 times greater, such as about 3, 4, 5, 6, 7, 8, or about 9 times greater, than the expression level of the target RNA molecule in a healthy patient. In certain embodiments, a target RNA molecule is not detectable in a biological test sample from a healthy patient, i.e., the target RNA molecule has an undetectable expression level.

In some embodiments, the number of target RNA molecules in the biological test sample ranges from about 1 to about 2000, from about 10 to about 1000, from about 10 to about 500, or from about 10 to about 500. In other embodiments, the number of target RNA molecules ranges from about 1 to about 50, from about 1 to about 40, from about 1 to about 30, or from about 1 to about 20, such as about 2, 3, 4, 5, 6, 7, 8, 9, 10, 11, 12, 13, 14, 15, 16, 17, 18, 19, or about 20.

In some embodiments, the cancer indicator score comprises an aggregate of the total number of targeted RNA molecules (or sequence reads obtained from DNA molecules derived from the targeted RNA molecules) detected from the biological test sample. In another embodiment, the cancer indicator score comprises a mean, a mode, or an average of the total number of targeted RNA molecules (or sequence reads obtained from DNA molecules derived from the targeted RNA molecules) detected divided by the total number of genes from which RNA molecules are targeted. In still other embodiments, the cancer indicator score is determined by inputting the sequence reads into a prediction model, and the cancer indicator score output as a likelihood or probability, as described elsewhere herein.

In some embodiments, the threshold value is an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8. In other embodiments, the threshold value ranges from about 0.5 to about 5 reads per million (RPM), such as about 1, 1.5, 2, 2.5, 3, 3.5, 4, or about 4.5 RPM. The cancer locator score threshold value can be determined based on the quantity of targeted RNA molecules (or sequence reads derived therefrom) detected in a control sample, for example a healthy subject or a subject with a known disease state. Alternatively, when the cancer locator score is output from a prediction model, the output can simply be a likelihood or probability indicating the likelihood or probability that the subject has cancer, or a cancer type.

Figure 6:
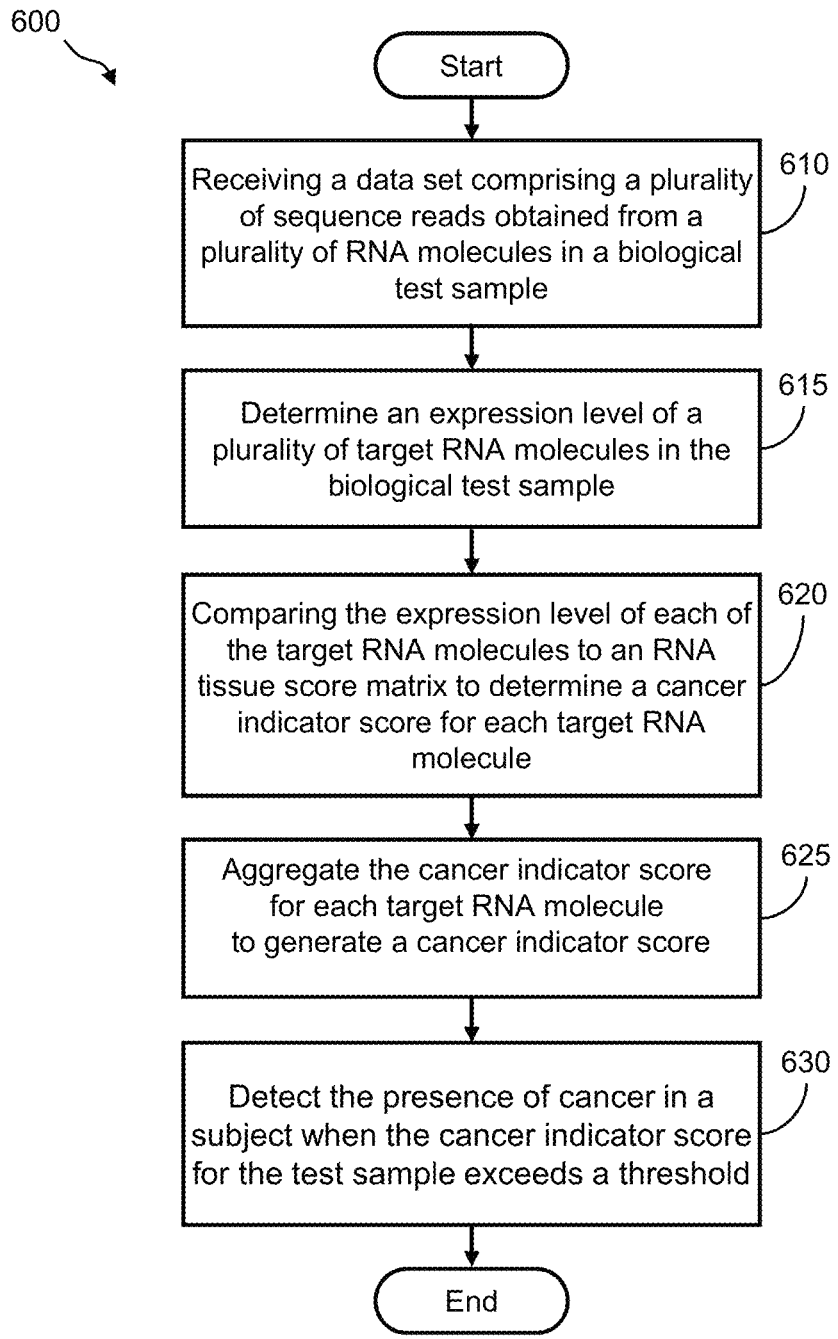
FIG. 6 is a flow diagram illustrating a method for detecting the presence of cancer in a subject based on a cancer indicator score, in accordance with one embodiment of the present invention.

FIG. 6 is a flow diagram illustrating a method for detecting the presence of cancer in a subject based on a cancer indicator score, in accordance with one embodiment of the present invention. At step 610, a data set is received comprising a plurality of sequence reads derived from a plurality of cfRNA molecules in a biological test sample. For example, a plurality of sequence reads can be determined for a plurality of cfRNA molecules extracted from a biological test sample, as described herein. Moreover, cfRNA molecules are reverse transcribed to create DNA molecules and the DNA molecules sequenced to generate sequence reads.

At step 615, an expression level is determined for a plurality of target RNA molecules in the biological test sample. For example, in one embodiment, the expression level of targeted RNA molecules can be determined based on quantification of detected sequence reads derived from a targeted RNA molecules of interest.

At step 620, the expression level of each of the target RNA molecules is compared to an RNA tissue score matrix to determine a cancer indicator score for each target RNA molecule. The RNA tissue score matrix can be determined from a training set comprising sequence reads derived from a plurality of cancer training samples with known cancer status.

At step 625, the cancer indicator scores for each target RNA molecule are aggregated to generate a cancer indicator score. In some embodiments, the cancer indicator score comprises an aggregate of the total number of targeted RNA molecules (or sequence reads obtained from DNA molecules derived from the targeted RNA molecules) detected from the biological test sample. In another embodiment, the cancer indicator score comprises a mean, a mode, or an average of the total number of targeted RNA molecules (or sequence reads obtained from DNA molecules derived from the targeted RNA molecules) detected divided by the total number of genes from which RNA molecules are targeted.

At step 630, detect the presence of cancer in a subject when the cancer indicator score for the test sample exceeds a threshold. As described above, in one embodiment, the threshold value is an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8. In other embodiments, the threshold value ranges from about 0.5 to about 5 reads per million (RPM), such as about 1, 1.5, 2, 2.5, 3, 3.5, 4, or about 4.5 RPM.

Aspects of the invention include methods for determining a cancer cell type or tissue of origin of the cancer in the patient based on the expression level of one or more of the target RNA molecules, the cancer indicator score for one or more of the target RNA molecules, the cancer indicator score for the biological test sample, or any combination thereof. In certain embodiments, the methods further involve therapeutically classifying a patient into one or more of a plurality of treatment categories based on the expression level of one or more of the target RNA molecules, the cancer indicator score for one or more of the target RNA molecules, the cancer indicator score for the biological test sample, or any combination thereof.

In certain embodiments, the computer is configured to generate a report that includes an expression level of one or more of the target RNA molecules, a cancer indicator score for one or more of the target RNA molecules, a cancer indicator score for the biological test sample, an indication of the presence or absence of the cancer in the patient, an indication of the cancer cell type of tissue of origin of the cancer in the patient, a therapeutic classification for the patient, or any combination thereof.

Liver Disease

In other aspects, the present invention is directed to methods that can be used for the assessment of NAFLD (non-alcoholic fatty liver disease) and those conditions associated with NAFLD, including fatty liver disease, alcoholic steatohepatitis (ASH), nonalcoholic steatohepatitis (NASH), fibrosis and cirrhosis through the identification of one or more signals indicative of, or informative for, NAFLD, ASH, NASH, fibrosis or cirrhosis in a test sample. In another embodiment, the methods disclosed herein can be used for the detection, screening, diagnosis, and/or monitoring of hepatocellular carcinoma (HCC). The term "NAFLD" (non-alcohol fatty liver disease) refers to a group of conditions where there is an accumulation of excess fat in the liver of people who drink little or no alcohol. The most common form of NAFLD is a condition called fatty liver disease. In fatty liver disease, fat accumulates in the liver cells. A small group of people with NAFLD may have a more serious condition termed non-alcoholic steatohepatitis (NASH). In NASH, fat accumulation is associated with liver cell inflammation and different degrees of scarring. Cirrhosis occurs when the liver sustains substantial damage, and the liver cells are gradually replaced by scar tissue which results in the inability of the liver to work properly. The use of the term "NAFLD" is used to include all conditions reflecting a form of non-alcohol fatty liver disease, including, NASH.

Figure 7:
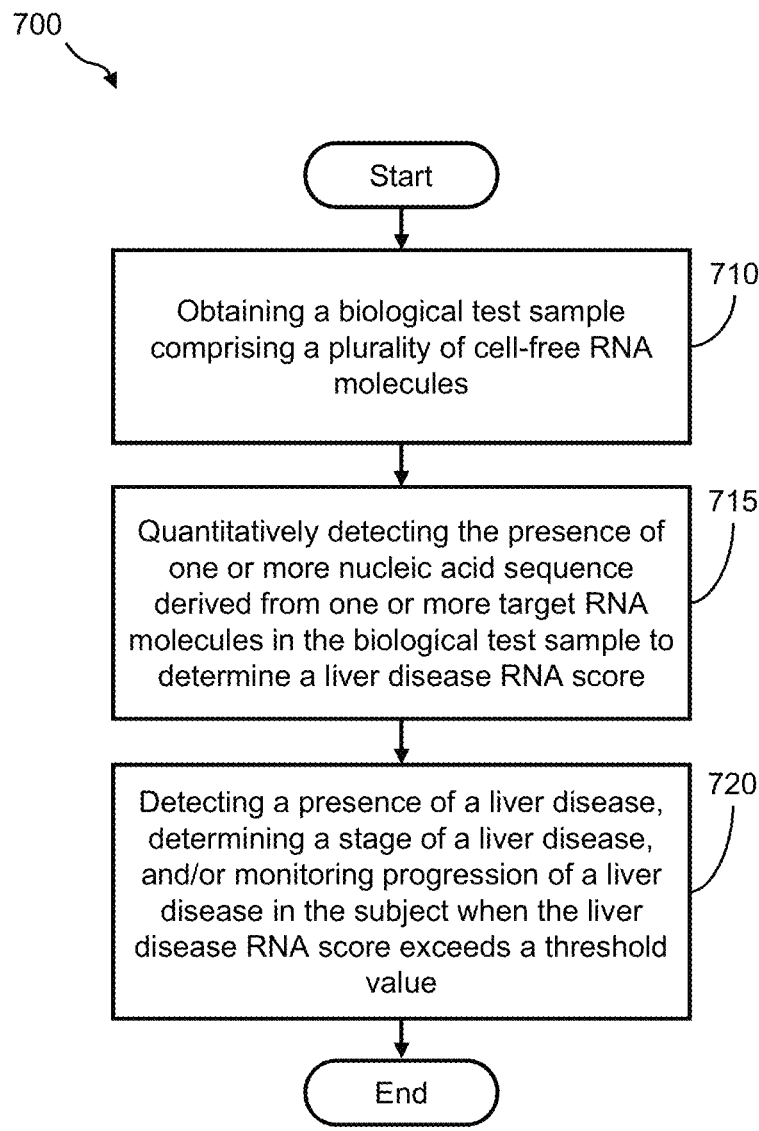
FIG. 7 is a flow diagram illustrating a method for detecting a presence of a liver disease, determining a stage of a liver disease, and/or monitoring progression of a liver disease in a subject, in accordance with one embodiment of the present invention

FIG. 7 is a flow diagram illustrating a method for detecting a presence of a liver disease, determining a stage of a liver disease, and/or monitoring progression of a liver disease in a subject, in accordance with one embodiment of the present invention. At step 710, a biological test sample comprising a plurality of cell-free RNA molecules is obtained. In one embodiment, the biological test sample is a bodily fluid (e.g., a blood, plasma, serum, urine, saliva, pleural fluid, pericardial fluid, cerebrospinal fluid (CSF), peritoneal fluid sample, or any combination thereof).

At step 715, the presence of one or more nucleic acid sequences derived from one or more target RNA molecules in the biological test sample are detected, and quantified, to determine a liver disease RNA score. As described elsewhere herein, nucleic acids derived from RNA molecules can be detected and quantified using any known means in the art. For example, in accordance with one embodiment, nucleic acids derived from RNA molecules are detected and quantified using a sequencing procedure, such as a next-generation sequencing platform (e.g., HiSeq or NovaSeq, Illumina, San Diego, Calif.). In other embodiments, nucleic acids derived from RNA molecules are detected and quantified using a microarray, reverse transcription PCR, real-time PCR, quantitative real-time PCR, digital PCR, digital droplet PCR, digital emulsion PCR, multiplex PCR, hybrid capture, oligonucleotide ligation assays, or any combination thereof. As described elsewhere, in one embodiment, cell-free nucleic acids (cfRNA molecules) can be extracted and purified using one or more known commercially available protocols or kits, such as the QIAamp circulating nucleic acid kit (Qiagen). After extraction, the cfRNA molecules are used to prepare a sequencing library. In one embodiment, a reverse transcription step is used to produce a plurality of cDNA/RNA hybrid molecules, the RNA strand degraded to produce a single-stranded cDNA molecule, a second strand synthesized to produce a plurality of double-stranded DNA molecules from the single-stranded cDNA molecule templates.

In one embodiment, the liver disease RNA score is the quantity or count of targeted RNA molecules (or sequence reads obtained from DNA molecules derived from the targeted RNA molecules) detected. In another embodiment, the liver disease RNA score comprises a mean, a mode, or an average of the total number of targeted RNA molecules (or sequence reads obtained from DNA molecules derived from the targeted RNA molecules) detected divided by the total number of genes from which RNA molecules are targeted. In still other embodiments, the liver disease RNA score is determined by inputting the sequence reads into a prediction model, and the liver disease RNA score output as a likelihood or probability, as described elsewhere herein.

At step 720, the presence of a liver disease is detected, a stage of liver disease determined, and/or liver disease progression monitored in a subject when the liver disease RNA score exceeds a threshold. The threshold value can be an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8. Alternatively, when the liver disease RNA score is output from a prediction model, the output can simply be a likelihood or probability indicating the likelihood or probability that the subject has cancer, or a cancer type.

Liver Disease Indicator Score

Aspects of the invention are directed to computer-implemented methods for detecting the presence of a liver disease in a patient. In some embodiments, the methods involve: receiving a data set in a computer comprising a processor and a computer-readable medium, wherein the data set comprises a plurality of sequence reads obtained by sequencing a plurality of ribonucleic acid (RNA) molecules in a biological test sample from the patient, and wherein the computer-readable medium comprises instructions that, when executed by the processor, cause the computer to: determine an expression level of a plurality of target RNA molecules in the biological test sample; compare the expression level of each of the target RNA molecules to an RNA tissue score matrix to determine a liver disease indicator score for each target RNA molecule; aggregate the liver disease indicator score for each target RNA molecule to generate a liver disease indicator score for the biological test sample; and detect the presence of the liver disease in the patient when the liver disease indicator score for the biological test sample exceeds a threshold value. In some embodiments, the methods involve detecting the presence or absence of, determining the stage of, monitoring the progression of a liver disease selected from the group consisting of non-alcoholic fatty liver disease (NAFLD), alcoholic steatohepatitis (ASH), nonalcoholic steatohepatitis (NASH), fibrosis and cirrhosis. In other embodiments, the methods involve detecting the presence or absence of, determining the stage of, monitoring the progression of hepatocellular carcinoma (HCC).

In some embodiments, the target RNA molecules have an expression level in patients with a known liver disease status that exceeds their expression level in healthy patients. In certain embodiments, an expression level of a target RNA molecule in a patient with a known liver disease status ranges from about 2 to about 10 times greater, such as about 3, 4, 5, 6, 7, 8, or about 9 times greater, than the expression level of the target RNA molecule in a healthy patient. In certain embodiments, a target RNA molecule is not detectable in a biological test sample from a healthy patient, i.e., the target RNA molecule has an undetectable expression level.

In some embodiments, the number of target RNA molecules in the biological test sample ranges from about 1 to about 20, such as about 2, 3, 4, 5, 6, 7, 8, 9, 10, 11, 12, 13, 14, 15, 16, 17, 18 or about 19. In other embodiments, the threshold value ranges from about 0.5 to about 5 reads per million (RPM), such as about 1, 1.5, 2, 2.5, 3, 3.5, 4, or about 4.5 RPM.

Figure 8:
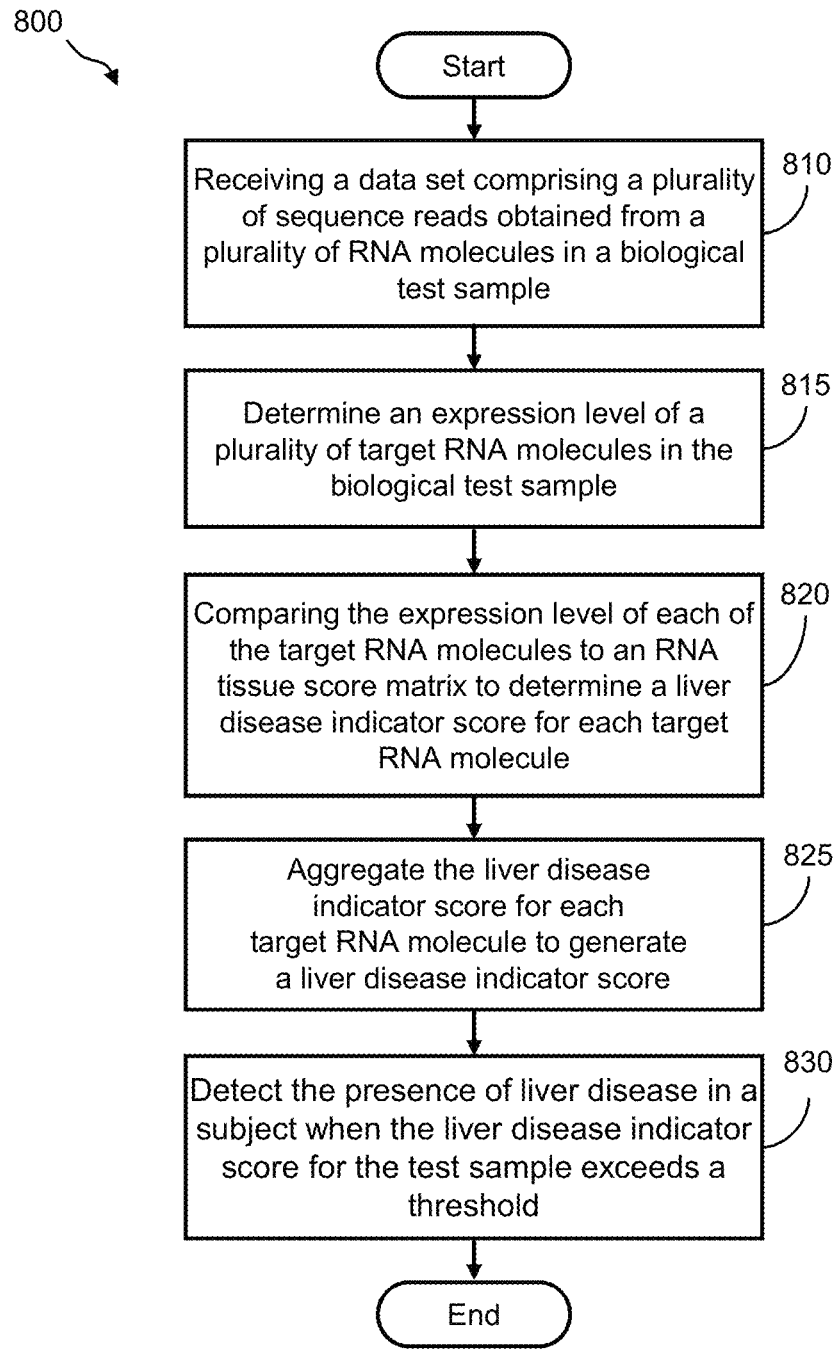
FIG. 8 is a flow diagram illustrating a method for detecting the presence of cancer in a subject based on a liver disease indicator score, in accordance with one embodiment of the present invention.
Figure 9:
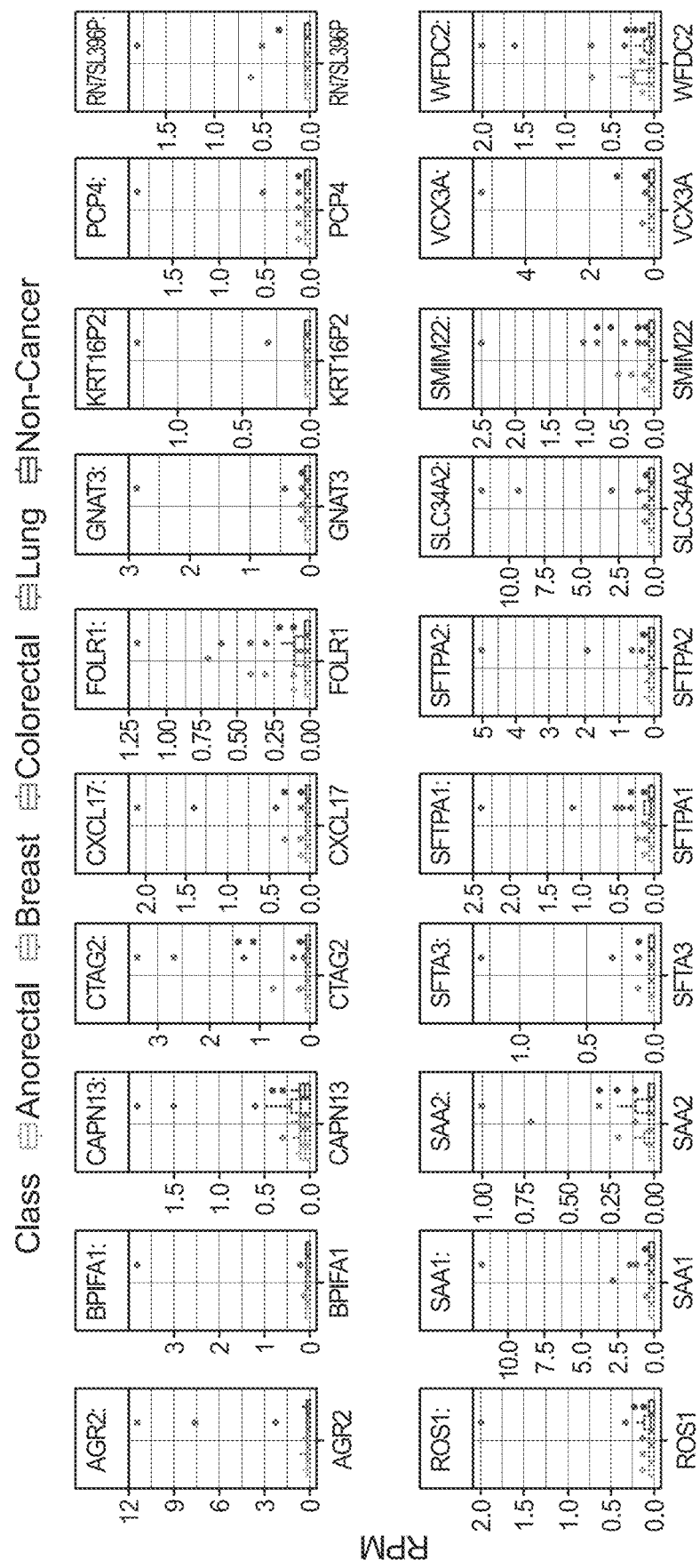
FIG. 9 depicts the expression levels of 20 dark channel genes in lung cancer with the highest expression level ratio between cancerous and non-cancerous samples. Reads per million (RPM) are plotted as a function of dark channel genes. In each plot, the columns of dots from left to right correspond to groups indicated in the top legend from left to right, respectively (class, anorectal, breast, colorectal, lung, and non-cancer).

FIG. 8 is a flow diagram illustrating a method for detecting the presence of a liver disease in a subject based on a liver disease indicator score, in accordance with one embodiment of the present invention. At step 810, a data set is received comprising a plurality of sequence reads derived from a plurality of cfRNA molecules in a biological test sample. For example, a plurality of sequence reads can be determined for a plurality of cfRNA molecules extracted from a biological test sample, as described herein.

At step 815, an expression level is determined for of a plurality of target RNA molecules in the biological test sample. For example, in one embodiment, the expression level of targeted RNA molecules can be determined based on quantification of detected sequence reads derived from a targeted RNA molecules of interest, or that align to a targeted RNA molecule of interest.

At step 820, the expression level of each of the target RNA molecules is compared to an RNA tissue score matrix to determine a liver disease indicator score for each target RNA molecule. The RNA tissue score matrix can be determined from a training set comprising sequence reads derived from a plurality of liver disease training samples with known liver disease status.

At step 825, the liver disease indicator scores for each target RNA molecule are aggregated to generate a liver disease indicator score. In some embodiments, the liver disease indicator score comprises an aggregate of the total number of targeted RNA molecules (or sequence reads obtained from DNA molecules derived from the targeted RNA molecules) detected from the biological test sample. In another embodiment, the liver disease indicator score comprises a mean, a mode, or an average of the total number of targeted RNA molecules (or sequence reads obtained from DNA molecules derived from the targeted RNA molecules) detected divided by the total number of genes from which RNA molecules are targeted. In still other embodiments, the liver disease indicator score is determined by inputting the sequence reads into a prediction model, and the liver disease indicator score output as a likelihood or probability, as described elsewhere herein.

At step 830, detect the presence of a liver disease in a subject when the liver disease indicator score for the test sample exceeds a threshold. As described above, in one embodiment, the threshold value is an integer that ranges from about 1 to about 10, such as about 2, 3, 4, 5, 6, 7, 8, or about 9. In some embodiments, the threshold is a non-integer value, ranging from about 0.1 to about 0.9, such as about 0.2, 0.3, 0.4, 0.5, 0.6, 0.7 or about 0.8. In other embodiments, the threshold value ranges from about 0.5 to about 5 reads per million (RPM), such as about 1, 1.5, 2, 2.5, 3, 3.5, 4, or about 4.5 RPM. Alternatively, when the liver disease indicator score is output from a prediction model, the output can simply be a likelihood or probability indicating the likelihood or probability that the subject has cancer, or a cancer type RNA Tissue Matrix Score Aspects of the invention include methods for constructing an RNA tissue score matrix. In some embodiments, the methods involve compiling a plurality of RNA sequence reads obtained from a plurality of patients to generate an RNA expression matrix, and normalizing the RNA expression matrix with a tissue-specific RNA expression matrix to construct the RNA tissue score matrix. In certain embodiments, the tissue-specific RNA expression matrix comprises a plurality of reference human tissues. In certain embodiments, the RNA sequence reads are obtained from a plurality of healthy patients to construct a healthy RNA tissue score matrix. In certain embodiments, the RNA sequence reads are obtained from a plurality of patients having a known cancer type to construct a cancer RNA tissue score matrix.

RNA Markers and Analysis Technique

Methods in accordance with some embodiments of the invention can be performed on cfRNA molecules and/or ctRNA molecules. In some embodiments, RNA molecules that are used in the subject methods include RNA molecules from cancerous and non-cancerous cells.

In embodiments, methods include: (a) measuring a plurality of target cell-free RNA (cfRNA) molecules in a sample of the subject, wherein the plurality of target cfRNA molecules are selected from transcripts of Tables 1-7; and (b) detecting the cancer, wherein detecting the cancer comprises detecting one or more of the target cfRNA molecules above a threshold level. In embodiments, the plurality of target cfRNA molecules are selected from at least 2, 3, 4, 5, 10, 15, 20, 25, or more transcripts of genes listed in one or more of Tables 1-7. Target cfRNA molecules can be from genes selected from any one of these tables, or any combination thereof. In embodiments, the number of tables selected from among Tables 1-7 is 2, 3, 4, 5, or all tables. In embodiments, the target cfRNA molecules that are measured are from fewer than 500 genes (e.g., fewer than 400, 300, 200, 100, or 50 genes).

In some embodiments, one or more target cfRNA molecules are derived from one or more genes selected from the genes listed in Table 1. In embodiments, the one or more target cfRNA molecules includes at least 2, 3, 4, 5, 6, 7, 8, 9, 10, 15, 20, 25, or 30 genes from Table 1. In embodiments, the one or more target cfRNA molecules includes at least 5 genes from Table 1. In embodiments, the one or more target cfRNA molecules includes at least 10 genes from Table 1. In embodiments, the one or more target cfRNA molecules includes all of the genes from Table 1. In embodiments, the one or more target cfRNA molecules includes at least one of the first 5 genes of Table 1 (AGR2, HOXC10, S100A7, BPIFA1, and IDI2-AS1), and optionally one or more additional genes from Table 1. In embodiments, the one or more target cfRNA molecules includes transcripts of the AGR2 gene. In embodiments, the one or more target cfRNA molecules includes transcripts of AGR2, HOXC10, S100A7, BPIFA1, and IDI2-AS1. In embodiments, the target cfRNA molecules that are measured are from fewer than 500 genes (e.g., fewer than 400, 300, 200, 100, or 50 genes). Table 1 below provides examples of cancer dark channel biomarkers.

TABLE 1

| | | |
|---|---|---|
| AGR2 | HOXC10 | S100A7 |
| BPIFA1 | IDI2-AS1 | SCGB2A2 |
| CASP14 | KRT16P2 | SERPINB5 |
| CSN1S1 | LALBA | SFTA3 |
| DISP2 | LINC00163 | SFTPA2 |
| EIF2D | NKX2-1 | SLC34A2 |
| FABP7 | OPN1SW | TFF1 |
| GABRG1 | PADI3 | VTCN1 |
| GNAT3 | PTPRZ1 | WFDC2 |
| GRHL2 | ROS1 | MUC5B |
| SMIM22 | CXCL17 | RNU1-1 |
| KLK5 | | |

In some embodiments, one or more target cfRNA molecules are derived from one or more genes selected from the genes listed in Table 2. In embodiments, the one or more target cfRNA molecules includes at least 2, 3, 4, 5, 6, 7, 8, 9, or 10 genes from Table 2. In embodiments, the one or more target cfRNA molecules includes at least 5 genes from Table 2. In embodiments, the one or more target cfRNA molecules includes at least 10 genes from Table 2. In embodiments, the one or more target cfRNA molecules includes all of the genes from Table 2. In embodiments, the one or more target cfRNA molecules include at least one of the first 5 genes of Table 2 (ROS1, NKX2-1, GGTLC1, SLC34A2, and SFTPA2), and optionally one or more additional genes from Table 2. In embodiments, the one or more target cfRNA molecules include transcripts of the ROS1 gene. In embodiments, the one or more target cfRNA molecules include transcripts of ROS1, NKX2-1, GGTLC1, SLC34A2, and SFTPA2. In embodiments, the target cfRNA molecules that are measured are from fewer than 500 genes (e.g., fewer than 400, 300, 200, 100, or 50 genes). Table 2 below provides examples of dark channel lung cancer biomarkers.

TABLE 2

| |
|---|
| ROS1 |
| NKX2-1 |
| GGTLC1 |
| SLC34A2 |
| SFTPA2 |
| BPIFA1 |
| SFTA3 |
| GABRG1 |
| AGR2 |
| GNAT3 |
| MUC5B |

TABLE 2-continued

SMIM22
CXCL17
WFDC2

In some embodiments, one or more target cfRNA molecules are derived from one or more genes selected from the genes listed in Table 3. In embodiments, the one or more target cfRNA molecules includes at least 2, 3, 4, 5, 6, 7, 8, 9, or 10 genes from Table 3. In embodiments, the one or more target cfRNA molecules includes at least 5 genes from Table 3. In embodiments, the one or more target cfRNA molecules includes all of the genes from Table 3. In embodiments, the one or more target cfRNA molecules include at least one of the first 5 genes of Table 3 (SCGB2A2, CSN1S1, VTCN1, FABP7, and LALBA), and optionally one or more additional genes from Table 3. In embodiments, the one or more target cfRNA molecules include transcripts of the SCGB2A2 gene. In embodiments, the one or more target cfRNA molecules include transcripts of SCGB2A2, CSN1S1, VTCN1, FABP7, and LALBA. In embodiments, the target cfRNA molecules that are measured are from fewer than 500 genes (e.g., fewer than 400, 300, 200, 100, or 50 genes). Table 3 below provides examples of breast cancer dark channel biomarkers.

TABLE 3

SCGB2A2
CSN1S1
VTCN1
FABP7
LALBA
RNU1-1
CASP14
KLK5
WFDC2
OPN1SW

In some embodiments, one or more target cfRNA molecules are derived from one or more genes selected from the genes listed in Table 4. In embodiments, the one or more target cfRNA molecules includes at least 2, 3, 4, or 5 genes from Table 4. In embodiments, the one or more target cfRNA molecules includes at least 5 genes from Table 4. In embodiments, the one or more target cfRNA molecules includes all of the genes from Table 4. In embodiments, the one or more target cfRNA molecules include at least one of the first 5 genes of Table 4 (CASP14, CRABP2, FABP7, SCGB2A2, and SERPINB5), and optionally one or more additional genes from Table 4. In embodiments, the one or more target cfRNA molecules include transcripts of the CASP14 gene. In embodiments, the one or more target cfRNA molecules include transcripts of CASP14, CRABP2, FABP7, SCGB2A2, and SERPINB5. In embodiments, the target cfRNA molecules that are measured are from fewer than 500 genes (e.g., fewer than 400, 300, 200, 100, or 50 genes). Table 4 below provides examples of breast cancer biomarkers identified using a heteroDE method, as described herein.

TABLE 4

CASP14
CRABP2
FABP7
SCGB2A2
SERPINB5

TABLE 4-continued

TRGV10
VGLL1
TFF1
AC007563.5

In some embodiments, one or more target cfRNA molecules are derived from one or more genes selected from the genes listed in Table 5. In embodiments, the one or more target cfRNA molecules includes at least 2, 3, 4, 5, 6, 7, 8, 9, 10, 15, 20, or 25 genes from Table 5. In embodiments, the one or more target cfRNA molecules includes at least 5 genes from Table 5. In embodiments, the one or more target cfRNA molecules includes at least 10 genes from Table 5. In embodiments, the one or more target cfRNA molecules includes all of the genes from Table 5. In embodiments, the one or more target cfRNA molecules include at least one of the first 5 genes of Table 5 (PTPRZ1, AGR2, SHANK1, PON1, and MYO16_AS1), and optionally one or more additional genes from Table 5. In embodiments, the one or more target cfRNA molecules include transcripts of the PTPRZ1 gene. In embodiments, the one or more target cfRNA molecules include transcripts of PTPRZ1, AGR2, SHANK1, PON1, and MYO16_AS1. In embodiments, the target cfRNA molecules that are measured are from fewer than 500 genes (e.g., fewer than 400, 300, 200, 100, or 50 genes). Table 5 below provides examples of lung cancer biomarkers identified using an information gain method, as described herein.

TABLE 5

| PTPRZ1 | AGR2 | SHANK1 |
|---|---|---|
| PON1 | MYO16_AS1 | NPAS3 |
| LINC00407 | LMO3 | KRT15 |
| ELFN2 | MUC5B | SAA2 |
| SLIT3 | NALCN | LUM |
| GDA | LINC01498 | TMEM178A |
| RCVRN | XKRX | ROS1 |
| NBPF7 | ACSM5 | SLC10A3 |
| SAA1 | CYP3A4 | LINC00643 |
| GLP1R | TRAV8_5 | GNAT3 |

In some embodiments, one or more target cfRNA molecules are derived from one or more genes selected from the genes listed in Table 6. In embodiments, the one or more target cfRNA molecules includes at least 2, 3, 4, 5, 6, 7, 8, 9, 10, 15, 20, or 25 genes from Table 6. In embodiments, the one or more target cfRNA molecules includes at least 5 genes from Table 6. In embodiments, the one or more target cfRNA molecules includes at least 10 genes from Table 6. In embodiments, the one or more target cfRNA molecules includes all of the genes from Table 6. In embodiments, the one or more target cfRNA molecules include at least one of the first 5 genes of Table 6 (ADARB2, HORMAD2, SPDYE18, RPS19, and CYP4F35P), and optionally one or more additional genes from Table 6. In embodiments, the one or more target cfRNA molecules include transcripts of the ADARB2 gene. In embodiments, the one or more target cfRNA molecules include transcripts of ADARB2, HORMAD2, SPDYE18, RPS19, and CYP4F35P. In embodiments, the target cfRNA molecules that are measured are from fewer than 500 genes (e.g., fewer than 400, 300, 200, 100, or 50 genes). Table 6 below provides examples of breast cancer biomarkers identified using an information gain method, as described herein.

TABLE 6

| | | |
|---|---|---|
| ADARB2 | HORMAD2 | SPDYE18 |
| RPS19 | CYP4F35P | MIR503HG |
| SLC34A2 | MUC5B | IGKVID_16 |
| TLX2 | IDI2 | PDPK2P |
| ACTBP2 | TTPA | LINC01140 |
| RIMKLA | WNT6 | TRBV6_4 |
| RANBP6 | FHOD3 | LINC00856 |
| CTF1 | GSTA9P | FOXC1 |
| FAM9C | SMIM2AS1 | CCDC188 |
| FAM171A2 | GRIA2 | GABRR2 |

In some embodiments, one or more target cfRNA molecules are derived from one or more genes selected from the genes listed in Table 7. In embodiments, the one or more target cfRNA molecules includes at least 2, 3, 4, 5, 6, 7, 8, 9, or 10 genes from Table 7. In embodiments, the one or more target cfRNA molecules includes at least 5 genes from Table 7. In embodiments, the one or more target cfRNA molecules includes at least 10 genes from Table 7. In embodiments, the one or more target cfRNA molecules includes all of the genes from Table 7. In embodiments, the one or more target cfRNA molecules include at least one of the first 5 genes of Table 7 (S100A7, FOXA1, BARX2, MMP7, and PLEKHG4B), and optionally one or more additional genes from Table 7. In embodiments, the one or more target cfRNA molecules include transcripts of the S100A7 gene. In embodiments, the one or more target cfRNA molecules include transcripts of S100A7, FOXA1, BARX2, MMP7, and PLEKHG4B. In embodiments, the target cfRNA molecules that are measured are from fewer than 500 genes (e.g., fewer than 400, 300, 200, 100, or 50 genes). Table 7 below provides examples of dark channel cancer biomarkers that are expressed at relatively high levels in cancer tissue.

TABLE 7

| | | |
|---|---|---|
| S100A7 | FOXA1 | BARX2 |
| MMP7 | PLEKHG4B | TFAP2A |
| TOX3 | VTCN1 | ANKRD30A |
| COL22A1 | FDCSP | LAMA1 |
| MATN3 | TFF1 | VGLL1 |

In some embodiments, one or more target cfRNA molecules are derived from one or more genes selected from Table 1 (e.g., 2, 3, 5, or more genes) in combination with (a) one or more genes selected from Table 5 or Table 6 (e.g., 2, 3, 5, or more genes), and/or (b) one or more genes selected from Table 7 (e.g., 2, 3, 5, or more genes). In embodiments, selection of genes from first and second tables comprises selecting one or more genes in both of the first and second tables. In embodiments, selection of genes from first and second tables comprises selecting one or more genes from the first table that are not in the second, and one or more genes from the second table that are not in the first.

In embodiments, one or more target cfRNA molecules are derived from one or more genes selected from Table 2 (e.g., 2, 3, 5, or more genes) in combination with (a) one or more genes selected from Table 5 (e.g., 2, 3, 5, or more genes), and/or (b) one or more genes selected from Table 7 (e.g., 2, 3, 5, or more genes). In embodiments, selection of genes from first and second tables comprises selecting one or more genes in both of the first and second tables. In embodiments, selection of genes from first and second tables comprises selecting one or more genes from the first table that are not in the second, and one or more genes from the second table that are not in the first.

In embodiments, one or more target cfRNA molecules are derived from one or more genes selected from Table 3 (e.g., 2, 3, 5, or more genes) in combination with (a) one or more genes selected from Table 4 (e.g., 2, 3, 5 or more genes), (b) one or more genes selected from Table 6 (e.g., 2, 3, 5, or more genes), and/or (c) one or more genes selected from Table 7 (e.g., 2, 3, 5, or more genes). In embodiments, selection of genes from first and second tables comprises selecting one or more genes in both of the first and second tables. In embodiments, selection of genes from first and second tables comprises selecting one or more genes from the first table that are not in the second, and one or more genes from the second table that are not in the first.

In embodiments, one or more target cfRNA molecules are derived from one or more genes selected from Table 4 (e.g., 2, 3, 5, or more genes) in combination with (a) one or more genes selected from Table 3 (e.g., 2, 3, 5, or more genes), (b) one or more genes selected from Table 6 (e.g., 2, 3, 5, or more genes), and/or (c) one or more genes selected from Table 7 (e.g., 2, 3, 5, or more genes). In embodiments, selection of genes from first and second tables comprises selecting one or more genes in both of the first and second tables. In embodiments, selection of genes from first and second tables comprises selecting one or more genes from the first table that are not in the second, and one or more genes from the second table that are not in the first.

In some embodiments, one or more target cfRNA molecules are derived from Table 8. In embodiments, the one or more target cfRNA molecules includes a plurality of genes from Table 8. In embodiments, the one or more target cfRNA molecules includes all of the genes from Table 8. In embodiments, the one or more target cfRNA molecules include transcripts of the AKR1B10 gene. In embodiments, the target cfRNA molecules that are measured are from fewer than 500 genes (e.g., fewer than 400, 300, 200, 100, or 50 genes). Table 7 below provides examples of liver disease dark channel biomarkers.

TABLE 8

| |
|---|
| AKR1B10 |
| C3 |
| PIEXO2 |

Diseases and Disorders

Methods in accordance with embodiments of the invention can be used for detecting the presence or absence of any of a variety of diseases or conditions, including, but not limited to, cardiovascular disease, liver disease, or cancer. In some embodiments, the methods involve determining a cancer stage. In some embodiments, the cancer stage is stage I cancer, stage II cancer, stage III cancer, or stage IV cancer.

In some embodiments, the methods involve detecting the presence or absence of, determining the stage of, monitoring the progression of, and/or classifying a carcinoma, a sarcoma, a myeloma, a leukemia, a lymphoma, a blastoma, a germ cell tumor, or any combination thereof. In some embodiments, the carcinoma may be an adenocarcinoma. In other embodiments, the carcinoma may be a squamous cell carcinoma. In still other embodiments, the carcinoma is selected from the group consisting of small cell lung cancer, non-small-cell lung, nasopharyngeal, colorectal, anal, liver, urinary bladder, cervical, testicular, ovarian, gastric, esophageal, head-and-neck, pancreatic, prostate, renal, thyroid, melanoma, and breast carcinoma. In some embodiments, the breast carcinoma is hormone receptor negative breast carcinoma or triple negative breast carcinoma.

In some embodiments, the methods involve detecting the presence or absence of, determining the stage of, monitoring the progression of, and/or classifying a sarcoma. In certain embodiments, the sarcoma can be selected from the group consisting of osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma. In still other embodiments, the methods involve detecting the presence or absence of, determining the stage of, monitoring the progression of, and/or classifying leukemia. In certain embodiments, the leukemia can be selected from the group consisting of: myelogenous, granulocytic, lymphatic, lymphocytic, and lymphoblastic leukemia. In still other embodiments, the methods involve detecting the presence or absence of, determining the stage of, monitoring the progression of, and/or classifying a lymphoma. In certain embodiments, the lymphoma can be selected from the group consisting of: Hodgkin's lymphoma and Non-Hodgkin's lymphoma.

Aspects of the invention include methods for determining a tissue of origin of a disease, wherein the tissue of origin is selected from the group consisting of pancreatic tissue, hepatobiliary tissue, liver tissue, lung tissue, brain tissue, neuroendocrine tissue, uterus tissue, renal tissue, urothelial tissue, renal tissue, cervical tissue, breast tissue, fat, colon tissue, rectum tissue, heart tissue, skeletal muscle tissue, prostate tissue and thyroid tissue.

Aspects of the invention include methods for determining a cancer cell type, wherein the cancer cell type is selected from the group consisting of bladder cancer, breast cancer, cervical cancer, colorectal cancer, endometrial cancer, esophageal cancer, gastric cancer, head/neck cancer, hepatobiliary cancer, hematological cancer, liver cancer, lung cancer, a lymphoma, a melanoma, multiple myeloma, ovarian cancer, pancreatic cancer, prostate cancer, renal cancer, thyroid cancer, urethral cancer and uterine cancer.

Treating Conditions

Methods disclosed herein can be used in making therapeutic decisions, guidance and monitoring, as well as development and clinical trials of cancer therapies. For example, treatment efficacy can be monitored by comparing patient cfRNA in samples from before, during, and after treatment with particular therapies such as molecular targeted therapies (monoclonal drugs), chemotherapeutic drugs, radiation protocols, etc. or combinations of these. In some embodiments, cfRNA is monitored to see if certain cancer biomarkers increase or decrease after treatment, which can allow a physician to alter a treatment (continue, stop or change treatment, for example) in a much shorter period of time than afforded by methods of monitoring that track traditional patient symptoms. In some embodiments, a method further comprises the step of diagnosing a subject based on the RNA-derived sequences, such as diagnosing the subject with a particular stage or type of cancer associated with a detected cfRNA biomarker, or reporting a likelihood that the patient has or will develop such cancer. In embodiments, methods disclosed herein further comprise selecting a treatment based on the condition detected. In embodiments, the selected treatment is administered to the subject. Where the condition is cancer, or a particular cancer type and/or stage, an appropriate anti-cancer therapy may be selected. Non-limiting examples of anti-cancer therapies include radiation therapy, surgical resection, administration of an anti-cancer agent (e.g., an immunotherapy agent, a chemotherapy agent, or the like), or a combination of one or more of these.

Classification Model

Aspects of the invention are directed to classification models. For example, a machine learning or deep learning model (e.g., a disease classifier) can be used to determine a disease state based on values of one or more features determined from one or more RNA molecules or sequence reads (derived from one or more cfRNA molecules). In various embodiments, the output of the machine learning or deep learning model is a predictive score or probability of a disease state (e.g., a predictive cancer score). Therefore, the machine learning or deep learning model generates a disease state classification based on the predictive score or probability.

In some embodiments, the machine learned model includes a logistic regression classifier. In other embodiments, the machine learning or deep learning model can be one of a decision tree, an ensemble (e.g., bagging, boosting, random forest), gradient boosting machine, ion, Naïve Bayes, support vector machine, or a neural network. The disease state model includes learned weights for the features that are adjusted during training. The term weights is used generically here to represent the learned quantity associated with any given feature of a model, regardless of which particular machine learning technique is used. In some embodiments, a cancer indicator score is determined by inputting values for features derived from one or more RNA sequences (or DNA sequence reads thereof) into a machine learning or deep learning model. In other embodiments, a liver disease indicator score is determined by inputting values for features derived from one or more RNA sequences (or DNA sequence reads thereof) into a machine learning or deep learning model.

During training, training data is processed to generate values for features that are used to train the weights of the disease state model. As an example, training data can include cfRNA data and/or WBC RNA data obtained from training samples, as well as an output label. For example, the output label can be indication as to whether the individual is known to have a specific disease (e.g., known to have cancer) or known to be healthy (i.e., devoid of a disease). In other embodiments, the model can be used to determine a disease type, or tissue of origin (e.g., cancer tissue of origin), or an indication of a severity of the disease (e.g., cancer stage) and generate an output label therefor. Depending on the particular embodiment, the disease state model receives the values for one or more of the features determine from an RNA assay used for detection and quantification of a cfRNA molecule or sequence derived therefrom, and computational analyses relevant to the model to be trained. In one embodiment, the one or more features comprise a quantity of one or more cfRNA molecules or sequence reads derived therefrom. Depending on the differences between the scores output by the model-in-training and the output labels of the training data, the weights of the predictive cancer model are optimized to enable the disease state model to make more accurate predictions. In various embodiments, a disease state model may be a non-parametric model (e.g., k-nearest neighbors) and therefore, the predictive cancer model can be trained to make more accurately make predictions without having to optimize parameters.

The trained disease state model can be stored in a computer readable medium, and subsequently retrieved when needed, for example, during deployment of the model.

Figure 10:
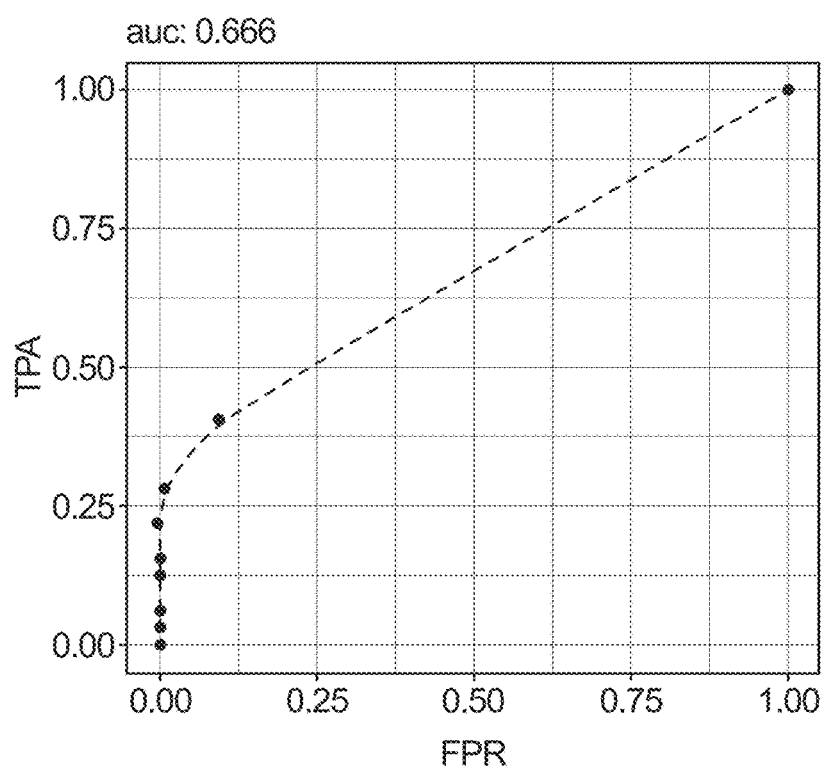
FIG. 10 is a ROC curve of the decision tree classifier using a tissue score aggregated from dark channel genes.

In some embodiments, the methods involve transforming a gene expression matrix (G) into a tissue score matrix (S) by multiplying the gene expression matrix (G) with a tissue specificity matrix (TS). $G_{m,n}$ is the expression level for gene n in sample m. $TS_{n,j}$ is the tissue specificity of gene n for tissue j. If gene n is not specific for tissue j, $TS_{n,j}=0$. In some embodiments, the tissue specificity matrix is calculated using the tissue RNA-seq database (GTEx). The tissue scores can be used as features to build models to classify, e.g., cancer versus non-cancer samples. In one non-limiting embodiment, the dark channel genes identified from lung cancer samples (SFTPA2, SLC39A4, NKX2_1, SFTPA1, BPIFA1, SLC34A2, CXCL17, SFTA3, MUC1, AGR2, WFDC2, ABCA12, VSIG10, CRABP2) were used to build a decision tree classifier to distinguish lung cancer from non-cancer cfRNA samples. The results of this analysis are shown in FIG. 10.

Sequencing and Bioinformatics

Aspects of the invention include sequencing of nucleic acid molecules to generate a plurality of sequence reads, and bioinformatic manipulation of the sequence reads to carry out the subject methods.

In certain embodiments, a sample is collected from a subject, followed by enrichment for genetic regions or genetic fragments of interest. For example, in some embodiments, a sample can be enriched by hybridization to a nucleotide array comprising cancer-related genes or gene fragments of interest. In some embodiments, a sample can be enriched for genes of interest (e.g., cancer-associated genes) using other methods known in the art, such as hybrid capture. See, e.g., Lapidus (U.S. Pat. No. 7,666,593), the contents of which is incorporated by reference herein in its entirety. In one hybrid capture method, a solution-based hybridization method is used that includes the use of biotinylated oligonucleotides and streptavidin coated magnetic beads. See, e.g., Duncavage et al., J Mol Diagn. 13(3): 325-333 (2011); and Newman et al., Nat Med. 20(5): 548-554 (2014). Isolation of nucleic acid from a sample in accordance with the methods of the invention can be done according to any method known in the art.

Sequencing may be by any method or combination of methods known in the art. For example, known nucleic acid sequencing techniques include, but are not limited to, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, Polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977), the contents of which are incorporated by reference herein in their entirety. Another conventional sequencing method involves chemical degradation of nucleic acid fragments. See, Maxam et al., Proc. Natl. Acad. Sci., 74: 560 564 (1977), the contents of which are incorporated by reference herein in their entirety. Methods have also been developed based upon sequencing by hybridization. See, e.g., Harris et al., (U.S. patent application number 2009/0156412), the contents of which are incorporated by reference herein in their entirety.

A sequencing technique that can be used in the methods of the provided invention includes, for example, Helicos True Single Molecule Sequencing (tSMS) (Harris T. D. et al. (2008) Science 320:106-109), the contents of which are incorporated by reference herein in their entirety. Further description of tSMS is shown, for example, in Lapidus et al. (U.S. Pat. No. 7,169,560), the contents of which are incorporated by reference herein in their entirety, Lapidus et al. (U.S. patent application publication number 2009/0191565, the contents of which are incorporated by reference herein in their entirety), Quake et al. (U.S. Pat. No. 6,818,395, the contents of which are incorporated by reference herein in their entirety), Harris (U.S. Pat. No. 7,282,337, the contents of which are incorporated by reference herein in their entirety), Quake et al. (U.S. patent application publication number 2002/0164629, the contents of which are incorporated by reference herein in their entirety), and Braslaysky, et al., PNAS (USA), 100: 3960-3964 (2003), the contents of which are incorporated by reference herein in their entirety.

Another example of a nucleic acid sequencing technique that can be used in the methods of the provided invention is 454 sequencing (Roche) (Margulies, M et al. 2005, Nature, 437, 376-380, the contents of which are incorporated by reference herein in their entirety). Another example of a DNA sequencing technique that can be used in the methods of the provided invention is SOLiD technology (Applied Biosystems). Another example of a DNA sequencing technique that can be used in the methods of the provided invention is Ion Torrent sequencing (U.S. patent application publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the contents of each of which are incorporated by reference herein in their entirety).

In some embodiments, the sequencing technology is Illumina sequencing. Illumina sequencing is based on the amplification of DNA on a solid surface using fold-back PCR and anchored primers. Genomic DNA can be fragmented, or in the case of cfDNA, fragmentation is not needed due to the already short fragments. Adapters are ligated to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. Yet another example of a sequencing technique that can be used in the methods of the provided invention is nanopore sequencing (Soni G V and Meller A. (2007) Clin Chem 53: 1996-2001, the contents of which are incorporated by reference herein in their entirety). Another example of a sequencing technique that can be used in the methods of the provided invention involves using a chemical-sensitive field effect transistor (chemFET) array to sequence DNA (for example, as described in US Patent Application Publication No. 20090026082, the contents of which are incorporated by reference herein in their entirety). Another example of a sequencing technique that can be used in the methods of the provided invention involves using an electron microscope (Moudrianakis E. N. and Beer M. Proc Natl Acad Sci USA. 1965 March; 53:564-71, the contents of which are incorporated by reference herein in their entirety).

If the nucleic acid from the sample is degraded or only a minimal amount of nucleic acid can be obtained from the sample, PCR can be performed on the nucleic acid in order to obtain a sufficient amount of nucleic acid for sequencing (See, e.g., Mullis et al. U.S. Pat. No. 4,683,195, the contents of which are incorporated by reference herein in its entirety)

Computer Systems and Devices

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy subjects, and a fourth database can contain data from sick subjects with a known condition or disorder. It is to be understood that any other configuration of databases with respect to the data contained therein is also contemplated by the methods described herein.

EXEMPLARY EMBODIMENTS (A)

The present description provides the following embodiments, with some embodiments of this paragraph referring to other numbered embodiments of this paragraph:

1. A method for detecting a disease state in a subject, the method comprising:

isolating a biological test sample from the subject, wherein the biological test sample comprises a plurality of cell-free ribonucleic acid (cfRNA) molecules;

extracting the plurality of cfRNA molecules from the biological test sample;

performing a sequencing procedure on the extracted cfRNA molecules to generate a plurality of sequence reads;

performing a filtering procedure to generate an excluded population of sequence reads that originate from one or more healthy cells, and a non-excluded population of sequence reads;

performing a quantification procedure on one or more of the non-excluded sequence reads; and detecting the disease state in the subject when one or more of the non-excluded sequence reads exceeds a threshold.

2. The method of embodiment 1, further comprising quantifying the cfRNA molecules that are extracted from the biological test sample.

3. The method of embodiment 1, wherein the sequencing procedure comprises:

performing a reverse transcription procedure on the cfRNA molecules to produce a plurality of cDNA/RNA hybrid molecules;

degrading the RNA of the hybrid molecules to produce a plurality of single-stranded cDNA molecule templates;

synthesizing a plurality of double-stranded DNA molecules from the single-stranded cDNA molecule templates;

ligating a plurality of double-stranded DNA adapters to the plurality of double-stranded DNA molecules, thereby producing a sequencing library; and performing a sequencing procedure on at least a portion of the sequencing library to obtain a plurality of sequence reads.

4. The method of embodiment 3, wherein synthesizing the double-stranded DNA molecules comprises performing a strand-displacement reverse transcriptase procedure.

5. The method of embodiment 3, wherein the sequencing procedure comprises a whole transcriptome sequencing procedure.

6. The method of embodiment 3, wherein the sequencing procedure comprises a targeted sequencing procedure, and wherein one or more of the cfRNA molecules are enriched from the biological test sample before preparing the sequencing library.

7. The method of embodiment 6, wherein one or more cfRNA molecules indicative of the disease state are targeted for enrichment.

8. The method according to embodiment 7, wherein the targeted cfRNA molecules are derived from a gene selected from the group consisting of AGR2, BPIFA1, CASP14, CSN1S1, DISP2, EIF2D, FABP7, GABRG1, GNAT3, GRHL2, HOXC10, IDI2-AS1, KRT16P2, LALBA, LINC00163, NKX2-1, OPN1SW, PADI3, PTPRZ1, ROS1, S100A7, SCGB2A2, SERPINB5, SFTA3, SFTPA2, SLC34A2, TFF1, VTCN1, WFDC2, MUCSB, SMIM22, CXCL17, RNU1-1, and KLK5.

9. The method according to embodiment 7, wherein the targeted cfRNA molecules are derived from a gene selected from the group consisting of ROS1, NKX2, GGTLC1, SLC34A2, SFTPA2, BPIFA1, SFTA3, GABRG1, AGR2, GNAT3, MUCSB, SMIM22, CXCL17, and WFDC2.

10. The method according to embodiment 7, wherein the targeted cfRNA molecules are derived from a gene selected from the group consisting of SCGB2A2, CSN1S1, VTCN-1, FABP7, LALBA, RNU1-1, OPN1SW, CASP14, KLK5, and WFDC2.

11. The method according to embodiment 7, wherein the targeted cfRNA molecules are derived from the AKR1B10, C3, and/or PIEZO2 genes.

12. The method of embodiment 1, wherein the plurality of cfRNA molecules comprises one or more dark channel cfRNA molecules.

13. The method of embodiment 1, wherein the filtering procedure comprises:

comparing each sequence read from the cfRNA molecules extracted from the biological test sample to a control data set of RNA sequences;

identifying one or more sequence reads that match one or more sequence reads in the control data set of RNA sequences; and placing each sequence read that matches one or more sequence reads in the control data set of RNA sequences in the excluded population of sequence reads.

14. The method of embodiment 13, wherein the control data set of RNA sequences comprises a plurality of sequence reads obtained from one or more healthy subjects.

15. The method of embodiment 13, wherein the control data set of RNA sequences comprises a plurality of sequence reads obtained from a plurality of blood cells from the subject.

16. The method of embodiment 15, wherein the blood cells comprise white blood cells (WBCs).

17. The method of any one of embodiments 1-16, wherein the disease state is a cardiovascular disease state.

18. The method of any one of embodiments 1-16, wherein the disease state is a liver disease state.

19. The method of any one of embodiments 1-16, wherein the disease state is a cancerous disease state.

20. The method of embodiment 19, wherein the cancerous disease state comprises a carcinoma, a sarcoma, a myeloma, a leukemia, a lymphoma, a blastoma, a germ cell tumor, or any combination thereof.

21. The method of embodiment 20, wherein the carcinoma is an adenocarcinoma.

22. The method of embodiment 20, wherein the carcinoma is a squamous cell carcinoma.

23. The method of embodiment 20, wherein the carcinoma is selected from the group consisting of: small cell lung cancer, non-small-cell lung, nasopharyngeal, colorectal, anal, liver, urinary bladder, testicular, cervical, ovarian, gastric, esophageal, head-and-neck, pancreatic, prostate, renal, thyroid, melanoma, and breast carcinoma.

24. The method of embodiment 23, wherein the breast carcinoma is hormone receptor negative breast carcinoma or triple negative breast carcinoma.

25. The method of embodiment 20, wherein the sarcoma is selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma.

26. The method of embodiment 20, wherein the leukemia is selected from the group consisting of: myelogenous, granulocytic, lymphatic, lymphocytic, and lymphoblastic leukemia.

27. The method of embodiment 20, wherein the lymphoma is selected from the group consisting of: Hodgkin's lymphoma and Non-Hodgkin's lymphoma.

28. The method of embodiment 1, further comprising determining a tissue of origin of the disease, wherein the tissue of origin is selected from the group consisting of pancreatic tissue, liver issue, lung tissue, brain tissue, uterus tissue, renal tissue, breast tissue, fat, colon tissue, rectum tissue, heart tissue, skeletal muscle tissue, prostate tissue and thyroid tissue.

29. The method of embodiment 1, wherein the biological test sample comprises a biological fluid.

30. The method of embodiment 29, wherein the biological fluid comprises: blood, plasma, serum, urine, saliva, pleural fluid, pericardial fluid, cerebrospinal fluid (CSF), peritoneal fluid, or any combination thereof.

31. The method of embodiment 1, wherein the disease state is determined by inputting the sequence reads into a machine learning or deep learning model.

32. The method of embodiment 31, wherein the machine learning or deep learning model comprises logistic regression, random forest, gradient boosting machine, Naïve Bayes, neural network, or multinomial regression.

33. The method of embodiment 31, wherein the method further comprises:

performing or having performed a computational analysis on the non-excluded sequence reads to generate values of one or more features, wherein the features comprise a quantity of the one or more non-excluded sequence reads;

inputting the values of the one or more features into the machine learning or deep learning model to generate a disease state prediction for the subject, and wherein the machine learning or deep learning model transforms the values of the one or more features to the disease state prediction for the subject through a function comprising learned weights; and providing the disease state prediction for the subject.

34. A computer-implemented method for identifying one or more RNA sequences indicative of a disease state, the method comprising:

obtaining, by a computer system, a first set of sequence reads from a plurality of RNA molecules from a first test sample from a subject known to have the disease, wherein the first test sample comprises a plurality of cell-free RNA (cfRNA) molecules;

obtaining, by a computer system, a second set of sequence reads from a plurality of RNA molecules from a control sample;

detecting, by a computer system, one or more RNA sequences that are present in the first set of sequence reads, and that are not present in the second set of sequence reads, to identify one or more RNA sequences that are indicative of the disease state.

35. The method of embodiment 34, wherein the control sample comprises a plurality of RNA molecules from one or more healthy subjects.

36. The method of embodiment 35, wherein the second set of sequence reads comprises RNA sequence information obtained from a public database.

37. The method of embodiment 36, wherein the control sample comprises a plurality of RNA molecules from a plurality of blood cells from the subject.

38. The method of any one of embodiments 34-37, wherein the first test sample comprises: blood, plasma, serum, urine, saliva, pleural fluid, pericardial fluid, cerebrospinal fluid (CSF), peritoneal fluid, or any combination thereof.

39. The method of embodiment 38, wherein the first test sample comprises plasma.

40. The method of any one of embodiment 37, wherein the blood cells comprise white blood cells.

41. The method of any one of embodiments 34-37, wherein the disease state is a cardiovascular disease state.

42. The method of any one of embodiments 34-37, wherein the disease state is a liver disease state.

43. The method of any one of embodiments 34-37, wherein the disease state is a cancerous disease state.

44. The method of embodiment 36, wherein the cancerous disease state comprises a carcinoma, a sarcoma, a myeloma, a leukemia, a lymphoma, a blastoma, a germ cell tumor, or any combination thereof.

45. The method of embodiment 44, wherein the carcinoma is an adenocarcinoma.

46. The method of embodiment 44, wherein the carcinoma is a squamous cell carcinoma.

47. The method of embodiment 44, wherein the carcinoma is selected from the group consisting of: small cell lung cancer, non-small-cell lung, nasopharyngeal, colorectal, anal, liver, urinary bladder, testicular, cervical, ovarian, gastric, esophageal, head-and-neck, pancreatic, prostate, renal, thyroid, melanoma, and breast carcinoma.

48. The method of embodiment 47, wherein the breast carcinoma is hormone receptor negative breast carcinoma or triple negative breast carcinoma.

49. The method of embodiment 44, wherein the sarcoma is selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma.

50. The method of embodiment 44, wherein the leukemia is selected from the group consisting of: myelogenous, granulocytic, lymphatic, lymphocytic, and lymphoblastic leukemia.

51. The method of embodiment 44, wherein the lymphoma is selected from the group consisting of: Hodgkin's lymphoma and Non-Hodgkin's lymphoma.

52. The method of embodiment 34, wherein the disease state is determined by inputting the one or more RNA sequences into a machine learning or deep learning model.

53. The method of embodiment 52, wherein the machine learning or deep learning model comprises logistic regression, random forest, gradient boosting machine, Naïve Bayes, neural network, or multinomial regression.

54. The method of embodiment 52, wherein the method further comprises:

performing or having performed a computational analysis on the one or more RNA sequences to generate values of one or more features, wherein the features comprise a quantity of the one or more RNA sequences;

inputting the values of the one or more features into the machine learning or deep learning model to generate a disease state prediction for the subject, and wherein the machine learning or deep learning model transforms the values of the one or more features to the disease state prediction for the subject through a function comprising learned weights; and providing the disease state prediction for the subject.

55. A computer-implemented method for detecting one or more tumor-derived RNA molecules in a subject, the method comprising:

obtaining, by a computer system, a first set of sequence reads from a plurality of RNA molecules from a first test sample from a subject known to have a tumor, wherein the first test sample comprises a plurality of cell-free RNA (cfRNA) molecules;

obtaining, by a computer system, a second set of sequence reads from a plurality of RNA molecules from a plurality of blood cells from the subject; and detecting, by a computer system, one or more RNA sequences that are present in the first set of sequence reads, and that are not present in the second set of sequence reads, to detect the one or more tumor-derived RNA molecules in the subject.

56. The method of embodiment 55, wherein the plurality of blood cells comprise white blood cells.

57. The method of embodiment 55, wherein the first test sample comprises: blood, plasma, serum, urine, saliva, pleural fluid, pericardial fluid, cerebrospinal fluid (CSF), peritoneal fluid, or any combination thereof.

58. The method of embodiment 55, wherein the first test sample comprises plasma.

59. The method of embodiment 55, wherein the tumor comprises a carcinoma, a sarcoma, a myeloma, a leukemia, a lymphoma, a blastoma, a germ cell tumor, or any combination thereof.

60. The method of embodiment 59, wherein the carcinoma is an adenocarcinoma.

61. The method of embodiment 59, wherein the carcinoma is a squamous cell carcinoma.

62. The method of embodiment 59, wherein the carcinoma is selected from the group consisting of: small cell lung cancer, non-small-cell lung, nasopharyngeal, colorectal, anal, liver, urinary bladder, testicular, cervical, ovarian, gastric, esophageal, head-and-neck, pancreatic, prostate, renal, thyroid, melanoma, and breast carcinoma.

63. The method of embodiment 62, wherein the breast carcinoma is hormone receptor negative breast carcinoma or triple negative breast carcinoma.

64. The method of embodiment 59, wherein the sarcoma is selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma.

65. The method of embodiment 59, wherein the leukemia is selected from the group consisting of: myelogenous, granulocytic, lymphatic, lymphocytic, and lymphoblastic leukemia.

66. The method of embodiment 59, wherein the lymphoma is selected from the group consisting of: Hodgkin's lymphoma and Non-Hodgkin's lymphoma.

67. The method of embodiment 55, wherein the method further comprises determining cancer status of the subject, wherein determining the cancer status is determined by inputting the one or more tumor-derived RNA molecules into a machine learning or deep learning model.

68. The method of embodiment 67, wherein the machine learning or deep learning model comprises logistic regression, random forest, gradient boosting machine, Naïve Bayes, neural network, or multinomial regression.

69. The method of embodiment 67, wherein the method further comprises:
 performing or having performed a computational analysis on the one or more tumor-derived RNA molecules to generate values of one or more features, wherein the features comprise a quantity of the one or more tumor-derived RNA molecules;
 inputting the values of the one or more features into the machine learning or deep learning model to generate a disease state prediction for the subject, and wherein the machine learning or deep learning model transforms the values of the one or more features to the disease state prediction for the subject through a function comprising learned weights; and
 providing the cancer status for the subject.

70. A method for detecting a presence of a cancer, determining a cancer stage, monitoring a cancer progression, and/or determining a cancer type in a subject known to have or suspected of having a cancer, the method comprising:
 (a) obtaining a biological test sample from the subject, wherein the biological test sample comprises a plurality of cell-free ribonucleic acid (cfRNA) molecules;
 (b) quantitatively detecting the presence of one or more nucleic acid sequences derived from one or more target RNA molecules in the biological test sample to determine a tumor RNA score, wherein the one or more target RNA molecules are selected from the target RNA molecules listed on any one of Tables 1-3; and
 (c) detecting the presence of the cancer, determining the cancer stage, monitoring the cancer progression, and/or determining the cancer type in the subject when the tumor RNA score exceeds a threshold value.

71. The method of embodiment 70, wherein quantitatively detecting the presence of the sequences derived from the RNA markers comprises conducting a sequencing procedure.

72. The method of embodiment 71, wherein the sequencing procedure comprises whole transcriptome sequencing of the cfRNA molecules in the biological test sample.

73. The method of embodiment 70, wherein quantitatively detecting the presence of the sequences derived from the target RNA molecules comprises sequencing, NGS sequencing, Sanger sequencing, microarray analysis, reverse transcription PCR, real-time PCR, quantitative real-time PCR, digital PCR, digital droplet PCR, digital emulsion PCR, multiplex PCR, hybrid capture, oligonucleotide ligation assays, or any combination thereof.

74. The method of embodiment 70, wherein quantitatively detecting the presence of the sequences derived from the target RNA molecules comprises microarray analysis.

75. The method of embodiment 71, further comprising enriching the cfRNA molecules in the biological test sample for one or more RNA markers prior to quantitatively detecting the presence of a sequence read derived from one or more target RNA molecules.

76. The method of embodiment 70, wherein the cancer comprises a carcinoma, a sarcoma, a myeloma, a leukemia, a lymphoma, a blastoma, a germ cell tumor, or any combination thereof.

77. The method of embodiment 76, wherein the carcinoma is an adenocarcinoma.

78. The method of embodiment 76, wherein the carcinoma is a squamous cell carcinoma.

79. The method of embodiment 76, wherein the carcinoma is selected from the group consisting of: small cell lung cancer, non-small-cell lung, nasopharyngeal, colorectal, anal, liver, urinary bladder, testicular, cervical, ovarian, gastric, esophageal, head-and-neck, pancreatic, prostate, renal, thyroid, melanoma, and breast carcinoma.

80. The method of embodiment 79, wherein the breast carcinoma is hormone receptor negative breast carcinoma or triple negative breast carcinoma.

81. The method of embodiment 79, wherein the sarcoma is selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma.

82. The method of embodiment 76, wherein the leukemia is selected from the group consisting of: myelogenous, granulocytic, lymphatic, lymphocytic, and lymphoblastic leukemia.

83. The method of embodiment 76, wherein the lymphoma is selected from the group consisting of: Hodgkin's lymphoma and Non-Hodgkin's lymphoma.

84. The method of embodiment 70 wherein the cancer stage is selected from stage I cancer, stage II cancer, stage III cancer, and stage IV cancer.

85. The method of embodiment 70, wherein the tumor RNA score is determined by inputting the sequence reads into a machine learning or deep learning model.

86. The method of embodiment 85, wherein the machine learning or deep learning model comprises logistic regression, random forest, gradient boosting machine, Naïve Bayes, neural network, or multinomial regression.

87. The method of embodiment 85, wherein the method further comprises:

performing or having performed a computational analysis on the one or more target RNA molecules to generate values of one or more features, wherein the features comprise a quantity of the one or more target RNA molecules;

inputting the values of the one or more features into the machine learning or deep learning model to generate a cancer prediction for the subject, the cancer prediction comprising detecting a presence of a cancer, determining a cancer stage, monitoring a cancer progression, and/or determining a cancer type, and wherein the machine learning or deep learning model transforms the values of the one or more features to the cancer prediction for the subject through a function comprising learned weights; and providing the cancer prediction for the subject.

88. The method of embodiment 70, wherein the one or more target RNA molecules comprise one or more of the markers listed on Table 1.

89. The method of embodiment 70, wherein the one or more target RNA molecules comprise one or more of the markers listed on Table 2.

90. The method of embodiment 70, wherein the one or more target RNA molecules include one or more of the markers listed on Table 3.

91. A computer-implemented method for detecting the presence of a cancer in a subject, the method comprising:

receiving a data set in a computer comprising a processor and a computer-readable medium, wherein the data set comprises a plurality of sequence reads obtained from a plurality of ribonucleic acid (RNA) molecules in a biological test sample from the subject, and wherein the computer-readable medium comprises instructions that, when executed by the processor, cause the computer to:

determine an expression level of a plurality of target RNA molecules in the biological test sample;

compare the expression level of each of the target RNA molecules to an RNA tissue score matrix to determine a cancer indicator score for each target RNA molecule;

aggregate the cancer indicator score for each target RNA molecule to generate a cancer indicator score for the biological test sample; and detect the presence of the cancer in the subject when the cancer indicator score for the biological test sample exceeds a threshold value.

92. The method according to embodiment 91, wherein the target RNA molecules have an expression level in subjects with a known cancer status that exceeds their expression level in healthy subjects.

93. The method according to embodiment 91, wherein the expression level of a target RNA molecule in a subject with a known cancer status is at least 10 times greater than the expression level of the target RNA molecule in a healthy subject.

94. The method according to embodiment 91, wherein the target RNA molecules are not detectable in a biological test sample from a healthy subject.

95. The method according to embodiment 91, wherein the number of target RNA molecules ranges from 1 to 20.

96. The method according to embodiment 91, wherein the threshold value ranges from 0.5 to 5 reads per million (RPM).

97. The method according to embodiment 91, further comprising determining a cancer cell type or tissue of origin of the cancer in the subject based on the expression level of one or more of the target RNA molecules, the cancer indicator score for one or more of the target RNA molecules, the cancer indicator score for the biological test sample, or any combination thereof.

98. The method according to embodiment 91, further comprising therapeutically classifying the subject into one or more of a plurality of treatment categories based on the expression level of one or more of the target RNA molecules, the cancer indicator score for one or more of the target RNA molecules, the cancer indicator score for the biological test sample, or any combination thereof.

99. The method according to any one of the preceding embodiments, wherein the computer is configured to generate a report that comprises: an expression level of one or more of the target RNA molecules, a cancer indicator score for one or more of the target RNA molecules, a cancer indicator score for the biological test sample, an indication of the presence or absence of the cancer in the subject, an indication of the cancer cell type of tissue of origin of the cancer in the subject, a therapeutic classification for the subject, or any combination thereof.

100. The method according to any one of the preceding embodiments, wherein the plurality of RNA molecules comprise cell-free RNA (cfRNA) molecules.

101. The method according to any one of the preceding embodiments, wherein the plurality of RNA molecules comprise circulating tumor RNA (ctRNA) molecules.

102. The method of any one of the preceding embodiments, wherein the plurality of RNA molecules in the biological test sample comprise RNA from cancerous and non-cancerous cells.

103. The method according to any one of the preceding embodiments, wherein the biological test sample comprises a biological fluid.

104. The method according to embodiment 103, wherein the biological fluid comprises blood, plasma, serum, urine, saliva, pleural fluid, pericardial fluid, cerebrospinal fluid (CSF), peritoneal fluid, or any combination thereof.

105. The method according to any one of embodiments 91-103, wherein the biological test sample comprises a tissue biopsy.

106. The method according to embodiment 105, wherein the tissue biopsy is a cancerous tissue biopsy.

107. The method according to embodiment 105, wherein the tissue biopsy is a healthy tissue biopsy.

108. The method according to any one of the preceding embodiments, wherein the cancer comprises a carcinoma, a sarcoma, a myeloma, a leukemia, a lymphoma, a blastoma, a germ cell tumor, or any combination thereof.

109. The method according to embodiment 108, wherein the carcinoma is an adenocarcinoma.

110. The method according to embodiment 108, wherein the carcinoma is a squamous cell carcinoma.

111. The method according to embodiment 108, wherein the carcinoma is selected from the group consisting of: small cell lung cancer, non-small-cell lung, nasopharyngeal, colorectal, anal, liver, urinary bladder, testicular, cervical, ovarian, gastric, esophageal, head-and-neck, pancreatic, prostate, renal, thyroid, melanoma, and breast carcinoma.

112. The method according to embodiment 108, wherein the breast cancer is hormone receptor negative breast cancer or triple negative breast cancer.

113. The method according to embodiment 108, wherein the sarcoma is selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma.

114. The method according to embodiment 108, wherein the leukemia is selected from the group consisting of: myelogenous, granulocytic, lymphatic, lymphocytic, and lymphoblastic leukemia.

115. The method according to embodiment 108, wherein the lymphoma is selected from the group consisting of: Hodgkin's lymphoma and Non-Hodgkin's lymphoma.

116. A method for constructing an RNA tissue score matrix, the method comprising:
compiling a plurality of RNA sequence reads obtained from a plurality of subjects to generate an RNA expression matrix; and
normalizing the RNA expression matrix with a tissue-specific RNA expression matrix to construct the RNA tissue score matrix.

117. The method according to embodiment 116, wherein the tissue-specific RNA expression matrix comprises a plurality of reference human tissues.

118. The method according to embodiment 116, wherein the RNA sequence reads are obtained from a plurality of healthy subjects to construct a healthy RNA tissue score matrix.

119. The method according to embodiment 116, wherein the RNA sequence reads are obtained from a plurality of subjects having a known cancer type to construct a cancer RNA tissue score matrix.

120. The method according to embodiment 116, wherein the RNA sequence reads are obtained from a plurality of subjects having a known liver disease to construct a liver disease RNA tissue score matrix.

121. A method for detecting a presence of a liver disease, determining a stage of a liver disease, and/or monitoring progression of a liver disease, the method comprising:
(a) obtaining a biological test sample from the subject, wherein the biological test sample comprises a plurality of cell-free ribonucleic acid (cfRNA) molecules;
(b) quantitatively detecting the presence of a nucleic acid sequence derived from one or more target RNA molecules in the test sample to determine an RNA score from the one or more target RNA molecules, wherein the one or more target RNA molecules are derived from the AKR1B10 gene; and
(c) detecting a presence of a liver disease, determining a stage of a liver disease, and/or monitoring progression of a liver disease in the subject when the tumor RNA score exceeds a threshold value.

122. The method of embodiment 121, wherein quantitatively detecting the presence of the sequences derived from the target RNA molecules comprises conducting a sequencing procedure.

123. The method of embodiment 122, wherein the sequencing procedure comprises whole transcriptome sequencing of the cfRNA molecules in the biological test sample.

124. The method of embodiment 121, wherein quantitatively detecting the presence of the sequences derived from the target RNA molecules comprises sequencing, NGS sequencing, Sanger sequencing, microarray analysis, reverse transcription PCR, real-time PCR, quantitative real-time PCR, digital PCR, digital emulsion PCR, droplet digital PCR, multiplex PCR, hybrid capture, oligonucleotide ligation assays, or any combination thereof.

125. The method of embodiment 121, wherein quantitatively detecting the presence of the sequences derived from the target RNA molecules comprises microarray analysis.

126. The method of embodiment 121, further comprising enriching the cfRNA molecules in the biological test sample for one or more RNA markers prior to quantitatively detecting the presence of a sequence read derived from one or more target RNA molecules.

127. The method of embodiment 121, wherein the liver disease is selected from non-alcoholic fatty liver disease (NAFLD), alcoholic steatohepatitis (ASH), non-alcoholic steatohepatitis (NASH), liver fibrosis, liver cirrhosis, hepatocellular carcinoma (HCC), and any combination thereof.

128. The method of embodiment 121, wherein the tumor RNA score is determined by inputting the sequence reads into a machine learned model.

129. The method of embodiment 121, wherein the machine learned model comprises a logistic regression classifier, logistic regression predictor, a random forest predictor, a gradient boosting machine, Naïve Bayes classifier, support vector machine, or a neural network.

130. The method of embodiment 121, wherein the one or more RNA markers comprise one or more of the markers listed on Table 1.

131. A computer-implemented method for detecting the presence of a liver disease in a subject, the method comprising:
receiving a data set in a computer comprising a processor and a computer-readable medium, wherein the data set comprises a plurality of sequence reads obtained from a plurality of ribonucleic acid (RNA) molecules in a biological test sample from the subject, and wherein the computer-readable medium comprises instructions that, when executed by the processor, cause the computer to:
determine an expression level of a plurality of target RNA molecules in the biological test sample;
compare the expression level of each of the target RNA molecules to an RNA tissue score matrix to determine a liver disease indicator score for each target RNA molecule;
aggregate the liver disease indicator score for each target RNA molecule to generate a liver indicator score for the biological test sample; and
detect the presence of the liver disease in the subject when the liver disease indicator score for the biological test sample exceeds a threshold value.

132. The method according to embodiment 131, wherein the target RNA molecules have an expression level in subjects with a known liver disease status that exceeds their expression level in healthy subjects.

133. The method according to embodiment 132, wherein the expression level of a target RNA molecule in a subject with a known liver disease status is at least 10 times greater than the expression level of the target RNA molecule in a healthy subject.

134. The method according to embodiment 132, wherein the target RNA molecules are not detectable in a biological test sample from a healthy subject.

135. The method according to embodiment 131, wherein the number of target RNA molecules ranges from 1 to 20.

136. The method according to embodiment 131, wherein the threshold value ranges from 0.5 to 5 reads per million (RPM).

137. The method according to any one of embodiments 121-136, wherein the computer is configured to generate a report that comprises: an expression level of one or more of the target RNA molecules, a liver disease indicator score for one or more of the target RNA molecules, a liver indicator score for the biological test sample, an indication of the presence or absence of the liver disease in the subject, a therapeutic classification for the subject, or any combination thereof.

138. The method according to 121-137, wherein the plurality of RNA molecules comprise cell-free RNA (cfRNA) molecules.

139. The method according to 121-137, wherein the plurality of RNA molecules comprise circulating tumor RNA (ctRNA) molecules.

140. The method of according to any one of embodiments 121-137, wherein the plurality of RNA molecules in the biological test sample comprise RNA from cells from one or more subjects known to have a liver disease and cells from a healthy subject.

141. The method according to any one of the preceding embodiments 121-137, wherein the biological test sample comprises a biological fluid.

142. The method according to embodiment 144, wherein the biological fluid comprises blood, plasma, serum, urine, saliva, pleural fluid, pericardial fluid, cerebrospinal fluid (CSF), peritoneal fluid, or any combination thereof.

143. The method according to any one of embodiments 121-141, wherein the biological test sample comprises a tissue biopsy.

144. The method according to embodiment 144, wherein the tissue biopsy is a liver tissue biopsy.

145. The method according to embodiment 144, wherein the tissue biopsy is a healthy tissue biopsy.

146. The method according to any one of embodiments 121-145, wherein the liver disease condition is selected from non-alcoholic fatty liver disease (NAFLD), alcoholic steatohepatitis (ASH), non-alcoholic steatohepatitis (NASH), liver fibrosis, liver cirrhosis, hepatocellular carcinoma (HCC), and any combination thereof.

EXEMPLARY EMBODIMENTS (B)

The present description provides the following embodiments, with some embodiments of this paragraph referring to other numbered embodiments of this paragraph:

1. A method of measuring a subpopulation of cell-free RNA (cfRNA) molecules of a subject, the method comprising:
   a. sequencing the cfRNA molecules to produce cfRNA sequence reads;
   b. sequencing cellular RNA extracted from cells of the subject to produce cellular sequence reads;
   c. performing a filtering procedure to produce a non-excluded population of cfRNA sequence reads, wherein the filtering comprises excluding cfRNA sequence reads that match one or more of the cellular sequence reads; and
   d. quantifying one or more of the non-excluded sequence reads.

2. The method of embodiment 1, wherein sequencing the cfRNA molecules comprises reverse transcription to produce cDNA molecules, and sequencing the cDNA molecules to produce the cfRNA sequence reads.

3. The method of embodiment 1, wherein sequencing the cfRNA molecules comprises:
   a. reverse transcribing the cfRNA molecules to produce a plurality of cDNA/RNA hybrid molecules;
   b. synthesizing a plurality of double-stranded cDNA molecules from the cDNA/RNA hybrid molecules;
   c. ligating a plurality of double-stranded polynucleotide adapters to the plurality of double-stranded cDNA molecules, thereby producing a sequencing library; and
   d. sequencing at least a portion of the sequencing library to produce the cfRNA sequence reads.

4. The method of any one of embodiments 1-3, wherein sequencing the cfRNA molecules comprises whole transcriptome sequencing.

5. The method of any one of embodiments 1-3, wherein sequencing the cfRNA molecules comprises enriching the cfRNA molecules or cDNA molecules thereof for one or more target polynucleotides.

6. The method of any one of embodiments 1-5, wherein the non-excluded sequence reads only include reads or read pairs that overlap an exon-exon junction.

7. The method of any one of embodiments 1-6, wherein the cfRNA is from a biological test sample of the subject comprising a biological fluid.

8. The method of embodiment 7, wherein the biological fluid comprises blood, plasma, serum, urine, saliva, pleural fluid, pericardial fluid, cerebrospinal fluid (CSF), peritoneal fluid, or any combination thereof.

9. The method of any one of embodiments 1-8, wherein the cfRNA molecules are obtained from blood, a blood fraction, plasma, or serum of the subject.

10. The method of any one of embodiments 1-9, wherein the cells are obtained from blood or a blood fraction of the subject.

11. The method of embodiment 10, wherein the cfRNA molecules and the cells are obtained from a blood sample of the subject.

12. The method of any one of embodiments 1-11, wherein the cells are white blood cells (WBCs).

13. The method of any one of embodiments 1-12, further comprising detecting a condition of the subject, wherein detecting the condition comprises detecting one or more non-excluded sequence reads above a threshold.

14. The method of embodiment 13, wherein detecting one or more non-excluded sequence reads above a threshold comprises (i) detection, (ii) detection above background, or (iii) detection at a level that is greater than a level of corresponding sequence reads in subjects that do not have the condition.

15. The method of embodiment 13, wherein detecting one or more non-excluded sequence reads above a threshold comprises detecting the one or more sequence reads at a level that is at least about 10 times greater than a level of corresponding sequence reads in subjects that do not have the condition.

16. The method of embodiment 13, wherein detecting one or more non-excluded sequence reads above a threshold comprises detection above a threshold value of 0.5 to 5 reads per million (RPM).

17. The method of embodiment 13, wherein detecting one or more non-excluded sequence reads above a threshold comprises:
   (a) determining an expression level of a plurality of target cfRNA molecules;
   (b) determining an indicator score for each target cfRNA molecule by comparing the expression level of each of the target cfRNA molecules to an RNA tissue score matrix;
   (c) aggregating the indicator scores for each target cfRNA molecule; and,
   (d) detecting presence of the condition in the subject when the indicator score exceeds a threshold value.

18. The method of embodiment 13, wherein detecting one or more non-excluded sequence reads above a threshold comprises inputting the sequence reads into a machine learning or deep learning model.

19. The method of embodiment 18, wherein the machine learning or deep learning model comprises logistic regression, random forest, gradient boosting machine, Naïve Bayes, neural network, or multinomial regression.

20. The method of embodiment 18, wherein the machine learning or deep learning model transforms the values of the one or more features to the disease state prediction for the subject through a function comprising learned weights.

21. The method of any one of embodiments 13-20, wherein the condition is cardiovascular disease, liver disease, or a cancer.

22. The method of embodiment 21, wherein the condition is a liver disease selected from non-alcoholic fatty liver disease (NAFLD), alcoholic steatohepatitis (ASH), non-alcoholic steatohepatitis (NASH), liver fibrosis, liver cirrhosis, hepatocellular carcinoma (HCC), and any combination thereof.

23. The method of embodiment 21, wherein the condition is a cancer comprising:

(i) a carcinoma, a sarcoma, a myeloma, a leukemia, a lymphoma, a blastoma, a germ cell tumor, or any combination thereof;

(ii) a carcinoma selected from the group consisting of adenocarcinoma, squamous cell carcinoma, small cell lung cancer, non-small-cell lung cancer, nasopharyngeal, colorectal, anal, liver, urinary bladder, testicular, cervical, ovarian, gastric, esophageal, head-and-neck, pancreatic, prostate, renal, thyroid, melanoma, and breast carcinoma;

(iii) hormone receptor negative breast carcinoma or triple negative breast carcinoma;

(iv) a sarcoma selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma;

(v) a leukemia selected from the group consisting of myelogenous, granulocytic, lymphatic, lymphocytic, and lymphoblastic leukemia; or (vi) a lymphoma selected from the group consisting of: Hodgkin's lymphoma and Non-Hodgkin's lymphoma.

24. The method of any one of embodiments 13-23, wherein the one or more non-excluded sequence reads detected above a threshold originate from a transcript of a diseased cell, and the method further comprises the step of identifying the tissue origin of the diseased cell.

25. The method of embodiment 24, wherein the tissue origin is selected from the group consisting of pancreatic tissue, liver tissue, lung tissue, brain tissue, uterus tissue, renal tissue, breast tissue, fat, colon tissue, rectum tissue, heart tissue, skeletal muscle tissue, prostate tissue and thyroid tissue.

26. The method of any one of embodiments 13-23, wherein the one or more non-excluded sequence reads detected above a threshold originate from a transcript of a cancer cell, and the method further comprises determining a cancer cell type or tissue of origin of the cancer in the subject.

27. The method of any one of embodiments 13-26, wherein the one or more non-excluded sequence reads detected above a threshold are sequence reads of one or more target polynucleotides enriched from the cfRNA molecules or amplicons thereof.

28. The method of any one of embodiments 13-27, wherein the one or more non-excluded sequence reads detected above a threshold are sequence reads for cfRNA molecules derived from 1 to 20 target genes.

29. The method of any one of embodiments 13-28, wherein (i) the condition is cancer, and (ii) the one or more non-excluded sequence reads detected above a threshold are sequence reads for cfRNA molecules derived from one or more genes selected from the group consisting of: AGR2, BPIFA1, CASP14, CSN1S1, DISP2, EIF2D, FABP7, GABRG1, GNAT3, GRHL2, HOXC10, IDI2-AS1, KRT16P2, LALBA, LINC00163, NKX2-1, OPN1SW, PADI3, PTPRZ1, ROS1, S100A7, SCGB2A2, SERPINB5, SFTA3, SFTPA2, SLC34A2, TFF1, VTCN1, WFDC2, MUC5B, SMIM22, CXCL17, RNU1-1, and KLK5.

30. The method of any one of embodiments 13-28, wherein (i) the condition is lung cancer, and (ii) the one or more non-excluded sequence reads detected above a threshold are sequence reads for cfRNA molecules derived from one or more genes selected from the group consisting of: ROS1, NKX2-1, GGTLC1, SLC34A2, SFTPA2, BPIFA1, SFTA3, GABRG1, AGR2, GNAT3, MUC5B, SMIM22, CXCL17, and WFDC2.

31. The method of any one of embodiments 13-28, wherein (i) the condition is breast cancer, and (ii) the one or more non-excluded sequence reads detected above a threshold are sequence reads for cfRNA molecules derived from one or more genes selected from the group consisting of: SCGB2A2, CSN1S1, VTCN1, FABP7, LALBA, RNU1-1, OPN1SW, CASP14, KLK5, and WFDC2.

32. The method of any one of embodiments 13-28, wherein (i) the condition is breast cancer, and (ii) the one or more non-excluded sequence reads detected above a threshold are sequence reads for cfRNA molecules derived from one or more genes selected from the group consisting of: CASP14, CRABP2, FABP7, SCGB2A2, SERPINB5, TRGV10, VGLL1, TFF1, and AC007563.5.

33. The method of any one of embodiments 13-28, wherein (i) the condition is liver disease, and (ii) the one or more non-excluded sequence reads detected above a threshold are sequence reads for cfRNA molecules derived from one or more genes selected from the group consisting of: AKR1B10, C3, and PIEXO2.

34. The method of any one of embodiments 13-33, further comprising selecting a treatment based on the condition detected.

35. The method of embodiment 34, wherein the condition is cancer, and the treatment comprises surgical resection, radiation therapy, or administering an anti-cancer agent.

36. The method of embodiment 34 or 35, wherein the method further comprises treating the subject with the selected treatment.

37. A method of detecting cancer in a subject, the method comprising:

(a) measuring a plurality of target cell-free RNA (cfRNA) molecules in a sample of the subject, wherein the plurality of target cfRNA molecules are selected from one or more transcripts of Tables 1-7; and (b) detecting the cancer, wherein detecting the cancer comprises detecting one or more of the target cfRNA molecules above a threshold level.

38. The method of embodiment 37, wherein the plurality of target cfRNA molecules are selected from at least 5, 10, 15, or 20 transcripts of Tables 1-7.

39. The method of embodiment 37, wherein the plurality of target cfRNA molecules comprise a plurality of transcripts from Table 1, from each of Table 2 and 5, or from each of Tables 3-4 and 6.

40. The method of any one of embodiments 37-39, wherein the plurality of target cfRNA molecules comprise all of the transcripts of one or more of Tables 1, 2, 3, 4, 5, or 6.

41. The method of embodiment 37, wherein the plurality of target cfRNA molecules comprise transcripts from one or more of Tables 1-6 and one or more transcripts from Table 7.

42. The method of embodiment 37, wherein the plurality of target cfRNA molecules detected above a threshold are cfRNA molecules derived from a plurality of genes selected from the group consisting of: AGR2, BPIFA1, CASP14, CSN1S1, DISP2, EIF2D, FABP7, GABRG1, GNAT3, GRHL2, HOXC10, IDI2-AS1, KRT16P2, LALBA, LINC00163, NKX2-1, OPN1SW, PADI3, PTPRZ1, ROS1, S100A7, SCGB2A2, SERPINB5, SFTA3, SFTPA2, SLC34A2, TFF1, VTCN1, WFDC2, MUCSB, SMIM22, CXCL17, RNU1-1, and KLK5.

43. The method of embodiment 37, wherein (i) the cancer is lung cancer, and (ii) the plurality of target cfRNA molecules detected above a threshold are cfRNA molecules derived from a plurality of genes selected from the group consisting of: ROS1, NKX2-1, GGTLC1, SLC34A2, SFTPA2, BPIFA1, SFTA3, GABRG1, AGR2, GNAT3, MUCSB, SMIM22, CXCL17, and WFDC2.

44. The method of embodiment 37, wherein (i) the cancer is breast cancer, and (ii) the plurality of target cfRNA molecules detected above a threshold are cfRNA molecules derived from a plurality of genes selected from the group consisting of: SCGB2A2, CSN1S1, VTCN1, FABP7, LALBA, RNU1-1, OPN1SW, CASP14, KLK5, and WFDC2.

45. The method of embodiment 37, wherein (i) the cancer is breast cancer, and (ii) the plurality of target cfRNA molecules detected above a threshold are cfRNA molecules derived from a plurality of genes selected from the group consisting of: CASP14, CRABP2, FABP7, SCGB2A2, SERPINB5, TRGV10, VGLL1, TFF1, and AC007563.5.

46. The method of any one of embodiments 37-45, wherein the measuring comprises sequencing, microarray analysis, reverse transcription PCR, real-time PCR, quantitative real-time PCR, digital PCR, digital droplet PCR, digital emulsion PCR, multiplex PCR, hybrid capture, oligonucleotide ligation assays, or any combination thereof.

47. The method of any one of embodiments 37-46, wherein the measuring comprises sequencing cfRNA molecules to produce cfRNA sequence reads.

48. The method of embodiment 47, wherein sequencing the cfRNA molecules comprises whole transcriptome sequencing.

49. The method of embodiment 47 or 48, wherein sequencing the cfRNA molecules comprises reverse transcription to produce cDNA molecules, and sequencing the cDNA molecules to produce the cfRNA sequence reads.

50. The method of embodiment 47, wherein sequencing the cfRNA molecules comprises enriching for the target cfRNA molecules or cDNA molecules thereof.

51. The method of any one of embodiments 37-50, wherein the sample comprises a biological fluid.

52. The method of embodiment 51, wherein the biological comprises blood, plasma, serum, urine, saliva, pleural fluid, pericardial fluid, cerebrospinal fluid (CSF), peritoneal fluid, or any combination thereof.

53. The method of embodiment 51, wherein the biological comprises blood, a blood fraction, plasma, or serum of the subject.

54. The method of any one of embodiments 37-53, wherein detecting one or more of the target cfRNA molecules above a threshold level comprises (i) detection, (ii) detection above background, or (iii) detection at a level that is greater than a level of the target cfRNA molecules in subjects that do not have the condition.

55. The method of any one of embodiments 37-53, wherein detecting one or more of the target cfRNA molecules above a threshold level comprises detecting the one or more target cfRNA molecules at a level that is at least about 10 times greater than a level in subjects that do not have the condition.

56. The method of any one of embodiments 47-53, wherein detecting one or more of the target cfRNA molecules above a threshold level comprises detection above a threshold value of 0.5 to 5 reads per million (RPM).

57. The method of any one of embodiments 37-53, wherein detecting one or more of the target cfRNA molecules above a threshold level comprises:
  (a) determining an indicator score for each target cfRNA molecule by comparing the expression level of each of the target cfRNA molecules to an RNA tissue score matrix;
  (b) aggregating the indicator scores for each target cfRNA molecule; and,
  (c) detecting the cancer when the indicator score exceeds a threshold value.

58. The method of any one of embodiments 47-57, wherein detecting one or more of the target cfRNA molecules above a threshold level comprises inputting the sequence reads into a machine learning or deep learning model.

59. The method of embodiment 58, wherein the machine learning or deep learning model comprises logistic regression, random forest, gradient boosting machine, Naïve Bayes, neural network, or multinomial regression.

60. The method of embodiment 58, wherein the machine learning or deep learning model transforms the values of the one or more features to the disease state prediction for the subject through a function comprising learned weights.

61. The method of any one of embodiments 37-60, wherein the cancer comprises:
  (i) a carcinoma, a sarcoma, a myeloma, a leukemia, a lymphoma, a blastoma, a germ cell tumor, or any combination thereof;
  (ii) a carcinoma selected from the group consisting of adenocarcinoma, squamous cell carcinoma, small cell lung cancer, non-small-cell lung cancer, nasopharyngeal, colorectal, anal, liver, urinary bladder, testicular, cervical, ovarian, gastric, esophageal, head-and-neck, pancreatic, prostate, renal, thyroid, melanoma, and breast carcinoma;
  (iii) hormone receptor negative breast carcinoma or triple negative breast carcinoma;
  (iv) a sarcoma selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma;
  (v) a leukemia selected from the group consisting of myelogenous, granulocytic, lymphatic, lymphocytic, and lymphoblastic leukemia; or
  (vi) a lymphoma selected from the group consisting of: Hodgkin's lymphoma and Non-Hodgkin's lymphoma.

62. The method of any one of embodiments 37-61, wherein detecting the cancer comprises determining a cancer stage, determining cancer progression, determining a cancer type, determining cancer tissue of origin, or a combination thereof.

63. The method of any one of embodiments 37-62, further comprising selecting a treatment based on the cancer detected.

64. The method of embodiment 63, wherein the treatment comprises surgical resection, radiation therapy, or administering an anti-cancer agent.

65. The method of embodiment 63 or 64, wherein the method further comprises treating the subject with the selected treatment.

66. A method of identifying cancer biomarkers in samples collected from one or more subjects, the method comprising:
  (a) sequencing cfRNA of a biological fluid collected from subjects without cancer to produce non-cancer sequencing reads;

(b) for a plurality of matched samples collected from one or more subjects with a cancer:
  (i) sequencing DNA and RNA collected from a cancer tissue of a matched sample to produce sequencing reads for the cancer tissue;
  (ii) sequencing cfDNA and cfRNA collected from a matched biological fluid of the matched sample to produce sequencing reads for the matched biological fluid;
  (iii) measuring a tumor fraction by relating counts of cfDNA sequencing reads for the matched biological fluid to corresponding counts of DNA sequencing reads for the cancer tissue; and
  (iv) measuring tumor content for one or more candidate biomarkers by multiplying a count of the RNA sequencing reads for the one or more candidate biomarkers by the tumor fraction, wherein the one or more candidate biomarkers are expressed at a higher level in the matched biological fluid than in the biological fluid collected from the subjects without cancer;
(c) modeling expression of the one or more candidate biomarkers in cfRNA using the tumor content as a covariate; and
(d) identifying one or more cfRNA cancer biomarkers from among the one or more candidate biomarkers based on the modeling.

67. The method of embodiment 66, wherein the method further comprises: selectively measuring expression of the one or more cancer biomarkers in a biological fluid of a test subject.

68. The method of embodiment 66, wherein the method further comprises: sequencing cfRNA from a biological fluid of a test subject, and generating an output for the test subject based on levels of the one or more cancer biomarkers, wherein the output indicates: a presence of cancer, determines a cancer stage, monitors a cancer progression, or determines a cancer type.

69. The method of embodiment 68, wherein a machine learning or deep learning model transforms values for sequencing reads of the cfRNA of the test subject to the output for the test subject through a function comprising learned weights.

70. The method of embodiment 68, further comprising selecting a cancer treatment for the test subject, and optionally administering the treatment to the test subject.

71. The method of any one of embodiments 66-70, wherein the modeling comprises negative binomial general linear model analysis (NB-GLM).

72. The method of any one of embodiments 66-70, wherein the modeling is performed using a computer-implemented classification model which applies at least one of a leave-one-out (LOO) or k-fold cross validation classification to classify different cancer features, wherein k-fold is at least 5-fold.

73. The method of any one of embodiments 66-71, wherein the modeling comprises inputting the one or more DNA, RNA cfDNA or cfRNA sequences into a machine learning or deep learning model.

74. The method of embodiment 73, wherein the machine learning or deep learning model comprises logistic regression, random forest, gradient boosting machine, Naïve Bayes, neural network, or multinomial regression.

75. A computer system for implementing one or more steps in the method of any one of embodiments 1-74.

76. A non-transitory, computer-readable medium, having stored thereon computer-readable instructions for implementing one or more steps in the method of any one of embodiments 1-74.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Example 1: Detection of Tissue-Specific RNA in the Plasma of Cancer Patients

Cell-free RNA (cfRNA) is a promising analyte for cancer detection, but a comprehensive assessment of cfRNA is lacking. To characterize tumor-derived RNA in plasma, we performed an exploratory analysis from a Circulating Cell-free Genome Atlas (CCGA) substudy to examine cfRNA expression in participants with and without cancer. This analysis focused on breast, lung, and colorectal cancers due to their high incidence in the general population and in CCGA.

We selected 210 participants from the CCGA training set (Klein et al., ASCO, 2018). A total of 98 participants were diagnosed with stage III cancer at the time of blood draw (breast (47 patients), lung (32 patients), colorectal (15 patients), and anorectal (4 patients)). Stage III samples were selected to maximize signal in the blood and avoid confounding signal from potential secondary metastases. 112 non-cancer participants frequency-age-matched to the cancer group were also included. For each participant, whole transcriptome libraries from buffy coat, cfRNA, and FFPE of tumor tissue biopsies were generated.

Figure 11:
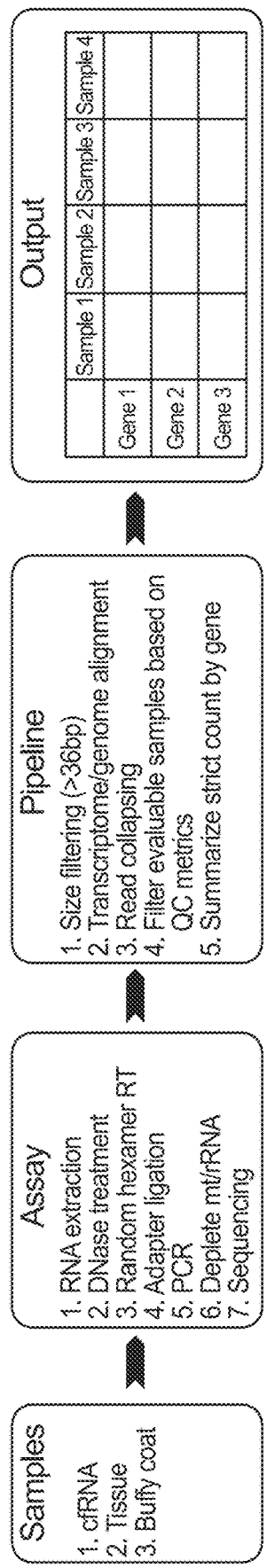
FIG. 11 is a flowchart illustrating a method in accordance with some embodiments.

Nucleic acids were extracted from participant plasma, samples were DNAse-treated to remove cell-free DNA (cfDNA) and genomic DNA, and reverse transcription was performed using random hexamer primers to capture the whole transcriptome for each study participant. The resulting cDNA was converted into DNA libraries, amplified, and depleted of abundant sequences arising from ribosomal, mitochondrial, and blood-related transcripts, such as globins. The resulting whole-transcriptome RNA-seq libraries were sequenced at a depth of ~750M paired-end reads per sample and analyzed using a custom bioinformatics pipeline that generated UMI-collapsed counts for each gene on a sample-by-sample basis. This same procedure was used to create and analyze RNA-seq libraries from matched buffy coat and tissue RNA when available. Due to the presence of residual DNA contamination, all downstream analyses relied on the use of strict RNA reads, defined in this example as read pairs where at least one read overlapped an exon-exon junction. FIG. 11 shows a summary of the end-to-end workflow. Table 9 provides a summary of participant samples:

TABLE 9

| Disease Status | Passed QC | cfRNA | WBC | Tissue |
| --- | --- | --- | --- | --- |
| Breast | Fail | 1 | 0 | 0 |
| Lung | Fail | 2 | 1 | 0 |
| Non-cancer | Fail | 4 | 0 | 0 |
| Anorectal | Pass | 4 | 1 | 4 |

TABLE 9-continued

| Disease Status | Passed QC | cfRNA | WBC | Tissue |
|---|---|---|---|---|
| Breast | Pass | 46 | 32 | 40 |
| Colorectal | Pass | 15 | 11 | 10 |
| Lung | Pass | 30 | 26 | 12 |
| Non-cancer | Pass | 89 | 93 | 0 |
| Young Healthy | Pass | 19 | 19 | 0 |
| Total | NA | 210 | 183 | 66 |

Figure 12A:
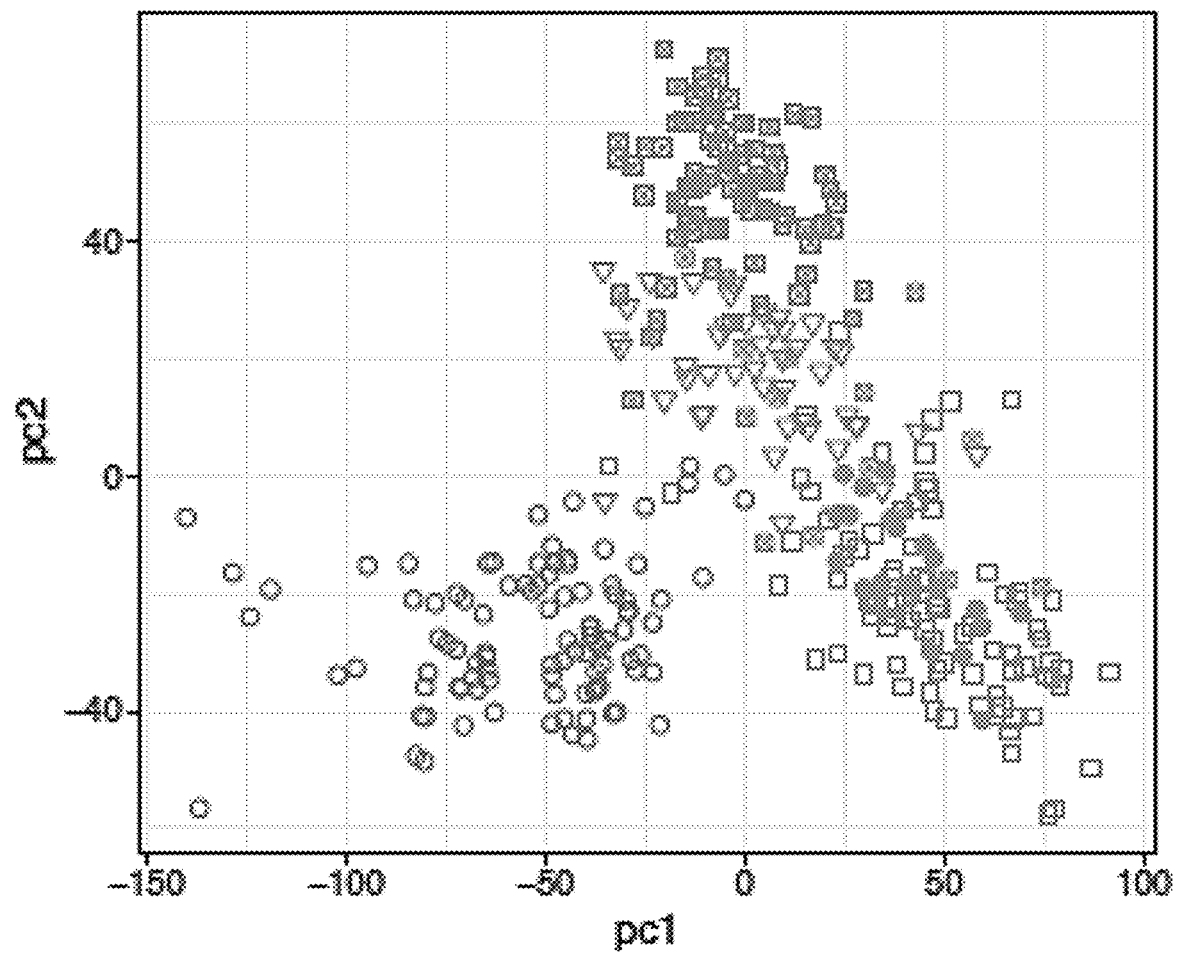
FIG. 12A is a scatter plot of an example PCA (principal component analysis) of stage III TCGA (The Cancer Genome Atlas) FFPE (formalin-fixed paraffin embedded) tissue RNA-seq data. Gene expression levels are plotted in read per million.
Figure 12B:
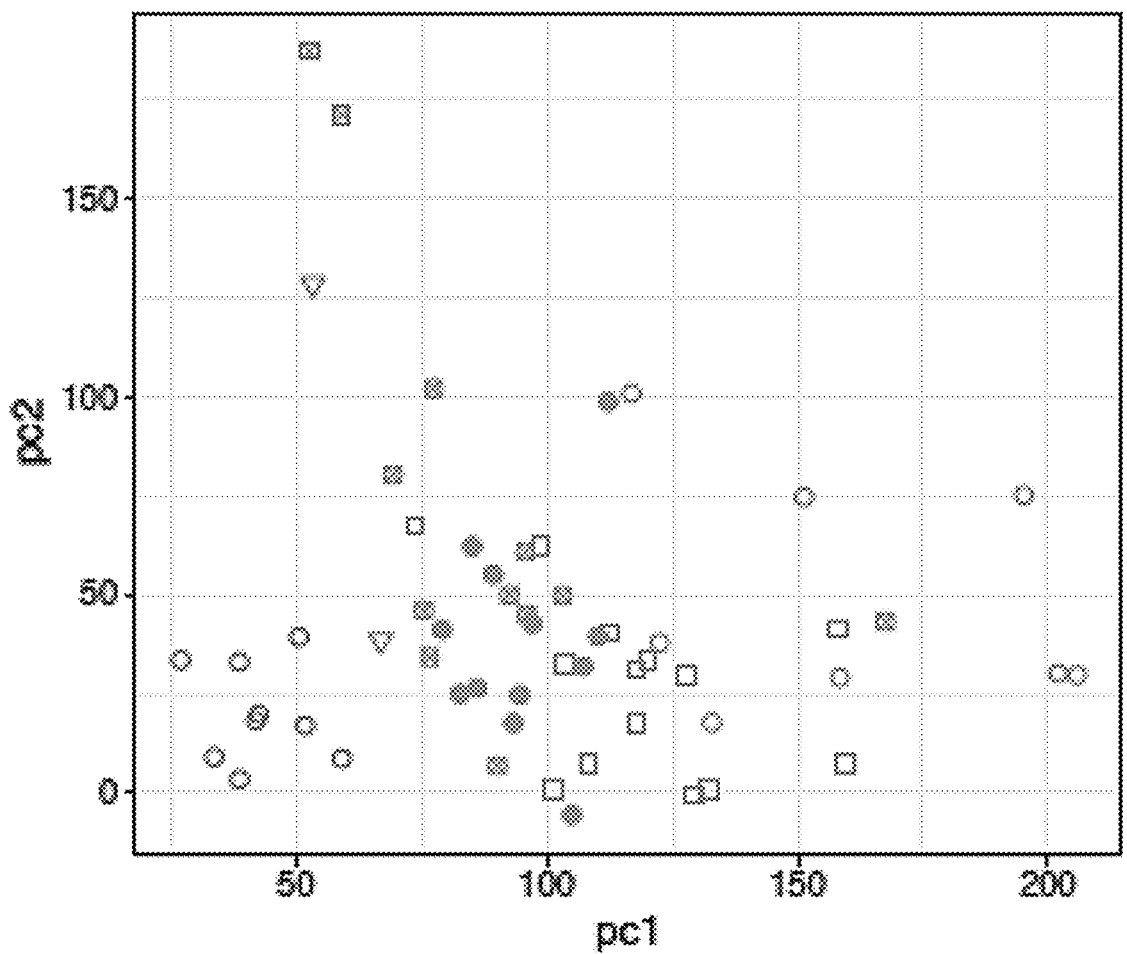
FIG. 12B is scatter plot showing example results of CCGA (Circulating Cell-free Genome Atlas) tumor tissue RNA-seq data, projected on TCGA PCA axes. Gene expression levels are plotted in read per million.
Figure 12C:
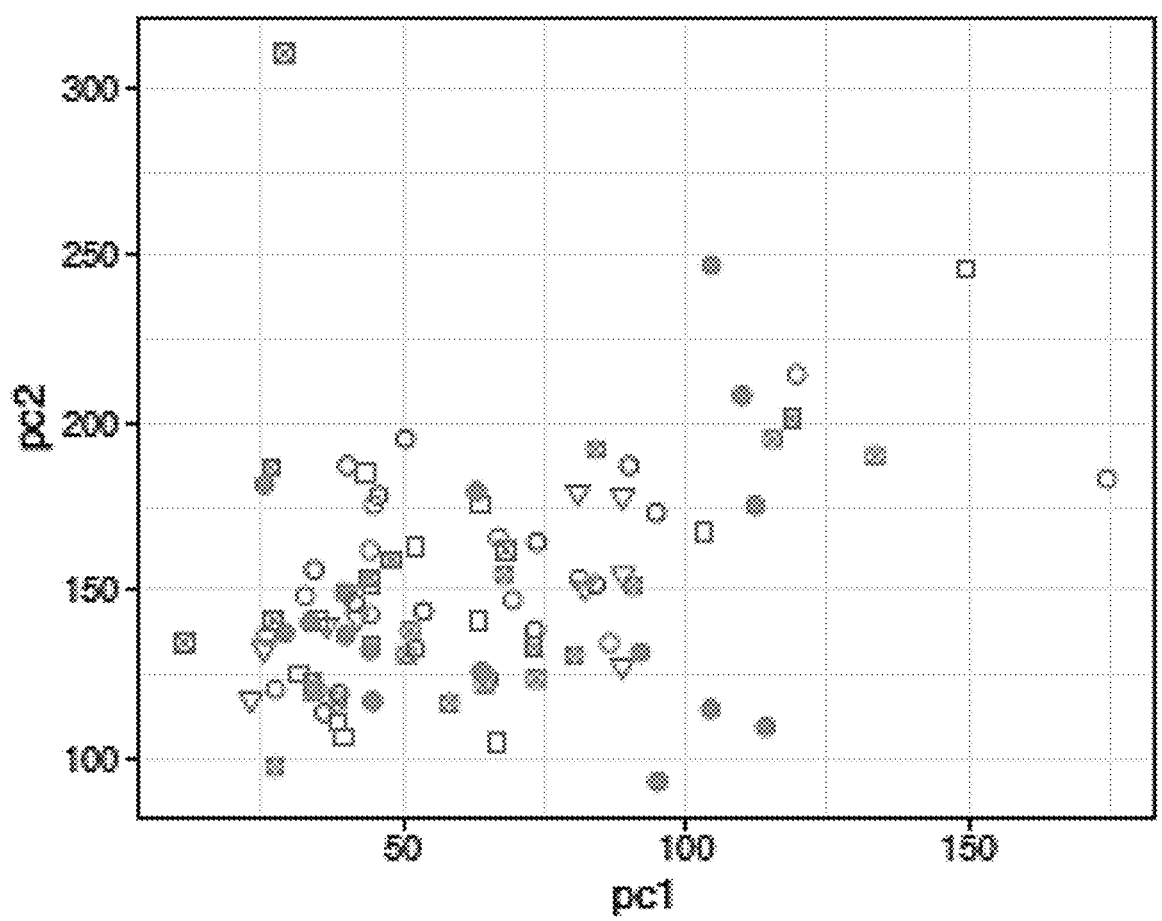
FIG. 12C is a scatter plot showing example results of CCGA cancer cell-free RNA (cfRNA) RNA-seq data projected on TCGA PCA axes. Gene expression levels are plotted in read per million.

We compared our data to RNA samples from TCGA (FIG. 12A). When we projected CCGA tumor tissue RNA-seq data onto the principal components derived from TCGA tumor tissue RNA-seq data, the CCGA tumor tissue samples were separable by cancer type (FIG. 12B). These results suggest that the expression profiles of CCGA and TCGA tumors were very similar in spite of differences in sample collection/handling/library preparation, and validate the analytical approach. A projection of cancer cfRNA samples from the CCGA cohort onto the principal components derived from TCGA tumor tissue RNA-seq data showed no separation of the sample by cancer type (FIG. 12C), implying that cancer type was not the dominant source of variance in cfRNA.

The majority of cfRNA in plasma is thought to originate from healthy immune cells. As such, we treated these transcripts as background noise and focused on tumor-derived cfRNA as a source of cancer signal. Our analysis identified two classes of genes in cfRNA data: "dark channels" and "dark channel biomarkers". Dark channels are genes that were not detected in the cfRNA of non-cancer participants. Of 57,783 annotated genes, 39,564 (68%) were identified as dark channels. Dark channel biomarker (DCB) genes met three criteria: 1) median expression of the gene in the non-cancer cohort was zero, 2) gene expression was detected in more than one participant in the cancer cohort, and 3) gene expression was up-regulated in the cancer group.

14 DCB genes were identified for lung cancer: SLC34A2, GABRG1, ROS1, AGR2, GNAT3, SFTPA2, MUCSB, SFTA3, SMIM22, CXCL17, BPIFA1, WFDC2, NKX2-1, and GGTLC1 (see Table 2). 10 DCB genes were identified for breast cancer: RNU1-1, CSN1S1, FABP7, OPN1SW, SCGB2A2, LALBA, CASP14, KLK5, WFDC2, and VTCN1 (see Table 3). No DCB genes were identified for colorectal cancer.

Figure 13:
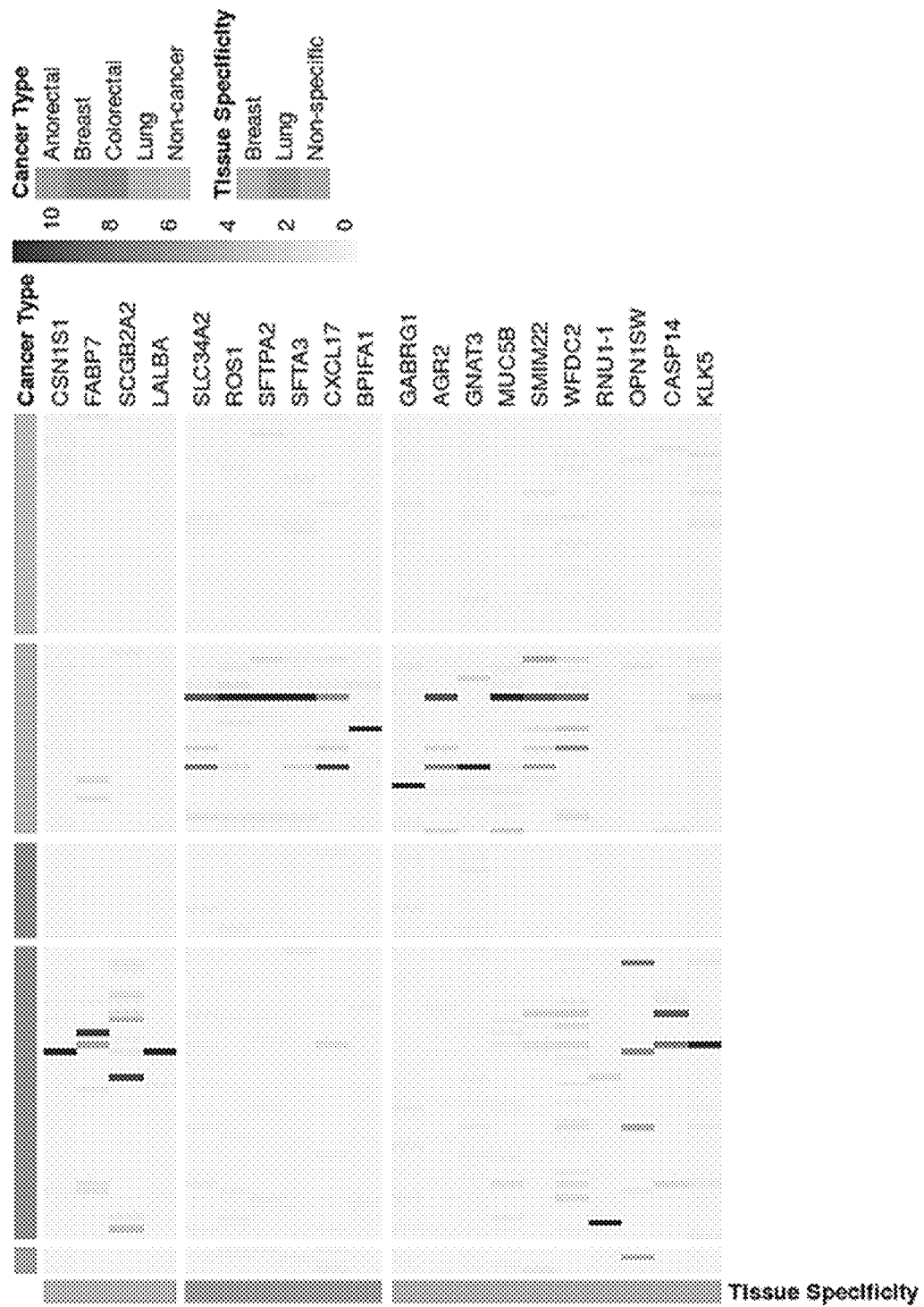
FIG. 13 is a heatmap of example dark channel biomarker genes. Each column depicts one cfRNA sample, and each row depicts one gene. The color of the rows encodes tissue-specificity (from top to bottom, the tissues are, respectively: breast, lung, and non-specific). The color of the columns encodes the sample groups (from left to right, the cancer types are, respectively: anorectal, breast, colorectal, lung, and non-cancer).

DCB genes exhibited several distinct characteristics. First, DCB genes were enriched for tissue-specific genes (FIG. 13). Among the 57,783 annotated genes, 0.3% were lung-specific and 0.2% were breast-specific. In comparison, 50% of the lung DCB genes were lung-specific, and 44% of the breast DCB genes were breast-specific (as defined by the protein atlas database (Uhlén et al., Science, 2015)).

Figure 14:
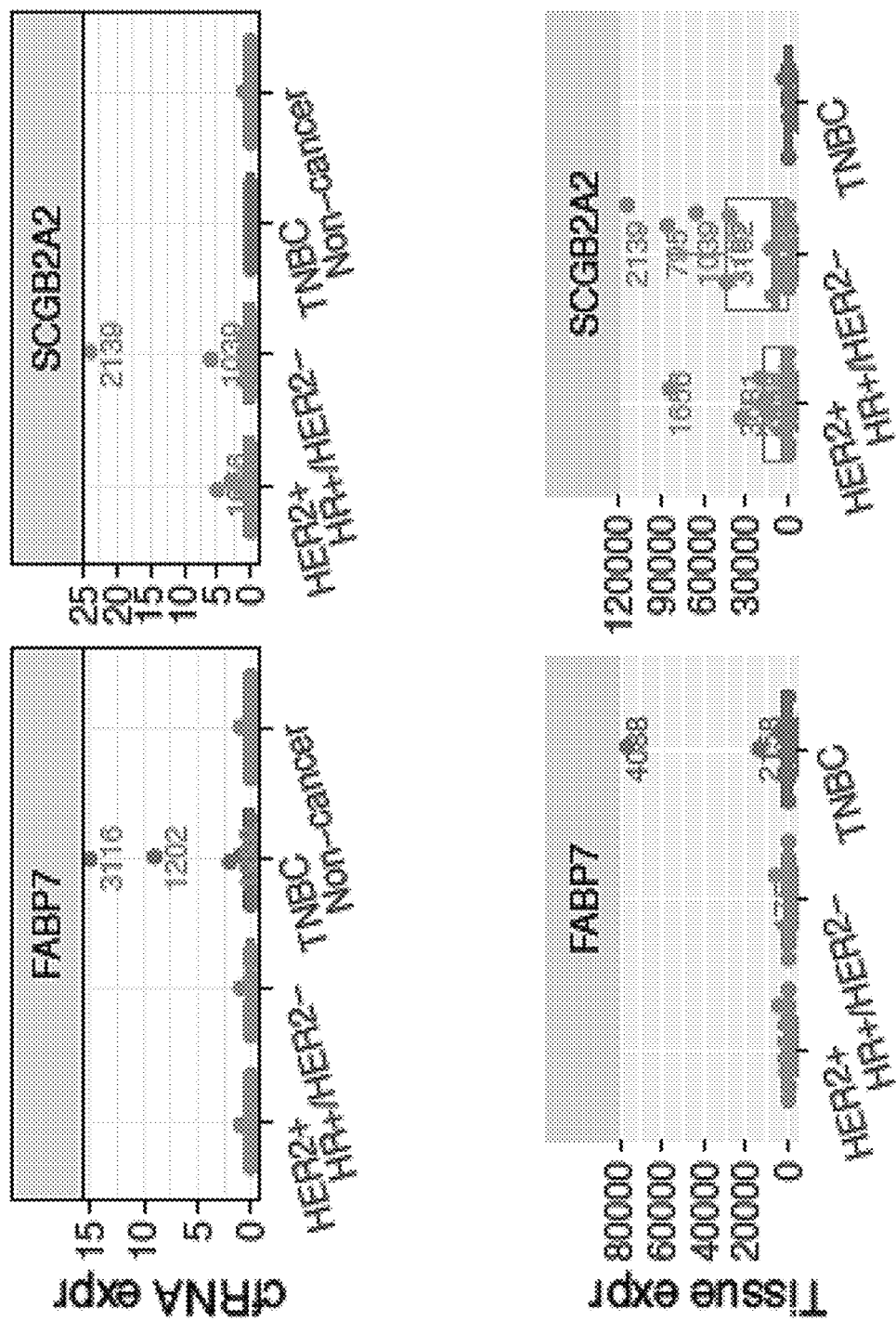
FIG. 14A shows box plots depicting cfRNA expression levels and tissue expression levels of two example breast dark channel biomarkers (DCB) genes (FABP7 and SCGB2A2) in different samples: HER2+, HR+/HER2−, triple negative breast cancer (TNBC), or non-cancer samples.
FIG. 14B shows box plots depicting cfRNA expression levels and tissue expression levels of four example lung DCB genes (SLC34A2, ROS1, SFTPA2, and CXCL17) in different samples: adenocarcinoma, small cell lung cancer, squamous cell carcinoma, or non-cancer samples.
Figure 14B:
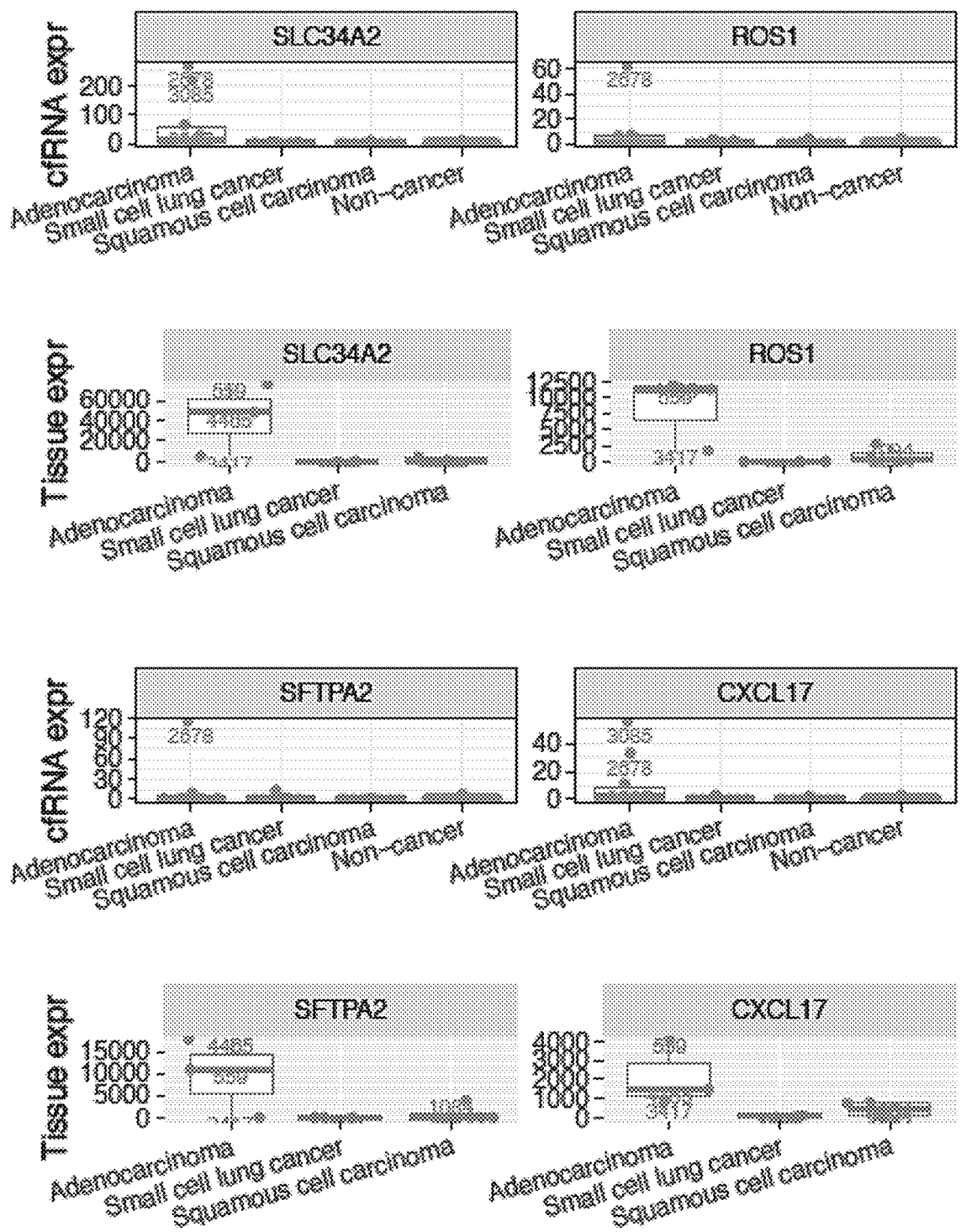

Moreover, some DCB genes were subtype-specific biomarkers that were only detected in certain cancer subtypes (FIGS. 14A and 14B). FABP7 was only detected in triple negative breast cancer (TNBC) samples. Conversely, SCGB2A2 was not detected in TNBC, but was detected in HER2+ and HR+/HER– breast cancer samples. SLC34A2, ROS1, SFTPA2 and CXCL17 genes were detected in cfRNA of lung adenocarcinoma patient samples but not in squamous cell carcinoma patient samples. These subtype-specific genes also had higher expression in tumor tissue compared to other subtypes of cancer originating from the same organ.

Figure 15A:
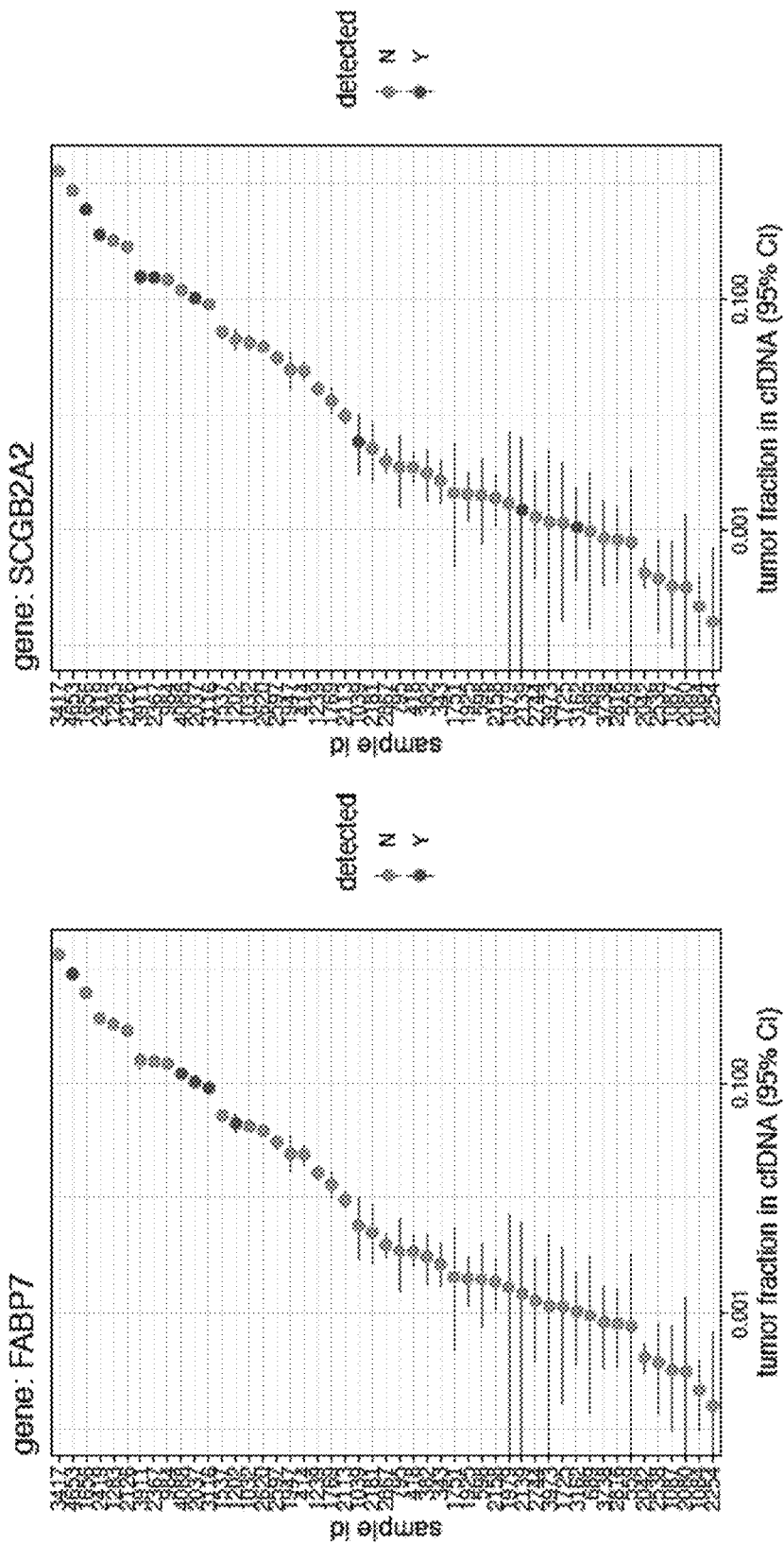
FIG. 15A shows forest plots depicting the detectability of two breast DCB genes (FABP7 and SCGB2A2) for breast cancer samples with matched tumor tissue. The samples IDs are plotted based on their relative tumor fraction in cell-free DNA (cfDNA) (95% CI). FABP7 was detected in samples 4653, 4088, 2037, 3116, and 1202. SCGB2A2 was detected in samples 1656, 2419, 3911, 2367, 2037, 1039, 2139, and 3162. Tumor fraction in cfDNA was measured from SNV allele fractions from the cfDNA enrichment assay.
Figure 15B:
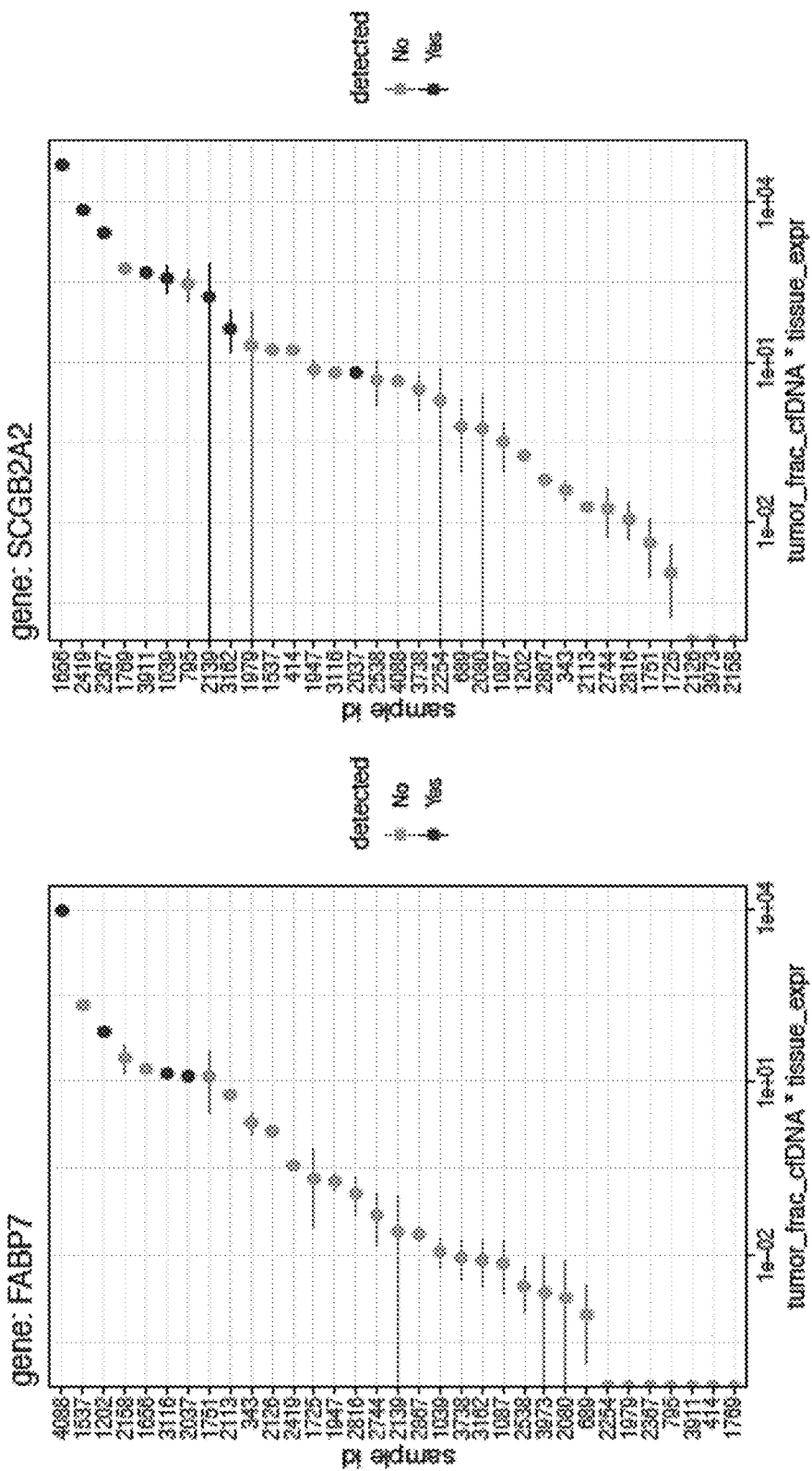
FIG. 15B shows forest plots depicting the detectability of two breast DCB genes (FABP7 and SCGB2A2) for breast cancer samples with matched tumor tissue. Sample IDs are plotted as a function of tumor content (tumor fraction*tumor tissue expression). FABP7 was detected in samples 4088, 1202, 3116, and 2037. SCGB2A2 was detected in samples 1656, 2419, 2367, 3911, 1039, 2139, 3162, and 2037. Tumor fraction in cfDNA was measured from SNV allele fractions from the cfDNA enrichment assay. Tissue expression was measured from RNA-seq data of matched tumor tissue.
Figure 16A:
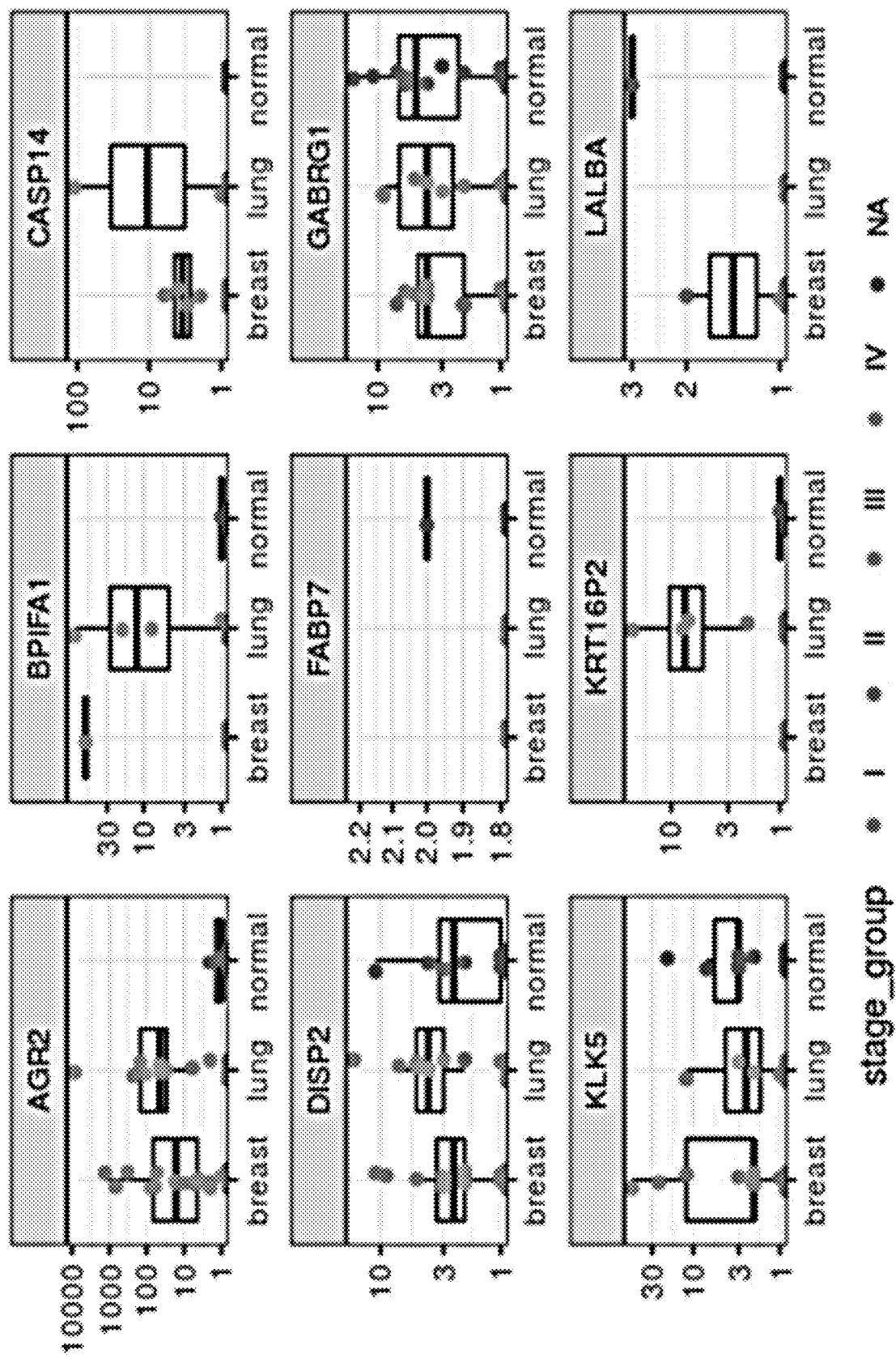
FIGS. 16A-D illustrate example sequencing results for DCB gene expression in cfRNA and matched tissue for the indicated genes for subjects with breast cancer, lung cancer, or no cancer (normal). The number of read counts is represented on the y-axis.
Figure 16B:
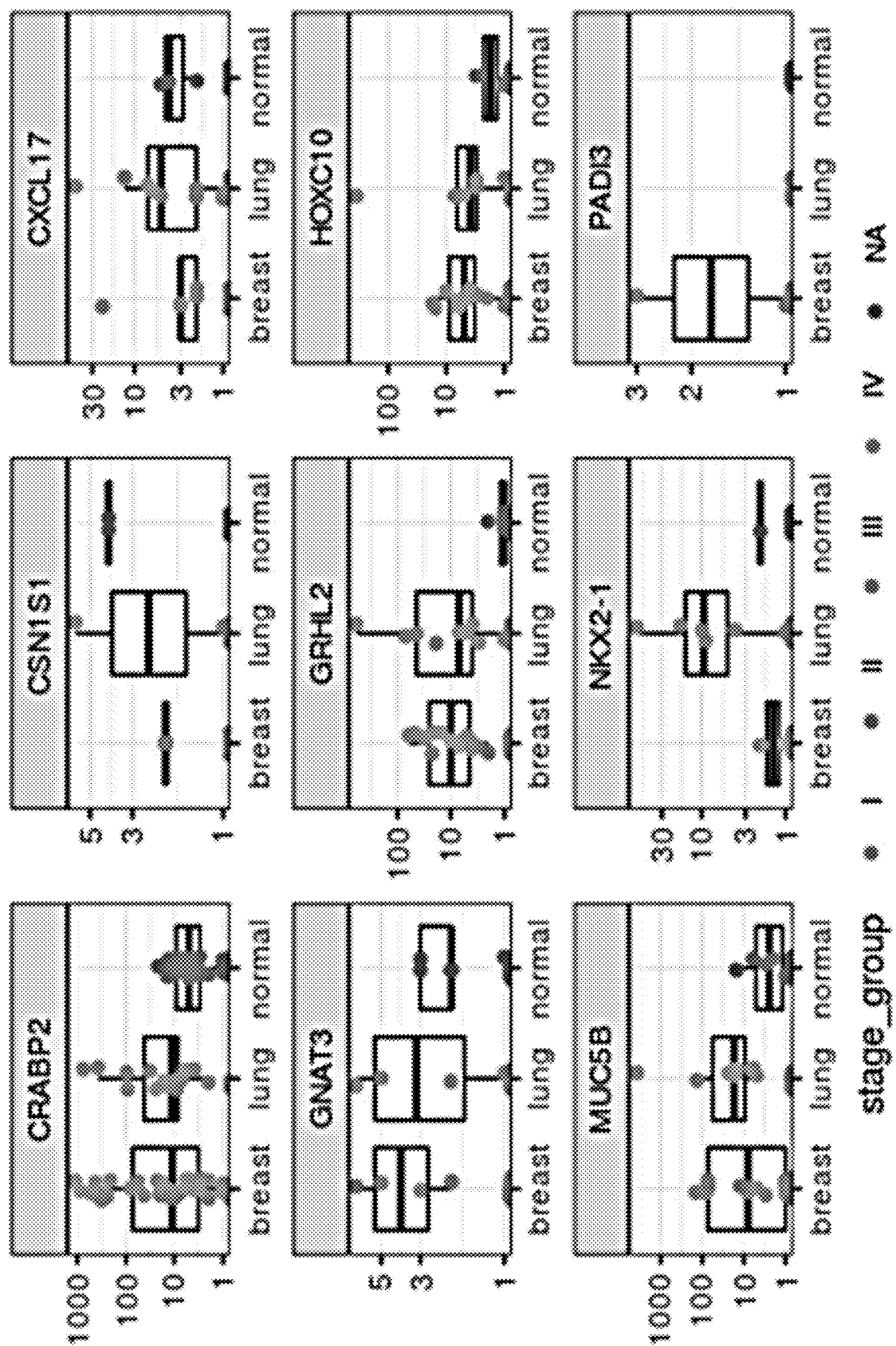
Figure 16C:
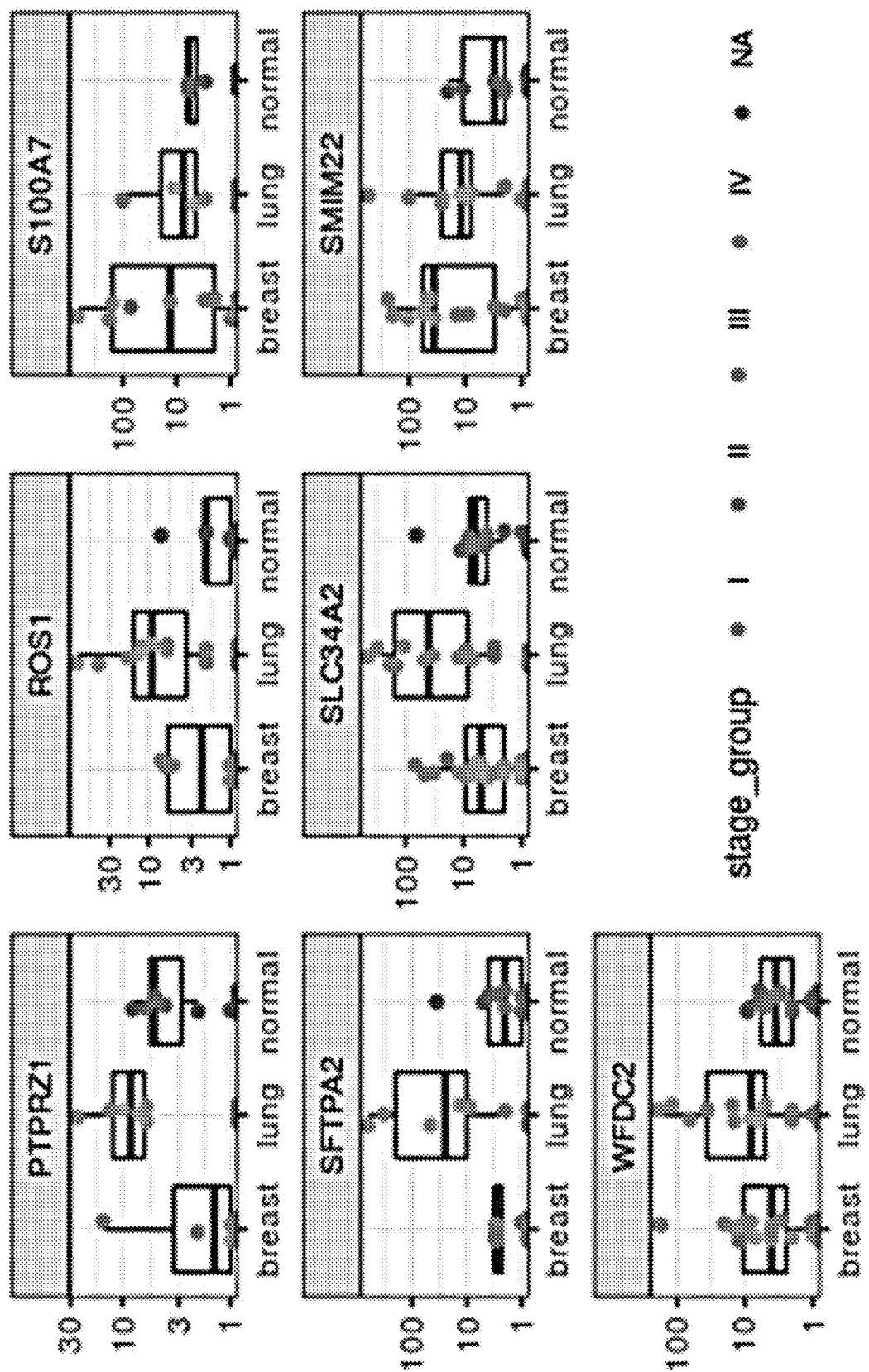
Figure 16D:
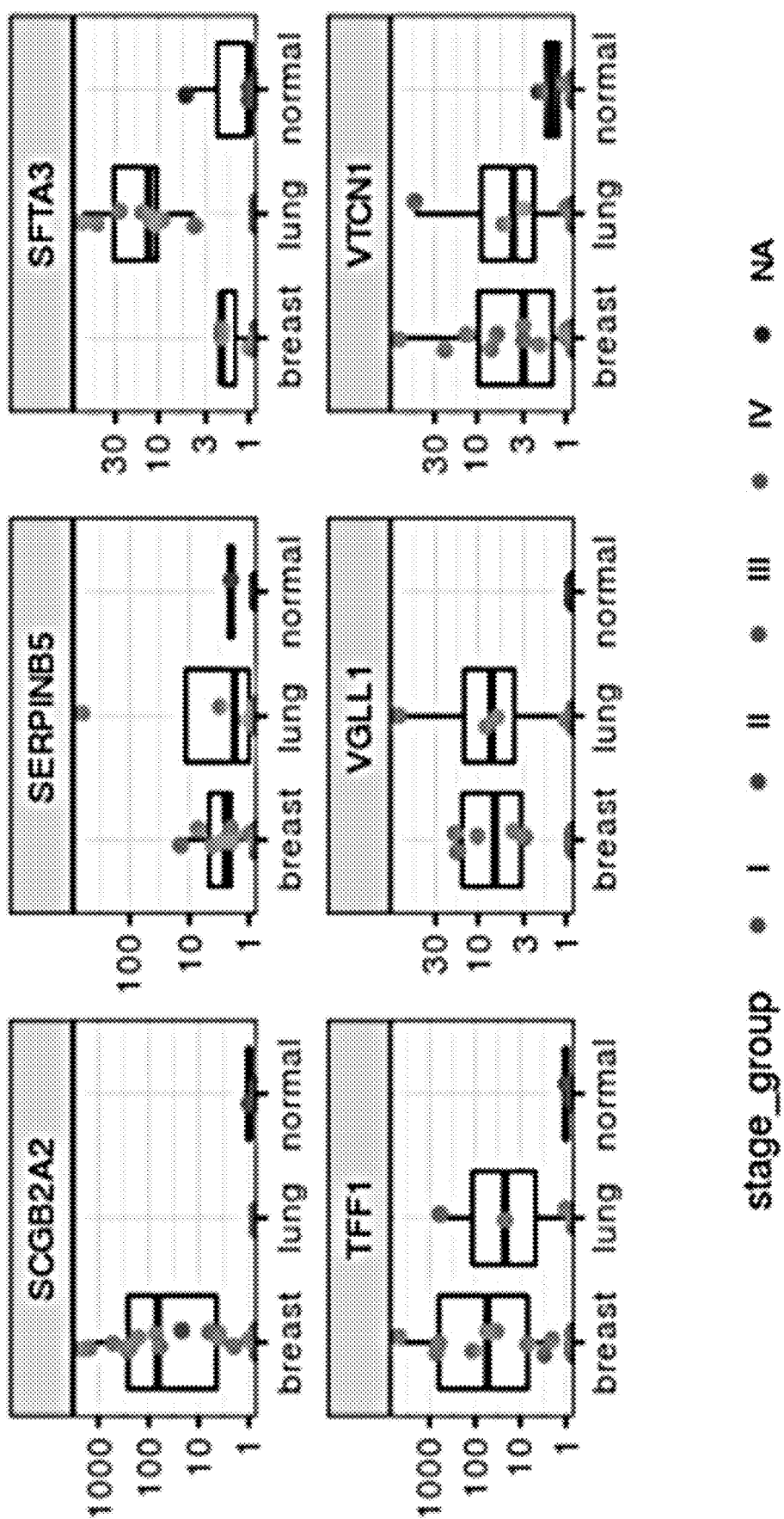

In order to determine the source of tumor-associated transcripts in the blood, concordance between cfRNA and tumor tissue RNA for dark channel biomarker genes was assessed. High concordance between cfRNA and tumor tissue expression was observed (FIG. 15A). Genes not detected in the tumor tissue were unlikely to be detected in the matched cfRNA sample, and genes detected in the tumor tissue were more likely to be detected in the matched cfRNA sample. Additionally, tumor content, measured as the product of cfDNA tumor fraction for a given patient and the gene expression in matched tumor tissue, was a strong predictor of the detectability of a DCB gene in the cfRNA of breast cancer patients (FIG. 15B).

Dark channel biomarkers (DCBs), transcripts that were not found in cfRNA from non-cancer subjects, exhibited the potential for high signal-to-noise in cancer patients. DCB signal was correlated with tumor content (measured as the product of tumor fraction in the blood and RNA expression in the tissue). cfRNA DCBs were identified in cancer participants in a tissue- and subtype-specific manner. We observed cases where high tumor tissue expression led to DCB signal amplification and enabled detection of cancer in patients with low cfDNA tumor fraction. Taken together, these data suggest that tissue-specific transcripts have potential for use in blood-based multi-cancer detection.

Example 2: Identifying Biomarkers in Heterogeneous Samples

We observed two common sources of false-positives in biomarker discovery on heterogeneous samples using standard differential expression (DE) analysis. First, the gene expression follows bimodal distribution due to genetic heterogeneity or gene amplification drop-out in both control and cancer groups. Second, a single influential outlier inflated the slope and p-value of the generalized linear model (GLM).

A method was developed to identify differentially expressed genes in highly heterogeneous samples, such as cfRNA based on tissue expression, referred to as heteroDE. The heteroDE model uses a negative binomial generalized linear model (NB-GLM). To reduce the false-positives, heteroDE includes two additional functionalities: (1) it checks if the gene expression in the non-cancer group follows bimodal distribution due to genetic heterogeneity or gene amplification drop-out; and (2) it checks if only a single outlier sample is influencing the p-value of the NB-GLM. The outlier sample is identified using Cook's distance. The NB-GLM is performed for a second time without the sample with the largest Cook's distance.

In contrast to prior differential expression (DE) methods, heteroDE uses the tumor content as a covariate in the NG-GLM. The tumor content for the non-cancer samples was set to zero. The hypothesis for a cfRNA tumor biomarker gene was that the higher of the gene's expression in the tissue and the larger the tumor fraction in the cfDNA, the more likely it is to detect that gene in cfRNA. When we applied this method to breast cancer samples, we identified 9 cfRNA biomarkers: TRGV10, SCGB2A2, CASP14, FABP7, CRABP2, VGLL1, SERPINB5, TFF1, and AC007563.5 (see Table 4). Three of these biomarkers (FABP7, SCGB2A2, CASP14) overlap with the genes identified as DCB genes.

Figure 19:
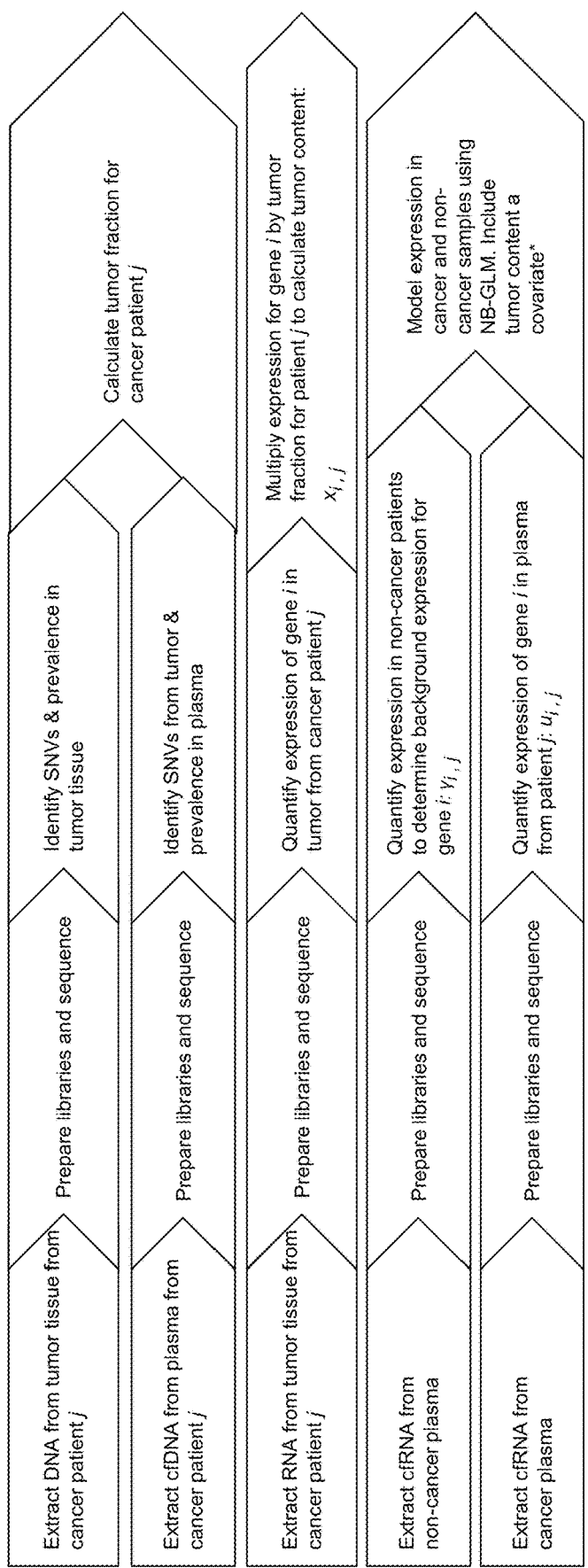
FIG. 19 illustrates a sample processing and parameter determination method, in accordance with one embodiment of the present invention.

An example workflow illustrating the sample processing and parameter determination in accordance with heteroDE is shown in FIG. 19. Tumor content was constrained to zero for non-cancer subjects, due to a lack of tissue sample. An example implementation of the workflow is given by:

$K_{i,j}$: read counts for gene i in the cfRNA of patient j;
$\mu_{i,j}$: mean read counts for gene i in the cfRNA of patient j;
$\alpha_i$: dispersion for gene i;
$\gamma_i$: the mean reads count when no tumor contents in plasma for gene i;
$x_{i,j}$: tumor contents, log 10 (tumor fraction in matched cfDNA*gene expression in matched tumor tissue)
$\beta i$: the coefficient for tumor contents;

$$K_{i,j} \sim NB(\mu_{i,j}, \alpha_i)$$

$$\log(\mu_{i,j}) = (\gamma_i + x_{i,j}\beta_i)$$

Feature selection using an information gain method was also tested. Information gain is a method to select genes with high mutual information between the binarized cfRNA gene expression and the cancer/non-cancer label. The gene expression RPM matrix was converted to a binary matrix. If the gene had an RPM>0, it was converted to 1. If the gene had an RPM=0, it was set to 0. The information gain was computed for each gene given the cancer type (e.g., lung cancer) and non-cancer label using the binary expression value. The non-cancer group for the breast cancer group was balanced with gender—only the female subjects in the non-cancer group were selected. The top 100 genes with the highest information gain were selected as the feature for modeling. The value of each gene was converted to binary value in the modeling process. These procedures were repeated for breast cancer vs. non-cancer, and colorectal cancer vs. non-cancer. The top 30 genes with the highest information gain for lung cancer are shown in Table 5, and the top 30 genes with the highest information gain for breast cancer are shown in Table 6.

In another embodiment, feature selection was carried out from cancer tissue samples to identify genes expressed in cancer tissues samples but not expressed in non-cancer participants. Libraries were prepared and sequenced as described above in Example 1. For each cancer tissue sample, we identified genes that were expressed at relatively high levels in cancer tissue (tissue RPM>10) from Dark Channels. These genes were classified as "tissue bright channel genes." The top 15 tissue bright channel genes identified are shown in Table 7.

Example 3: Validation of DCB's in a Separate Cohort

We set out to validate the DCBs identified in our CCGA cohort in an orthogonal set of breast (38) and lung (18) cancer samples obtained from a commercial vendor (Discovery Life Sciences). Stage I-IV patients were selected to assess the prevalence of DCBs across disease progression, and 38 age-matched non-cancer samples were included as controls of DCB expression in patients without cancer. In order to improve sensitivity and reduce sequencing requirements, we developed a targeted enrichment approach to select for 23 DCBs identified in our CCGA cohort. We also enriched for 33 positive control genes that are normally present in non-cancer plasma. These transcripts act as carrier material in the enrichment step, since the majority of non-cancer samples will not contain DCB transcripts. The resulting targeted RNA-seq libraries were sequenced and subsampled to a depth of 100M paired-end reads per sample, and the number of strict RNA reads quantified for both target and off-target genes. When compared to the whole transcriptome assay, we found that the targeted approach increased conversion efficiency for targeted cfRNA transcripts by 2- to 3-fold.

Of the 23 DCBs identified in our CCGA cohort, all but one (CRABP2) had a median expression (in RPM) of 0 in the non-cancer group. 19 DCBs in our panel were expressed in at least 1 cancer sample in the validation cohort (>2 unique fragments), and 16 of these DCBs were differentially expressed in at least one cancer type compared to non-cancer samples. With the increased assay efficiency and stage, we noticed that some tissue-specific markers are present in both breast and lung cancer, though they remain differentially expressed between the two groups. There are also some DCBs that are exclusively expressed in one cancer type, like SCGB2A2 in breast cancer, and ROS1, SFTA3, and SFTPA2 in lung cancer. For all of the DCBs observed in this validation cohort, the level of DCB expression in cancer samples increased with stage, with the highest expression seen for stage IV samples in our cohort, supporting the validity of these features as specific markers of cancer. Despite this trend, we also observed DCB expression in early stage cancers within our cohort, suggesting an opportunity to detect early stage cancers using an approach that enriches for DCBs. Illustrative results are shown in FIGS. 16A-D, with the number of read counts along the y-axis.

Example 4: Classification Results

Figure 17A:
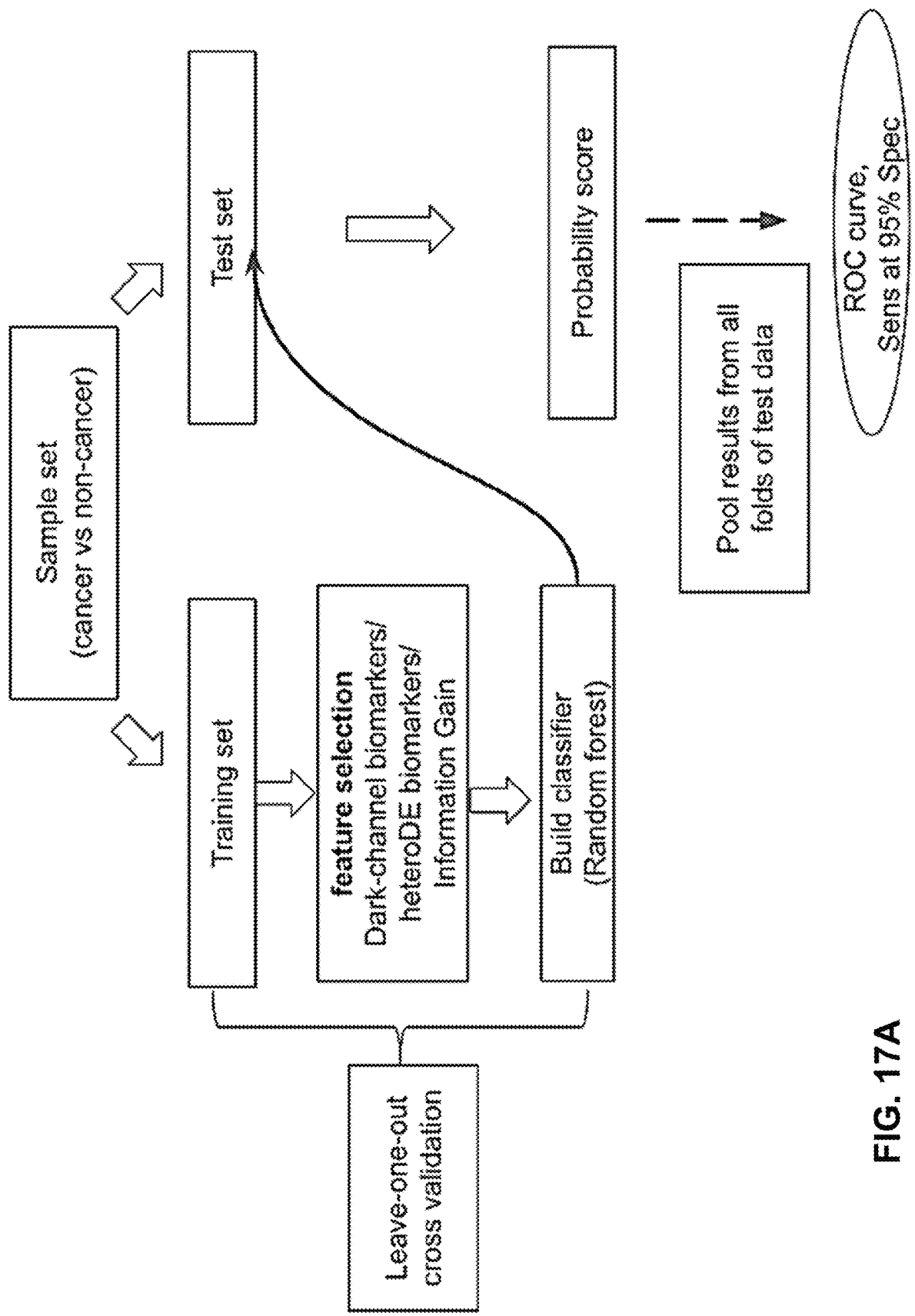
FIGS. 17A-B illustrate example classifier workflows.
Figure 17B:
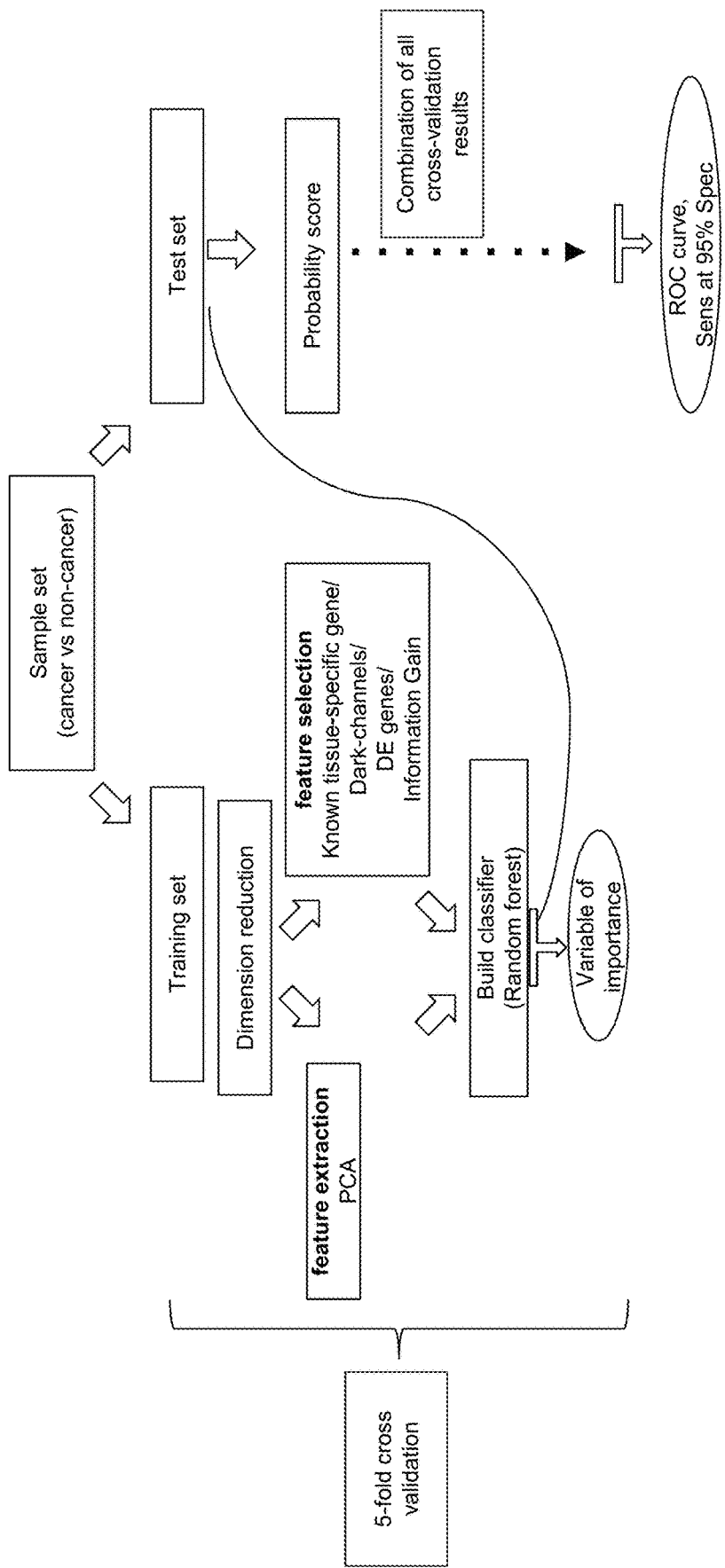

We applied leave-one-out (LOO) and 5-fold cross validation classification using different feature selection methods, including dark-channel biomarkers (DCB), heteroDE, and information gain (IG). Illustrative workflows are shown in FIGS. 17A-B. Because heteroDE utilized matched tumor tissue, this feature selection method was not applied to lung cancer/non-cancer classification due to limited number of lung tissue samples. Overall, LOO had significantly better classification performance in LOO compared to 5-fold cross validation in breast cancer/non-cancer classification, implying that the breast cancer classifier is under trained in 5-fold classification due to smaller sample sizes in each training set. DCB had the best performance (sensitivity at 98% specificity: 0.2±0.037) for lung cancer/non-cancer classifier and heteroDE had the best performance (sensitivity at 98% specificity: 0.303±0.046) for breast cancer/non-cancer classifier (Table 10).

TABLE 10

| Cancer Type | Feature Selection | Cross-Validation | Sens95spec |
| --- | --- | --- | --- |
| Lung | DCB | LOO | 0.3 ± 0.042 |
| Lung | IG | LOO | 0.333 ± 0.043 |
| Breast | heteroDE | LOO | 0.394 ± 0.049 |
| Breast | DCB | LOO | 0.212 ± 0.041 |
| Breast | IG | LOO | 0.303 ± 0.046 |
| Lung | DCB | 5-fold | 0.261 ± 0.146 |
| Breast | heteroDE | 5-fold | 0.177 ± 0.142 |

Figure 18A:
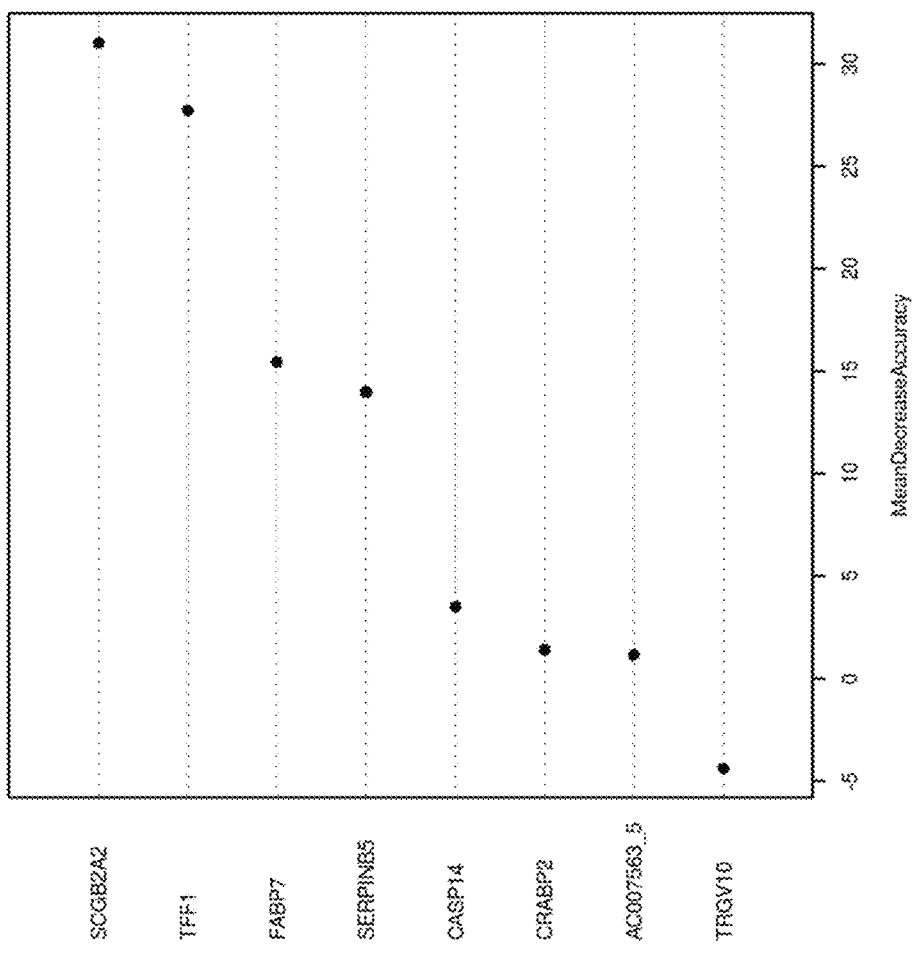
FIGS. 18A-C illustrate ROC plots showing sensitivity and specificity of example classification schemes.
Figure 18A:
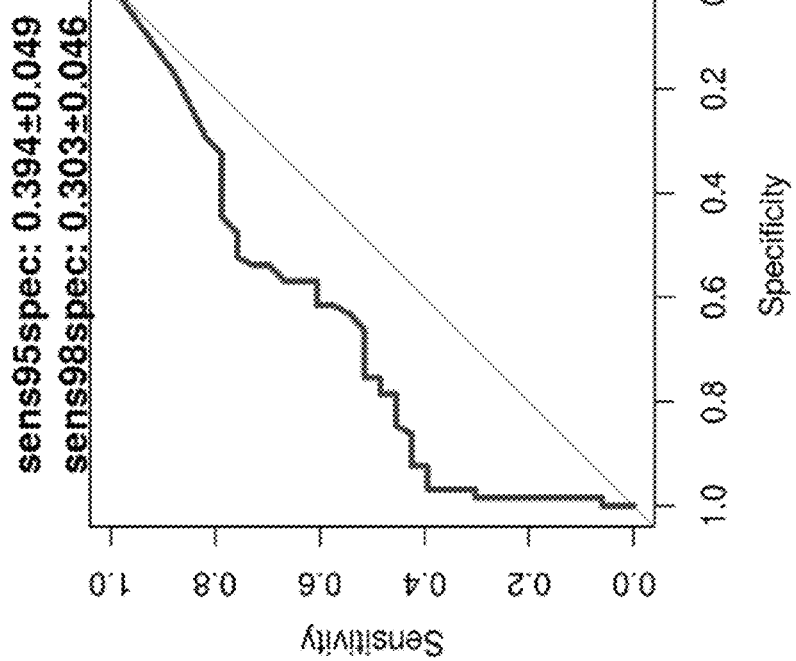
Figure 18B:
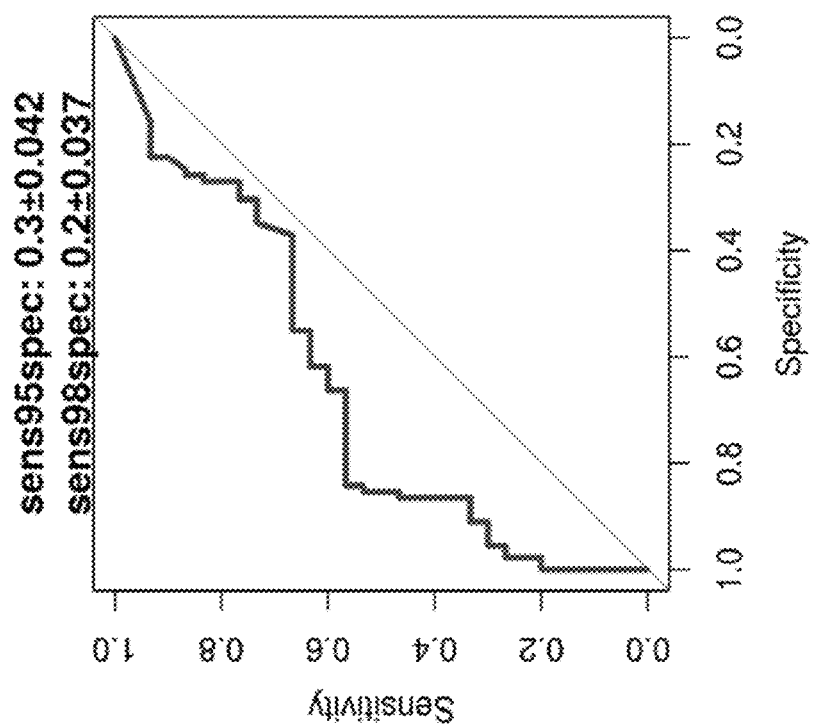
Figure 18C:
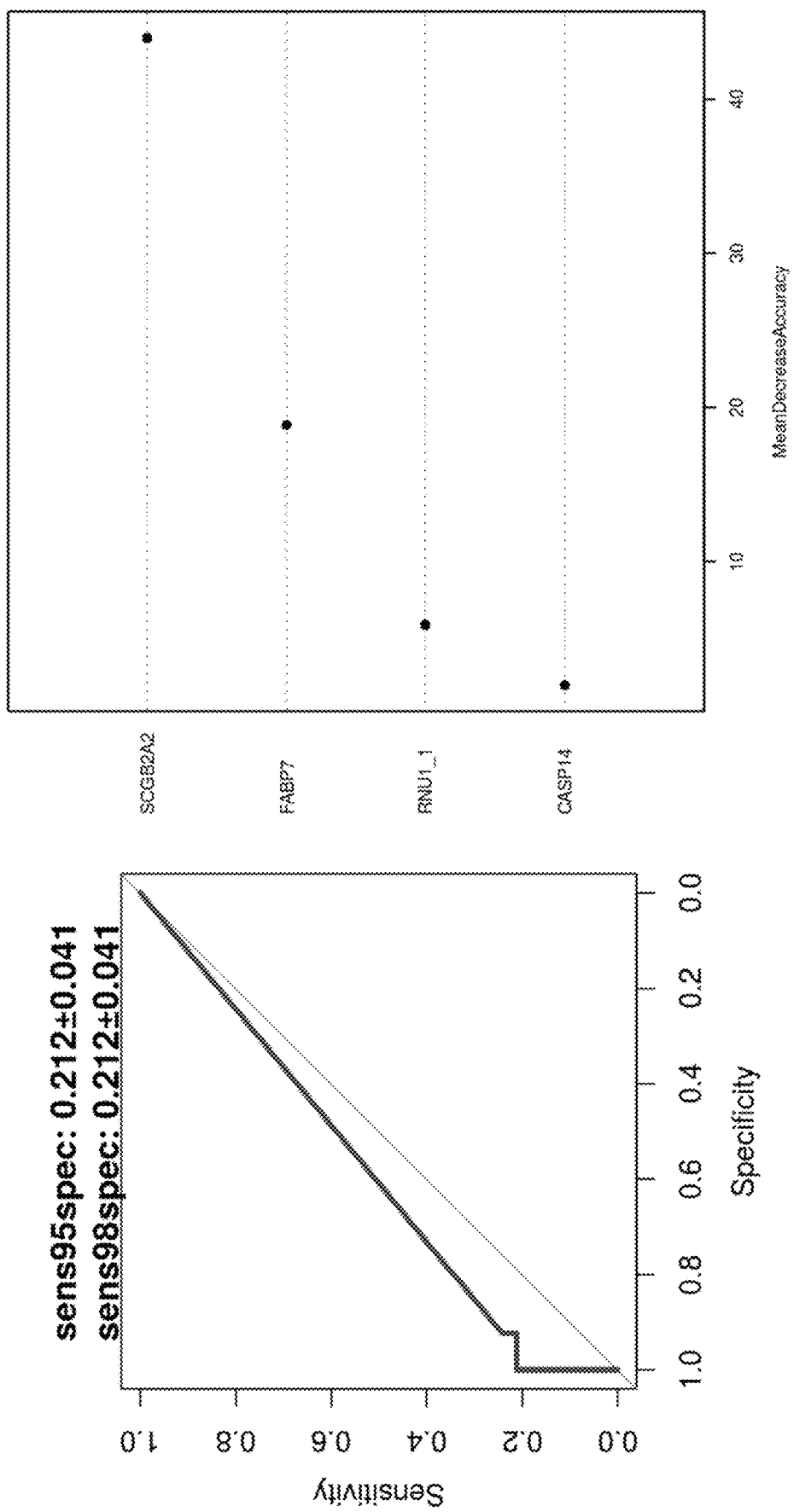

Illustrative results are also plotted in FIGS. 18A-C, which were generated using leave-one-out cross validation. FIG. 18A shows a receiver operating characteristic (ROC) plot and a variable importance plot from leave-one-out (LOO) cross-validation classification for breast vs non-cancer using the heteroDE feature selection method and a random forest classifier. The input data was counts per gene which was normalized using size factor normalization (using the estimateSizeFactors) function from the DESeq2 R package). As shown in Table 10, the sensitivity at 95% was 0.394+/−0.049.

FIG. 18B shows a ROC plot from leave-one-out (LOO) cross-validation classification for lung vs non-cancer labels using the dark channel feature selection method and a random forest classifier. The input data was normalized counts per gene in reads per million (rpm). As shown in Table 10, the sensitivity at 95% specificity was 0.3+/−0.042.

FIG. 18C shows a ROC plot and variable importance plot from leave-one-out (LOO) cross-validation classification for breast vs non-cancer labels using the dark channel feature selection method and a random forest classifier. The input data was normalized counts per gene in reads per million (rpm). As shown in Table 10, the sensitivity at 95% specificity was 0.212+/−0.041.

Example 5: Materials and Methods

Sequencing Data Processing

Raw reads were aligned to gencode v19 primary assembly with all transcripts using STAR version 2.5.3a. Duplicate sequence reads were detected and removed based on genomic alignment position and non-random UMI sequences. A majority of paired-end reads had UMI sequences exactly matching expected sequences. A subset of reads contained errors in the UMI sequence and a heuristic error correction was applied. If the UMI was within a hamming distance of 1 from an expected UMI, it was assigned to that UMI sequence. In the case where hamming distance exceeded 1, or multiple known sequences were within a hamming distance of 1, the read with the UMI error was discarded. Sets of reads sharing alignment position and corrected UMIs were error corrected via multiple sequence alignment of member reads and a single consensus sequence/alignment was generated. Read alignments were compared to annotated transcripts in gencode v19. Only reads spanning annotated exon-exon junctions were counted to the remove false counts resulting from DNA contaminating reads.

Sample Collection

Whole blood was collected in Streck Cell-free DNA BCT tubes, which were shipped and stored at ambient temperature prior to plasma separation. Whole blood was spun at 1600 g for 10 min at 4° C. in a swing-bucket rotor to separate plasma. The plasma layer was transferred to a separate tube and spun at 15000 g for 12 min at 4° C. to further remove cellular contaminants. Double-spun plasma was stored at −80° C. and thawed at room temperature prior to extraction to avoid the formation of cryoprecipitates.

Sample Selection Criteria

We selected a subset of stage III breast, lung, and colorectal cancer samples from the Circulating Cell-free Genome Atlas study (CCGA, NCT02889978). We required that the selected patients had at least two tubes of unprocessed grade 1-2 plasma (no hemolysis), with 6-8 mL of plasma per patient. We further required that selected patients had matched cfDNA sequencing data from previous studies. Once the cancer patients were selected, we selected an equal number of non-cancer samples matched for age, gender, and ethnicity to the cancer samples. Based on this criteria, we selected 210 samples. These samples were randomized into batches of 14 using a randomization function in R that ensured a random mixture of cancer types (cancer and non-cancer samples) within each batch.

Sample Processing

Cell-free nucleic acids were extracted from up to 8 mL of frozen plasma using the circulating miRNA protocol from the QIAamp Circulating Nucleic Acids kit (Qiagen, 55114). The extracted material was DNase treated using the RNase-free DNase Set (Qiagen, 79254) according to the manufacturer's instructions and quantified using the High Sensitivity RNA Fragment Analyzer kit (Agilent, DNF-472). Reverse transcription and adapter ligation was performed using the TruSeq RNA Exome kit (Illumina, 20020189 The resulting libraries were depleted of abundant sequences using the AnyDeplete for Human rRNA and Mitochondrial Kit (Tecan, 9132), supplemented with a custom set of depletion targets.

Sequenced samples were screened and those exhibiting low quality control metrics were excluded from subsequent analysis. One assay metric and three pipeline metrics were chosen as "red flags" and were used to exclude samples with poor metrics. The assay metric measured whether samples had sufficient material for sequencing, and the pipeline metrics were sequencing depth, RNA purity, and cross-sample contamination.

Gene Expression Quantification

Initial inspection of the data revealed varying levels of residual DNA in cfRNA samples despite the DNase digestion step during library preparation. The level of contamination was minimal (<6 haploid genome equivalents per sample), and was not correlated with the amount of cfDNA prior to digestion or batch-specific issues. Rather, it appears to be stochastic, in line with previous reports.

A QC metric, "quantile 95 strand specificity" defined as the strand specificity of genes at or below the 95th quantile of expression, was used to assess the level of DNA contamination in each sample. UHR positive control samples exhibited high quantile 95 strand specificity (>0.85). cfRNA quantile 95 strand specificity values were spread across a wide range (0.52-0.89). For reference, cfDNA samples have a quantile 95 strand specificity of ~0.5, suggesting that some cfRNA samples are dominated by signal from residual DNA. The read strand colors show even distribution of sense and anti-sense reads in NC67 versus only sense reads in NC3. Additionally, there is abundant coverage across both introns and exons in NC67, as would be expected with presence of DNA. The distribution of fragment length in samples with high levels of DNA contamination shows that they mimic the length distribution of cfDNA (median 160), strongly suggesting that undigested cfDNA is the major contaminant.

Samples with quantile 95 strand specificity below 0.84 were flagged and removed from subsequent analysis. To further guard against the inflation of RNA counts due to DNA contamination, the gene counts presented here are generated using strict counts, defined as read pairs where at least one of the two reads maps across an exon-exon junction. An experiment performed using varying levels of cfDNA spiked into a cfRNA sample showed that the estimation of RNA levels using strict counts remains unchanged, supporting the use of strict counts in the pilot study samples for quantifying and comparing gene expression.

Dark-Channel Features Election

The dark channel genes were identified by the following criteria: 1) The median expression (in RPM) of this gene in the non-cancer group is 0, and the standard deviation of this gene is less than 0.1 RPM. The dark channel biomarkers (DCB) for each cancer type were identified using the following criteria: 1) There are at least two samples in the specified cancer group for which the gene is expressed, 2) the RPM of the second highest expressed sample is greater than 0.1, and 3) the gene is differentially expressed in the specified cancer group compared to the non-cancer group (p-value<2e-02 for lung cancer and p-value<2e-01 for breast cancer). The p-value of two-group differential expression was calculated by the edgeR package. There are 816 genes with FDR<0.05 between lung cancer and non-cancer groups. There are 28 genes with FDR<0.05 between breast cancer and non-cancer groups. There are 4 genes with FDR<0.05 between colorectal cancer and non-cancer groups. For the boxplot and heatmap, we only displayed the most significant differentially expressed genes (FDR<2e-06 for lung and breast cancer and FDR<2e-02 for colorectal cancer).

Annotation of tissue-specific genes was performed as follows. The tissue-specific gene files for lung, breast, and colon cancers were downloaded from the Human Protein Atlas website (www.proteinatlas.org/). Tissue-specific genes are divided into three categories: 1) Tissue Enriched: At least 4-fold higher mRNA levels in a particular tissue as compared to all other tissues, 2) Group Enriched: At least 4-fold higher mRNA levels in a group of 2-5 tissues, 3) Tissue Enhanced: At least 4-fold higher mRNA levels in a particular tissue as compared to average levels in all tissues. All three categories were included in our definition of tissue-specific genes.

In order to test enrichment of the tissue-specific genes. 1) Fisher's exact test was applied to test the independence between lung DCB and lung-specific genes for all the annotated human genes. 2) Fisher's exact test was applied to test the independence between breast DCB and breast-specific genes for all the annotated human genes.

REFERENCES

Klein et al. Development of a comprehensive cell-free DNA (cfDNA) assay for early detection of multiple tumor types: The Circulating Cell-free Genome Atlas (CCGA) study. *ASCO* (2018).

Uhlén et al. Tissue-based map of the human proteome (www.proteinatlas.org). *Science* doi:10.1126/science.1260419 (2015).

A. M. Newman, et al., An ultrasensitive method for quantitating circulating tumor DNA with broad patient coverage. *Nat. Med.* 20, 548-554 (2014).

E. Kirkizlar, et al., Detection of Clonal and Subclonal Copy-Number Variants in Cell-Free DNA from Patients with Breast Cancer Using a Massively Multiplexed PCR Methodology. *Transl. Oncol.* 8, 407-416 (2015).

S. Y. Shen, et al., Sensitive tumour detection and classification using plasma cell-free DNA methylomes. *Nature* 563, 579-583 (2018).

C. Bettegowda, et al., Detection of circulating tumor DNA in early- and late-stage human malignancies. *Sci. Transl. Med.* 6, 224ra24 (2014).

K. C. A. Chan, et al., Noninvasive detection of cancer-associated genome-wide hypomethylation and copy number aberrations by plasma DNA bisulfite sequencing. *Proc. Natl. Acad. Sci. U S. A.* 110, 18761-18768 (2013).

I. S. Hague, O. Elemento, Challenges in Using ctDNA to Achieve Early Detection of Cancer. *bioRxiv*, 237578 (2017).

K. C. A. Chan, et al., Cancer genome scanning in plasma: detection of tumor-associated copy number aberrations, single-nucleotide variants, and tumoral heterogeneity by massively parallel sequencing. *Clin. Chem.* 59, 211-224 (2013).

C. Abbosh, et al., Phylogenetic ctDNA analysis depicts early-stage lung cancer evolution. *Nature* 545, 446-451 (2017).

K.-W. Lo, et al., Analysis of Cell-free Epstein-Barr Virus-associated RNA in the Plasma of Patients with Nasopharyngeal Carcinoma. *Clin. Chem.* 45, 1292-1294 (1999).

M. S. Kopreski, F. A. Benko, L. W. Kwak, C. D. Gocke, Detection of tumor messenger RNA in the serum of patients with malignant melanoma. *Clin. Cancer Res. Off. J. Am. Assoc. Cancer Res.* 5, 1961-1965 (1999).

J. D. Arroyo, et al., Argonaute2 complexes carry a population of circulating microRNAs independent of vesicles in human plasma. *Proc. Natl. Acad. Sci. U S. A.* 108, 5003-5008 (2011).

P. M. Godoy, et al., Large Differences in Small RNA Composition Between Human Biofluids. *Cell Rep.* 25, 1346-1358 (2018).

M. F. de Souza, et al., Circulating mRNAs and miRNAs as candidate markers for the diagnosis and prognosis of prostate cancer. *PLoS ONE* 12 (2017).

G. Y. F. Ho, et al., Differential expression of circulating microRNAs according to severity of colorectal neoplasia. *Transl. Res.* 166, 225-232 (2015).

I. Lee, D. Baxter, M. Y. Lee, K. Scherler, K. Wang, The importance of standardization on analyzing circulating RNA. *Mol. Diagn. Ther.* 21, 259-268 (2017).

X. Q. Chen, et al., Telomerase RNA as a detection marker in the serum of breast cancer patients. *Clin. Cancer Res. Off. J. Am. Assoc. Cancer Res.* 6, 3823-3826 (2000).

17. R. C. Kamm, A. G. Smith, Ribonuclease activity in human plasma. *Clin. Biochem.* 5, 198-200 (1972).

T. El-Hefnawy, et al., Characterization of amplifiable, circulating RNA in plasma and its potential as a tool for cancer diagnostics. *Clin. Chem.* 50, 564-573 (2004).

N. B. Y. Tsui, E. K. O. Ng, Y. M. D. Lo, Stability of endogenous and added RNA in blood specimens, serum, and plasma. *Clin. Chem.* 48, 1647-1653 (2002).

J. D. Arroyo, et al., Argonaute2 complexes carry a population of circulating microRNAs independent of vesicles in human plasma. *Proc. Natl. Acad. Sci. U S. A.* 108, 5003-5008 (2011).

G. J. S. Talhouarne, J. G. Gall, 7SL RNA in vertebrate red blood cells. *RNA* 24, 908-914 (2018).

L. A. Hancock, et al., Muc5b overexpression causes mucociliary dysfunction and enhances lung fibrosis in mice. *Nat. Commun.* 9, 1-10 (2018).

T. Handa, et al., Caspase14 expression is associated with triple negative phenotypes and cancer stem cell marker expression in breast cancer patients. *J. Surg. Oncol.* 116, 706-715 (2017).

R. Hrstka, et al., The pro-metastatic protein anterior gradient-2 predicts poor prognosis in tamoxifen-treated breast cancers. *Oncogene* 29, 4838-4847 (2010).

M. Pizzi, et al., Anterior gradient 2 overexpression in lung adenocarcinoma. *Appl. Immunohistochem. Mol. Morphol. AIMM* 20, 31-36 (2012).

H. Cho, A. B. Mariotto, L. M. Schwartz, J. Luo, S. Woloshin, When do changes in cancer survival mean progress? The insight from population incidence and mortality. *J. Natl. Cancer Inst. Monogr.* 2014, 187-197 (2014).

Y. M. Lo, et al., Rapid clearance of fetal DNA from maternal plasma. *Am. J. Hum. Genet.* 64, 218-224 (1999).

M. A. Watson, T. P. Fleming, Mammaglobin, a mammary-specific member of the uteroglobin gene family, is overexpressed in human breast cancer. *Cancer Res.* 56, 860-865 (1996).

G. H. Lewis, et al., Relationship between molecular subtype of invasive breast carcinoma and expression of gross cystic disease fluid protein 15 and mammaglobin. *Am. J. Clin. Pathol.* 135, 587-591 (2011).

R.-Z. Liu, et al., A fatty acid-binding protein 7/RXRβ pathway enhances survival and proliferation in triple-negative breast cancer. *J. Pathol.* 228, 310-321 (2012).

A. Cordero, et al., FABP7 is a key metabolic regulator in HER2+ breast cancer brain metastasis. *Oncogene* 38, 6445-6460 (2019).

H. Zhang, et al., The proteins FABP7 and OATP2 are associated with the basal phenotype and patient outcome in human breast cancer. *Breast Cancer Res. Treat.* 121, 41-51 (2010).

J. Xiao, et al., Eight potential biomarkers for distinguishing between lung adenocarcinoma and squamous cell carcinoma. *Oncotarget* 8, 71759-71771 (2017).

M. Grageda, P. Silveyra, N. J. Thomas, S. L. DiAngelo, J. Floros, DNA methylation profile and expression of surfactant protein A2 gene in lung cancer. *Exp. Lung Res.* 41, 93-102 (2015).

Z. Zhang, et al., High expression of SLC34A2 is a favorable prognostic marker in lung adenocarcinoma patients. *Tumour Biol. J. Int. Soc. Oncodevelopmental Biol. Med.* 39, 1010428317720212 (2017).

F. Diehl, et al., Circulating mutant DNA to assess tumor dynamics. *Nat. Med.* 14, 985-990 (2008).

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

What is claimed is:

1. A method of measuring a subpopulation of cell-free RNA (cfRNA) molecules of a subject, the method comprising:
    a. sequencing the cfRNA molecules to produce cfRNA sequence reads;
    b. sequencing cellular RNA extracted from cells of the subject to produce cellular sequence reads;
    c. performing a filtering procedure to produce a non-excluded population of cfRNA sequence reads, wherein the filtering comprises excluding cfRNA sequence reads that match one or more of the cellular sequence reads; and
    d. quantifying one or more of the non-excluded sequence reads.

2. The method of claim 1, wherein sequencing the cfRNA molecules comprises:
    (a) reverse transcription to produce cDNA molecules, and sequencing the cDNA molecules to produce the cfRNA sequence reads;
    (b) (i) reverse transcribing the cfRNA molecules to produce a plurality of cDNA/RNA hybrid molecules, (ii) synthesizing a plurality of double-stranded cDNA molecules from the cDNA/RNA hybrid molecules, (iii) ligating a plurality of double-stranded polynucleotide adapters to the plurality of double-stranded cDNA molecules, thereby producing a sequencing library; and (iv) sequencing at least a portion of the sequencing library to produce the cfRNA sequence reads;
    (c) whole transcriptome sequencing; or
    (d) enriching the cfRNA molecules or cDNA molecules thereof for one or more target polynucleotides.

3. The method of claim 1, wherein the non-excluded sequence reads only include reads or read pairs that overlap an exon-exon junction.

4. The method of claim 1, wherein the cfRNA is from a biological test sample of the subject comprising a biological fluid or wherein the cfRNA molecules are obtained from blood, a blood fraction, plasma, or serum of the subject.

5. The method of claim 1, wherein the cells are obtained from blood or a blood fraction of the subject, or wherein the cells are white blood cells (WBCs).

6. The method of claim 1, further comprising detecting a condition of the subject, wherein detecting the condition comprises detecting one or more non-excluded sequence reads above a threshold.

7. The method of claim 6, wherein detecting one or more non-excluded sequence reads above a threshold comprises:
    (a)(i) detection above background, or (ii) detection at a level that is greater than a level of corresponding sequence reads in subjects that do not have the condition
    (b) detecting the one or more sequence reads at a level that is at least about 10 times greater than a level of corresponding sequence reads in subjects that do not have the condition; or
    (c) detection above a threshold value of 0.5 to 5 reads per million (RPM).

8. The method of claim 6, wherein detecting one or more non-excluded sequence reads above a threshold comprises:
    (a) determining an expression level of a plurality of target cfRNA molecules;
    (b) determining an indicator score for each target cfRNA molecule by comparing the expression level of each of the target cfRNA molecules to an RNA tissue score matrix;

(c) aggregating the indicator scores for each target cfRNA molecule; and, (d) detecting presence of the condition in the subject when the indicator score exceeds a threshold value.

9. The method of claim 6, wherein detecting one or more non-excluded sequence reads above a threshold comprises inputting the sequence reads into a machine learning or deep learning model.

10. The method of claim 9, wherein (a) the machine learning or deep learning model comprises logistic regression, random forest, gradient boosting machine, Naïve Bayes, neural network, or multinomial regression; or (b) the machine learning or deep learning model transforms values of one or more features to a disease state prediction for the subject through a function comprising learned weights.

11. The method of claim 6, wherein the condition is cardiovascular disease, liver disease, or a cancer.

12. The method of claim 11, wherein the condition is a liver disease selected from non-alcoholic fatty liver disease (NAFLD), alcoholic steatohepatitis (ASH), non-alcoholic steatohepatitis (NASH), liver fibrosis, liver cirrhosis, hepatocellular carcinoma (HCC), and any combination thereof.

13. The method of claim 11, wherein the condition is a cancer comprising:
(i) a carcinoma, a sarcoma, a myeloma, a leukemia, a lymphoma, a blastoma, a germ cell tumor, or any combination thereof;
(ii) a carcinoma selected from the group consisting of adenocarcinoma, squamous cell carcinoma, lung cancer, nasopharyngeal, colorectal, anal, liver, urinary bladder, testicular, cervical, ovarian, gastric, esophageal, head-and-neck, pancreatic, prostate, renal, thyroid, melanoma, and breast carcinoma;
(iii) hormone receptor negative breast carcinoma or triple negative breast carcinoma;
(iv) a sarcoma selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma;
(v) a leukemia selected from the group consisting of myelogenous, granulocytic, lymphatic, lymphocytic, and lymphoblastic leukemia; or
(vi) a lymphoma selected from the group consisting of: Hodgkin's lymphoma and Non-Hodgkin's lymphoma.

14. The method of claim 6, wherein
(a) the one or more non-excluded sequence reads detected above a threshold originate from a transcript of a diseased cell, and the method further comprises the step of identifying the tissue origin of the diseased cell, wherein the tissue origin is optionally selected from the group consisting of pancreatic tissue, liver tissue, lung tissue, brain tissue, uterus tissue, renal tissue, breast tissue, fat, colon tissue, rectum tissue, heart tissue, skeletal muscle tissue, prostate tissue and thyroid tissue;
(b) the one or more non-excluded sequence reads detected above a threshold originate from a transcript of a cancer cell, and the method further comprises determining a cancer cell type or tissue of origin of the cancer in the subject;
(c) the one or more non-excluded sequence reads detected above a threshold are sequence reads of one or more target polynucleotides enriched from the cfRNA molecules or amplicons thereof; or
(d) the one or more non-excluded sequence reads detected above a threshold are sequence reads for cfRNA molecules derived from 1 to 20 target genes.

15. The method of claim 6, wherein
(a): (i) the condition is cancer, and (ii) the one or more non-excluded sequence reads detected above a threshold are sequence reads for cfRNA molecules derived from one or more genes selected from the group consisting of: AGR2, BPIFA1, CASP14, CSN1S1, DISP2, EIF2D, FABP7, GABRG1, GNAT3, GRHL2, HOXC10, IDI2-AS1, KRT16P2, LALBA, LINC00163, NKX2-1, OPN1SW, *PADI*3, PTPRZ1, ROS1, S100A7, SCGB2A2, SERPINB5, SFTA3, SFTPA2, SLC34A2, TFF1, VTCN1, WFDC2, MUC5B, SMIM22, CXCL17, RNU1-1, and KLK5;
(b): (i) the condition is lung cancer, and (ii) the one or more non-excluded sequence reads detected above a threshold are sequence reads for cfRNA molecules derived from one or more genes selected from the group consisting of: ROS1, NKX2-1, GGTLC1, SLC34A2, SFTPA2, BPIFA1, SFTA3, GABRG1, AGR2, GNAT3, MUC5B, SMIM22, CXCL17, and WFDC2;
(c): (i) the condition is breast cancer, and (ii) the one or more non-excluded sequence reads detected above a threshold are sequence reads for cfRNA molecules derived from one or more genes selected from the group consisting of: SCGB2A2, CSN1S1, VTCN1, FABP7, LALBA, RNU1-1, OPN1SW, CASP14, KLK5, and WFDC2;
(d): (i) the condition is breast cancer, and (ii) the one or more non-excluded sequence reads detected above a threshold are sequence reads for cfRNA molecules derived from one or more genes selected from the group consisting of: CASP14, CRABP2, FABP7, SCGB2A2, SERPINB5, TRGV10, VGLL1, TFF1, and AC007563.5; or
(e): (i) the condition is liver disease, and (ii) the one or more non-excluded sequence reads detected above a threshold are sequence reads for cfRNA molecules derived from one or more genes selected from the group consisting of: AKR1B10, C3, and PIEXO2.

16. The method of claim 6, further comprising selecting a treatment based on the condition detected and optionally treating the subject with the selected treatment.

17. The method of claim 16, wherein the condition is cancer, and the treatment comprises surgical resection, radiation therapy, or administering an anti-cancer agent.

* * * * *